United States Patent [19]

Bundy

[11] 4,112,224

[45] Sep. 5, 1978

[54] BIHETEROCYCLIC-9,11-TRIDEOXY-PGF COMPOUNDS

[75] Inventor: Gordon L. Bundy, Portage, Mich.

[73] Assignee: The Upjohn Company, Kalamazoo, Mich.

[21] Appl. No.: 810,811

[22] Filed: Jun. 30, 1977

Related U.S. Application Data

[63] Continuation-in-part of Ser. No. 714,390, Aug. 16, 1976, abandoned, and Ser. No. 800,623, May 26, 1977, abandoned.

[51] Int. Cl.$^2$ ............... C07D 231/04; C07D 231/06; C07D 261/02; C01B 15/02
[52] U.S. Cl. .................... 542/426; 542/453; 542/468; 260/140; 260/141; 544/131; 544/137; 544/140; 544/360; 544/368; 544/371; 548/369; 562/471; 260/295 AM; 562/472; 562/465; 260/307 FA; 562/503; 562/463; 562/464; 260/343.3 R; 260/343.6; 260/943; 260/961; 424/226; 424/245; 424/272; 424/273 R; 542/414; 542/417; 542/420; 542/423; 542/424; 542/427; 542/439; 542/440; 542/447
[58] Field of Search ....... 260/250 A, 250 AC, 310 D, 260/514 D, 141, 309.6, 307 FA; 542/439, 427, 440, 420, 447, 423, 468, 424, 426, 453, 417

[56] References Cited

PUBLICATIONS

Bundy et al, Chemical Abstracts, vol. 75, #48495r (1971).
Linke et al, Chemical Abstracts, vol. 78, #111275y (1973).
Heyman et al, Chemical Abstracts, vol. 79, #137071z (1973).
Corey et al, Proc. Nat. Acad. Sci. U.S.A., vol. 72, No. 9, pp. 3355 to 3358 (1975).
Bergstroem et al, Chemical Abstracts, vol. 66, #10640h (1967).
Struijk et al, Chemical Abstracts, vol. 66, #65151g (1967).
Pappo et al, Chemical Abstracts, vol. 75 #'s 48491m to 48494q (1971).

*Primary Examiner*—Floyd D. Higel
*Attorney, Agent, or Firm*—Robert A. Armitage

[57] ABSTRACT

The present specification; provides bicyclic nitrogen-containing 9,11,15-trideoxy-prostaglandin F analogs which are useful anti-inflammatory agents, anti-asthma agents, and platelet aggregation inhibitors, and a process for their preparation. Included are compounds of the following structural formulas:

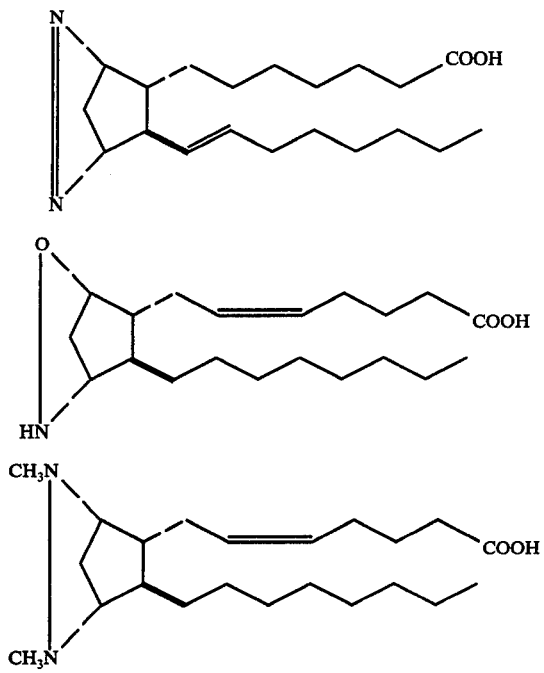

Especially described in the present specification are 9,11-trideoxy-9α,11α-azo-PGF-type; 9,11,15-trideoxy-11α,9α-epoxyimino-PGF-type; 9,11,15-trideoxy-9α,11α-epoxyimino-PGF-type; N,N'dialkyl-9,11,15-trideoxy-9α11α-hydrazino-PGF-type; N,N'-bis(alkylcarbonyl)-9,11,15-trideoxy-9α,11α-hydrazino-PGF-type; N-alkyl-9,11,15-trideoxy-11α,9α-epoxyimino-PGF-type; N-(alkylcarbonyl)-9,11,15-trideoxy-11α,9α-epoxyimino-PGF-type; N-alkyl-9,11,15-trideoxy-9α,11α-epoxyimino-PGF-type; N-(alkylcarbonyl)-9,11,15-trideoxy-9α,11α-epoxyimino-PGF-type; 9,11,15-trideoxy-9α,11α-alkylhydrazino-PGF-type; 9,11,15-trideoxy-9α,11-α-(alkylcarbonyl)hydrazino-PGF-type; 9,11,15-trideoxy-11α,9α-alkylhydrazino-PGF-type; and 9,11,15-trideoxy-11α,9α-(alkylcarbonyl)-hydrazino-PGF-type compounds.

52 Claims, No Drawings

BIHETEROCYCLIC-9,11-TRIDEOXY-PGF COMPOUNDS

CROSS REFERENCE TO RELATED APPLICATIONS

This application is a continuation-in-part of Ser. No. 714,390, filed August 16, 1976, now abandoned, and Ser. No. 800,623, filed May 26, 1977, now abandoned.

BACKGROUND OF THE INVENTION

This invention provides novel compositions of matter. This invention further provides novel processes for producing these compositions of matter. This invention further provides novel chemical intermediates useful in the above processes.

This invention is specifically concerned with novel bicyclic nitrogen-containing compounds which are analogs of the prostaglandins, e.g.,

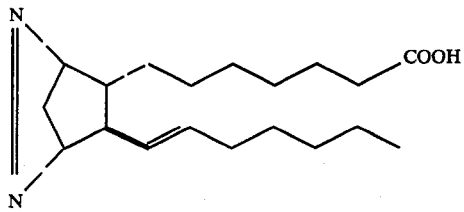

Included within the scope of this invention, in addition to such 9α, 11α-azo-9,11,15-trideoxy-PGF-type compounds, are 9α,11α-epoxyimino-9,11,15-trideoxy-PGF-type compounds and N,N'-dialkyl-9α,11α-hydrazino-9,11,15-trideoxy-PGF-type compounds, e.g.,

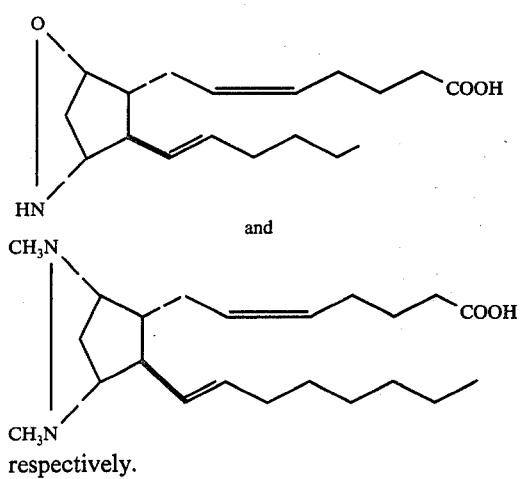

respectively.

Accordingly, the present invention is concerned with biheterocyclic, nitrogen-containing analogs of the prostaglandins, e.g., 9α, 11α-azo-, 9α-11α-epoxyimino, 11α-9α-epoxyimino-, and N,N'-alkyl or alkylcarbonylhydrazino-. Thus each of the above compounds is a derivative of prostane which has the following structure and carbon atom numbering

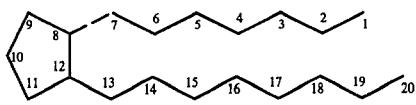

For a discussion of the use of the corresponding C-1 carboxylic acid derivatives, i.e., the prostaglandins, see, for example, Bergstrom et al., Pharmacol. Rev. 20, 1 (1968), and references cited therein. A systematic name for prostanoic acid, the above-mentioned C-1 carboxylic acid, is 7-[2β-octyl)-cyclopen-1α-yl]-heptanoic acid.

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (~) herein will represent attachment of substituents in either the alpha or beta configuration or attachment in a mixture of alpha and beta configurations.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammaliam tissues, for example, sheep vesicular glands, swine lung, or human seminal plasma, from carbonyl and/or double bond reduction of the prostaglandin so obtained. See, for example, Bergstrom et al., cited above. The mirror image of ech of these formulas, represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or "PG" will mean the optically active form of that prostaglandin thereby referred to with the same absolute configuration as $PGE_1$ obtained from mammalian tissues. When reference to the racemic form of one of those prostaglandins is intended, the work "racemic" or "dl" will precede the prostaglandin name.

The term "prostaglandin-type" (PG-type) product, as used herein, refers to any bicyclic cyclopentane derivative which is useful as an antiinflammatory agent, as indicated herein.

The term prostaglandin-type intermediate, as used herein, refers to any cyclopentane derivative useful in preparing a prostaglandin-type product.

The formulas as drawn herein, which depict a prostaglandin-type product or an intermediate useful in preparing a prostaglandin-type product, each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type product.

The term "prostaglandin analog", as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type compound herein, the term prostaglandin analog refers to the compound of that formula, or a mixture comprising that compound and the enantiomer, thereof.

See U.S. Pat. Nos. 3,950,363 and 4,028,350 for a description of 9α,11α-or 11α-9α-epoxymethano-9,11,15- trideoxy-PGF compounds corresponding to certain compounds of the present invention. See also E. J. Corey, et al., Biochemistry, 72:3355-3358 (1975) for a disclosure of 9,11-dideoxy-9α-azo-PGF$_2$.

SUMMARY OF THE INVENTION

The present invention particularly and especially provides a prostaglandin analog of the formula

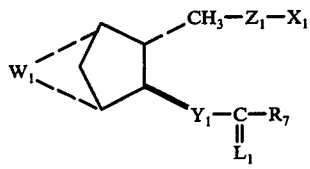

IV wherein $W_1$ is

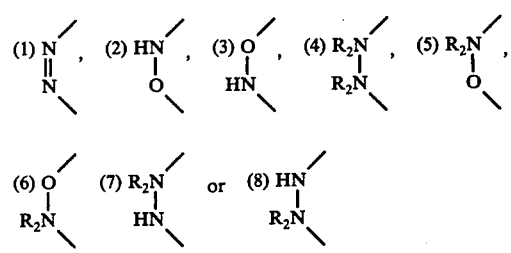

wherein $R_2$ is alkyl of one to 4 carbon atoms, inclusive or alkylcarbonyl of one to 4 carbon atoms, inclusive;
wherein $Y_1$ is (1) trans—CH=CH—CH$_2$—
(2) —(CH$_2$)$_3$—,
(3) —C≡C—CH$_2$—,
(4) trans—CH$_2$—CH=CH—, or
(5) cis—CH=C—Ch$_2$—
wherein $L_1$ is

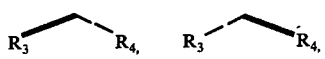

or a mixture of

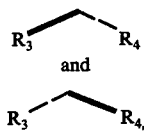

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,

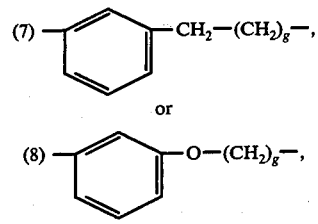

wherein $g$ is one, 2, or 3;
wherein $R_7$ is (1) —(CH$_2$)$_m$—CH$_3$,

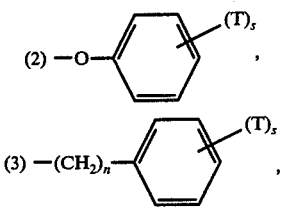

wherein $h$ is zero to 3, inclusive,
wherein $m$ is one to 5, inclusive, T is chloro, fluoro, trifluoromethyl, alkyl of one to 3 carbon atoms, inclusive, or alkoxy of one to 3 carbon atoms, inclusive and $s$ is zero, one, 2, or 3, the various T's being the same or different, with the proviso that not more than two T's are other than alkyl, with the further proviso that $R_7$ is

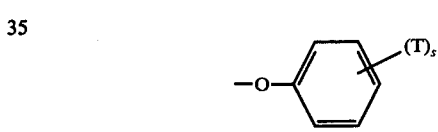

wherein T and s are as defined above, only when $R_3$ and $R_4$ are hydrogen or methyl, being the same or different;
wherein $X_1$ is
(1) —COOR$_1$ wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

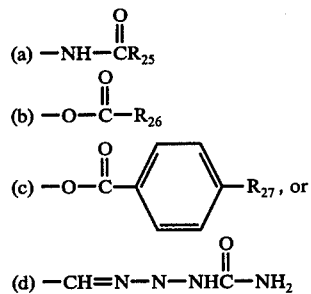

wherein $R_{25}$ is methyl, phenyl, acetamidophenyl, benzamidophenyl, or -NH$_2$; $R_{26}$ is methyl, phenyl, -NH$_2$, or methoxy; and $R_{27}$ is hydrogen or acetamido; inclusive, or a pharmacologically acceptable cation;
(2) —CH$_2$OH;
(3) —COL$_4$, wherein $L_4$ is (a) amido of the formula —NR$_{21}$R$_{22}$, wherein R$_{21}$ and R$_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy, carboxy, alkoxycarbonyl of one to 4 carbon atoms, inclusive, or nitro; carboxyalkyl of one to four carbon atoms, inclusive; carbamoylalkyl of one to four carbon atoms, inclusive; cyanoalkyl of one to four carbon atoms, inclusive; acetylalkyl of one to four carbon atoms, inclusive; benzoylalkyl of one to four carbon atoms, inclusive; benzoylalkyl substituted by one, 2, or 3 chloro, alkyl of one to 3 carbon atoms, inclusive; hydroxy, alkoxy of one to 3 carbon atoms, inclusive; carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl of one to 4 carbon atoms, inclusive; pyridylalkyl substituted by one, 2, or 3 chloro, alkyl of one to 3 carbon atoms, inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of R$_{21}$ and R$_{22}$ is other than hydrogen or alkyl;

(b) cycloamido selected from the group consisting of

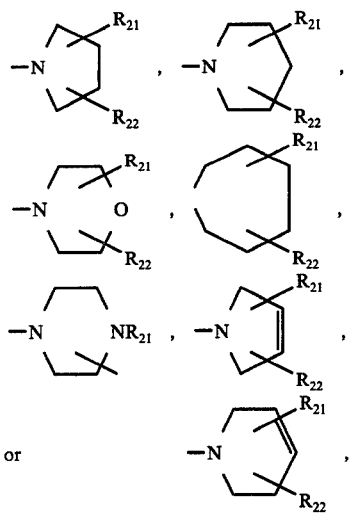

wherein R$_{21}$ and R$_{22}$ are as defined above;

(c) carbonylamido of the formula —NR$_{23}$COR$_{21}$, wherein R$_{23}$ is hydrogen or alkyl of one to 4 carbon atoms and R$_{21}$ is as defined above;

(d) sulphonylamido of the formula —NR$_{23}$SO$_2$R$_{21}$, wherein R$_{21}$ and R$_{23}$ are as defined above; or (e) hydrazino of the formula —NR$_{23}$R$_{24}$, wherein R$_{24}$ is amido of the formula —NR$_{21}$R$_{22}$, as defined above, or cycloamido, as defined above; or (4) —CH$_2$NL$_2$L$_3$, wherein L$_2$ and L$_3$ are hydrogen or alkyl of one to 4 carbon atoms, inclusive, being the same or different; and the pharmacologically acceptable acid addition salts thereof when X$_1$ is not —COOR$_1$, and R$_1$ a cation.

Those prostaglandin analogs herein wherein Z$_1$ is cis—CH=CH—CH$_2$—(CH$_2$)$_g$—CH$_2$— or cis—CH=CH—CH$_2$—(CH$_2$)$_g$—CF$_2$— are named as "PG$_2$" compounds. The latter compounds are further characterized as "2,2-difluoro" PG-type compounds. When g is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position.

Further when Z$_1$ is —(CH$_2$)$_3$—(CH$_2$)$_g$—CH$_2$— or —(CH$_2$)$_3$—(CH$_2$)$_g$—CF$_2$, wherein g is as defined above, the compounds so described are "PG$_1$" compounds. When g is 2 or 3, the "2a-homo" and "2a,2b-dihomo" compounds are described as is discussed in the preceding paragraph.

When Z$_1$ is —CH$_2$—O—CH$_2$—(CH$_2$)$_g$—CH$_2$— the compounds so described are named as "5-oxa-PG$_1$" compounds. When g is 2 or 3, the compounds so described are "2a-homo" or "2a,2b-dihomo" compounds, respectively, as discussed above.

When Z$_1$ is cis—CH$_2$—CH=CH—(CH$_2$)$_g$—CH$_2$—, wherein g is as defined above, the compounds so described are named "cis-4,5-didehydro-PG$_1$" compounds. When g is 2 or 3, the compounds so described are further characterized as "2a-homo" or "2a,2b-dihomo" compounds, respectively, as discussed above.

For the novel compounds of this invention wherein Z$_1$ is

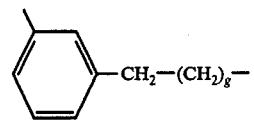

or

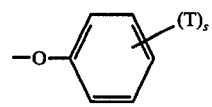

there are described, respectively, 3-oxa-3,7-inter-m-phenylene-4,5,6-trinor- or 3,7-inter-m-phenylene-4,5,6-trinor-PG-type compounds, when g is one. When g is 2 or 3, the above compounds are additionally described as "2a-homo" or "2a,2b-dihomo" PG-type compounds, respectively.

The novel prostaglandin analogs herein which contain a —(CH$_2$)$_3$—, cis—CH=CH—CH$_2$—, or —C≡C—CH$_2$— moiety as the Y$_1$ moiety, are accordingly, referred to as "13,14-dihydro," "cis-13", or "13,14-didehydro" compounds, respectively.

When Y$_1$ is trans-CH$_2$—CH=CH—, the compounds so described are named as "13,14-dihydro-trans-14,15-

wherein T and s are as defined above, only when R$_3$ and R$_4$ are hydrogen or methyl, being the same or different; compounds so described are further characterized as "2a-homo" or "2a,2b-dihomo" compounds, respectively, as discussed above.

For the novel compounds of this invention wherein $Z_1$ is

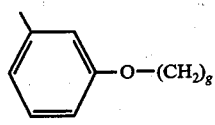

or

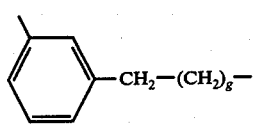

there are described, respectively, 3-oxa-3,7-inter-m-phenylene-4,5,6-trinor- or 3,7-inter-m-phenylene-4,5,6-trinor-PG-type compounds, when $g$ is one. When $g$ is 2 or 3, the above compounds are additionally described as "2a-homo" or "2a,2b-dihomo" PG-type compounds, respectively.

The novel prostaglandin analogs herein which contain a $-(CH_2)_3-$, cis$-CH=CH-CH_2-$, or $-C\equiv C-CH_2-$ moiety as the $Y_1$ moiety, are accordingly, referred to as "13,14-dihydro," "cis-13", or "13,14-didehydro" compounds, respectively.

When $Y_1$ is trans$-CH_2-CH=CH-$, the compounds so described are names as "13,14-dihydro-trans-14,15-didehydro" compounds.

When $R_7$ is $-(CH_2)_m-CH_3$, wherein $m$ is as defined above, the compounds so described are named as "19,20-dinor", "20-nor", "20-methyl" or "20-ethyl" compounds when $m$ is one, 2, 4, or 5, respectively When $R_7$ is

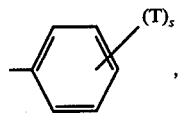, wherein T and $s$ are as defined above, and neither $R_3$ nor $R_4$ is methyl, the compounds so described are named as "16-phenyl-17,18,19,20-tetranor" compounds, when $s$ is zero. When $s$ is one, 2, or 3, the corresponding compounds are named as "16-(substituted phenyl)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenyl or 16-(substituted phenyl)-18,19,20-trinor" compounds or "16-methyl-16-phenyl- or 16-(substituted phenyl)-18,19,20-trinor" compounds, respectively.

When $R_7$ is

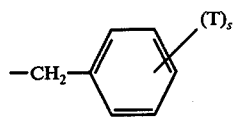

wherein T and $s$ are as defined above, the compounds so described are named as "17-phenyl-18,19,20-trinor" compounds, when $s$ is 0. When $s$ is one, 2, or 3, the corresponding compounds are named as "17-(substituted phenyl)-18,19,20-trinor" compounds.

When $R_7$ is

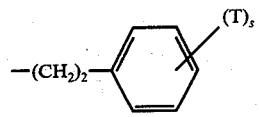

wherein T and $s$ are as defined above, the compounds so described are named as "18-phenyl-19,20-dinor" compounds, when $s$ is 0. When $s$ is one, 2, or 3, the corresponding compounds are named as "18-(substituted phenyl)-19,20-dinor" compounds.

When $R_7$ is

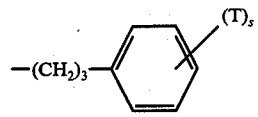

wherein T and S are as defined above, the compounds so described are named as "19-phenyl-20-nor" compounds, when $s$ is 0. When $s$ is one, 2, or 3, the corresponding compounds are named as "19-(substituted phenyl)-20-nor" compounds.

When $R_7$ is

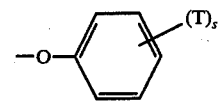

wherein T and $s$ are as defined above, and neither $R_3$ nor $R_4$ is methyl, the compounds so described are named as "16-phenoxy-17,18,19,20-tetranor" compounds, when $s$ is zero. When $s$ is one, 2, or 3, the corresponding compounds are named as "16-(substituted phenoxy)-17,18,19,20-tetra-nor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy or 16-phenyl compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is $-CH_2OH$, the compounds so described are named as "2-decarboxy-2-hydroxymethyl" compounds.

When $X_1$ is $-CH_2NL_2L_3$, the compounds so described are named as "2-decarboxy-2-aminomethyl or 2-(substituted amino)methyl" compounds.

When $X_1$ is $-COL_4$ the novel compounds herein are named as PG-type, amides. Further when $X_1$ is $-COOR$, the novel compounds herein are named as PG-type, esters and PG-type, salts where $R_1$ is not hydrogen.

Finally, the NOMENCLATURE TABLE herein describes the convention by which trivial names are further assigned for the novel compounds herein:

NOMENCLATURE TABLE

| | $W_1$ | $R_2$ | Compound Type |
|---|---|---|---|
| (1) | N=N\ | | 9,11,15-trideoxy-9α,11α-azo-PGF-type |
| (2) | HN–O\ | | 9,11,15-trideoxy-11α,9α-epoxyimino-PGF-type |
| (3) | O–HN\ | | 9,11,15-trideoxy-9α,11α-epoxyimino-PGF-type |
| (4) | $R_2N$–$R_2N$\ | alkyl | N,N'-dialkyl-9,11,15-trideoxy-9α,11α-hydrazino-PGF-type |
| | | alkyl-carbonyl | N,N'-bis(alkylcarbonyl)-9,11,15-trideoxy-9α,11α-hydrazino-PGF-type |
| (5) | $R_2N$–O\ | alkyl | N-alkyl-9,11,15-trideoxy-11α,9α-epoxyimino-PGF-type |
| | | alkyl-carbonyl | N-(alkylcarbonyl)-9,11,15-trideoxy-11α,9α-epoxyimino-PGF-type |
| (6) | O–$R_2N$\ | alkyl | N-alkyl-9,11,15-trideoxy-9α,11α-epoxyimino-PGF-type |
| | | alkyl-carbonyl | N-(alkylcarbonyl)-9,11,15-trideoxy-9α,11α-epoxyimino-PGF-type |
| (7) | $R_2N$–HN\ | alkyl | 9,11,15-trideoxy-9α,11α-alkylhydrazino-PGF-type |
| | | alkyl-carbonyl | 9,11,15-trideoxy-9α-11α-(alkylcarbonyl)hydrazino-PGF-type |
| (8) | HN–$R_2N$\ | alkyl | 9,11,15-trideoxy-11α,9α-alkylhydrazino-PGF-type |
| | | alkyl-carbonyl | 9,11,15-trideoxy-11α,9α-(alkylcarbonyl)hydrazino-PGF-type |

Examples of phenyl esters substituted in the para position (i.e. $X_1$ is —$COOR_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., $X_1$ is $COL_4$) include the following:

(1) Amides within the scope of alkylamido groups of the formula —$NR_{21}R_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamido are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Amides within the scope of aralkylamido are benzylamide, 2-phenylethylamide, 2-phenylethylamide, N-methyl-N-benzylamide, and dibenzylamide. Amides within the scope of substituted phenylamido and p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanalide, m-methylanilide, p-ethylanilide, t-butylanilide, p-carboxyanilide, p-methoxycarbonylanilide, o-carboxyanilide and o-hydroxyanilide. Amides within the scope of carboxyalkylamido are carboxyalkylamido are carboxymethylamide, carboxyethylamide, carboxypropylamide, and carboxybutylamide. Amides within the scope of the carbamoylalkylamido are carbamoylmethylamide, carbamoylethylamide, carbamoylpropylamide, and carbamoylbutylamide. Amides within the scope of cyanoalkylamido are cyanomethylamide, cyanoethylamide, cyanopropylamide, and cyanobutylamide. Amides within the scope of acetylalkylamido are acetylmethylamide, acetylethylamide, acetylpropylamide, and acetylbutylamide. Amides within the scope of benzoylalkylamido are benzoylmethylamide, benzoylethylamide, benzoylpropylamide, and benzoylbutylamide. Amides within the scope of substituted benzoylalkylamido are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butyl-benzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6- trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, t-butylbenzoylbutylamide, p-carboxybenzoylbutylamide m-methoxycarbonylbenzoylbutylamide, o-carboxybenzoylbutylamide, o-hydroxybenzoylmethylamide. Amides within the scope of pyridylamido are α-pyridylamide, β-pyridylamide, and γ-pyridylamide. Amides within the scope of substituted pyridylamido are 4-methyl-α-pyridylamide, 4-methyl-β-pyridylamide, 4-chloro-α-pyridylamide, and 4-chloro-β-pyridylamide. Amides within the scope of pyridylalkylamido are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloropyridylmethylamide, 4-chloro-β-pyridylmethylamide, 4-methyl-α-pyridylethylamide, 4-methyl-β-pyridylethylamide, 4-chloropyridylethylamide, 4-chloro-β-pyridylethylamide, 4-methyl-α-pyridylpropylamide, 4-methyl-β-pyridylpropylamide, 4-chloro-pyridylpropylamide, 4-chloro-β-pyridylpropylamide, 4-methyl-β-pyridylbutylamide, 4-methyl-α-pyridylbutylamide, 4-chloropyridylbutylamide, 4-chloro-β-pyridylbutylamide, 4-methyl-β-pyridylbutylamide. Amides within the scope of hydroxyalkyl are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxy ethylamide. Amides within the scope of dihydroxyalkylamido are dihydroxymethylamide, α,α-dihydroxyethylamide, α,β-dihydroxyethylamide, β,β-dihydroxyethylamide α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxyethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethyl-propylamide.

(2) Amides within the scope of the cycloamido groups described above are pyrrolidylamide, piperidylamide, morpholinylamide, hexamethyleneiminylamide, piperazinylamide, pyrrolinylamide, and 3,4-didehydropiperidylamide.

(3) Amides within the scope of carbonylamido of the formula —$NR_{23}COR_{21}$ are methylcarbonylamide, ethylcarbonylamide, phenylcarbonylamide, and benzylcarbonylamide. Amides within the scope of sulfonylamido of the formula —$NR_{23}SO_2R_{21}$ are methylsulfonylamide, ethylsufonylamide, phenylsulfonylamide, p-tolylsulfonylamide, benzylsulfonylamide, (4) Hydrazines within the scope of the above hydrazino groups are hdyrazine, N-aminopiperidine, benzoylhydrazine, phenylhydrazine, N-aminomorpholine, 2-hydroxyethylhydrazine, methylhydrazine, 2,2,2-hydroxyethylhydrazine and p-carboxyphenylhydrazine Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-tolyl, 4-ethyl-o-tolyl, 5-ethylm-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-, 5-, or 6-)chloro-o-tolyl, 4-chloro-2-propylphenyl, 2-isopropyl-4-chlorophenyl, 4-chloro-3,5-xylyl, (2,3- 2,4-, 2,5-, 2,6-, 3,4, or 3,5-)dichlorophenyl, 4-chloro-3-fluorophenyl, (3- or 4-)chloro-2-fluorophenyl, o-, m-, or p-trifluoromethylphenyl, (o-, m-, or p-)methoxyphenyl, (o-, m-, or p-)ethoxyphenyl, (4- or 5-)chloro-2methoxyphenyl, and 2,4-dichloro-(5-or 6-)methylphenyl.

The acid addition salts of the 2-decarboxy-2-aminomethyl- or 2-(substituted aminomethyl)-PG analogs provided by this invention. are the hydrochlorides, hydrobromides hydriodides, sulfates, phosphates, cyclohexanesulfamates, methanesulfonates, ethanesulfonates, benzenesulfonates, toluenesulfonates and the like, prepared by reacting the PG-analog with the stoichiometric amount of the acid corresponding to the pharmacologically acceptable acid addition salt.

The novel prostaglandin analogs of this invention are highly active as inhibitors of the thromboxane synthetase enzyme system. Accordingly, these novel compounds are useful for administration to mammals, including humans, whenever it is desirable medically to inhibit this enzyme system. For example, these novel compounds are useful as anti-inflammatory agents in mammals and especially humans, and for this purpose, are administered systemically and preferably orally. For oral administration, a dose range of 0.05 to 50 mg. per kg. of human body weight is used to give relief from pain associated with inflammatory disorders such as rheumatoid arthritis. They are also administered intravenously in aggravated cases of inflammation, preferably in a dose range 0.01 to 100 µg. per kg. per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

The novel prostaglandin analogs of this invention are useful in the treatment of asthma, are useful, for example, as broncodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories, parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone. Regarding use of these compounds see M. E. Rosenthale, et al., U.S. Pat. No. 3,644,638.

The novel prostaglandin analogs of this invention are useful in mammals, including man, as nasal decongestants are used for this purpose, in a dose range of about 10 µg. to about 10 mg. per ml. of a pharmacologically suitable liquid vehicle or as an aerosol spray, both for topical application.

These prostaglandins are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

When $X_1$ is —COOR$_1$, the novel PG analogs so described are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decyl-amine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereo, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galctamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

To obtain the optimum combination of biological response specificity, potency, and duration of activity, certain compounds within the scope of this invention are preferred.

It is preferred that in the 8α- side chain $g$ be either one or 3, especially one, i.e., the natural chain length of the prostaglandins. Further when the other chain contains $-(CH_2)_m-CH_3$, it is preferred that m be 3. Further, it is preferred that h, be zero or one, most preferably one. For those compounds wherein $R_7$ is

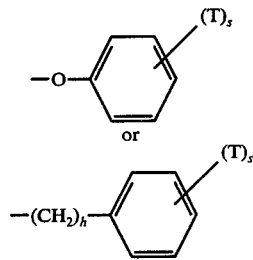

it is preferred that s be zero or one and T be chloro, fluoro, trifluoromethyl.

For those compounds wherein $R_7$ is

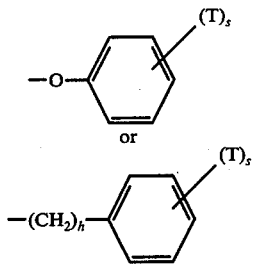

it is preferred that $R_3$ and $R_4$ both be hydrogen.

Especially preferred are those compounds which satisfy two or more of the above preferences. Further, the above preferences are expressly intended to describe the preferred compounds within the scope of any generic formula of novel prostaglandin analogs disclosed herein.

The Charts herein describe methods whereby the novel prostaglandin analogs of this invention are prepared.

With respect to the Charts $L_1$, $L_2$, $L_3$, $R_1$, $R_7$, $Z_1$, $Y_1$, $g$, $m$ and $X_1$ are as defined above, except that $R_1$ (and $X_1$ when $X_1$ is $-COOR_1$) is an ester in preference to its acid or cationic embodiments.

Further, with respect to X, certain protected derivatives thereof are preferred to in place of the primary alcohol and amine embodiments or specifically indicated in the text accompanying the charts herein.

$M_{14}$ is

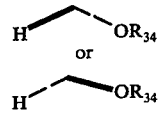

wherein $R_{34}$ is a hydroxy-hydrogen replacing group; $M_9$ is

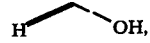

Chart A

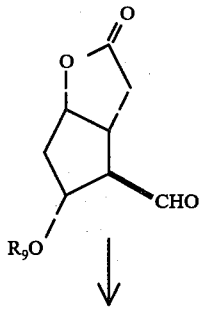

XXI

Chart A -continued
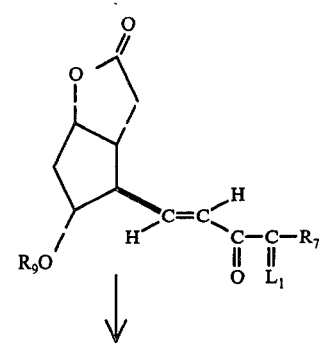
XXII
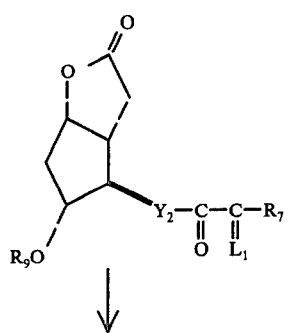
XXIII
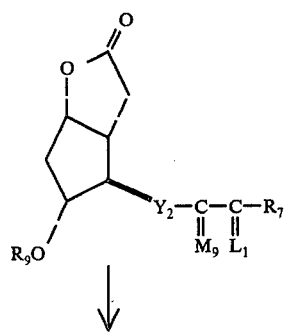
XXIV
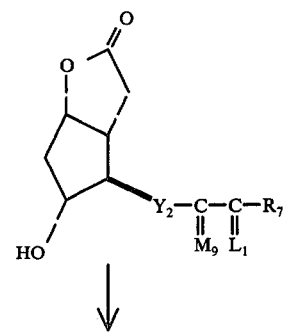
XXV
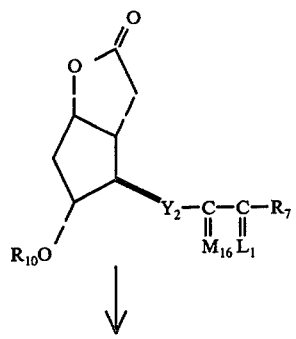
XXVI Chart A
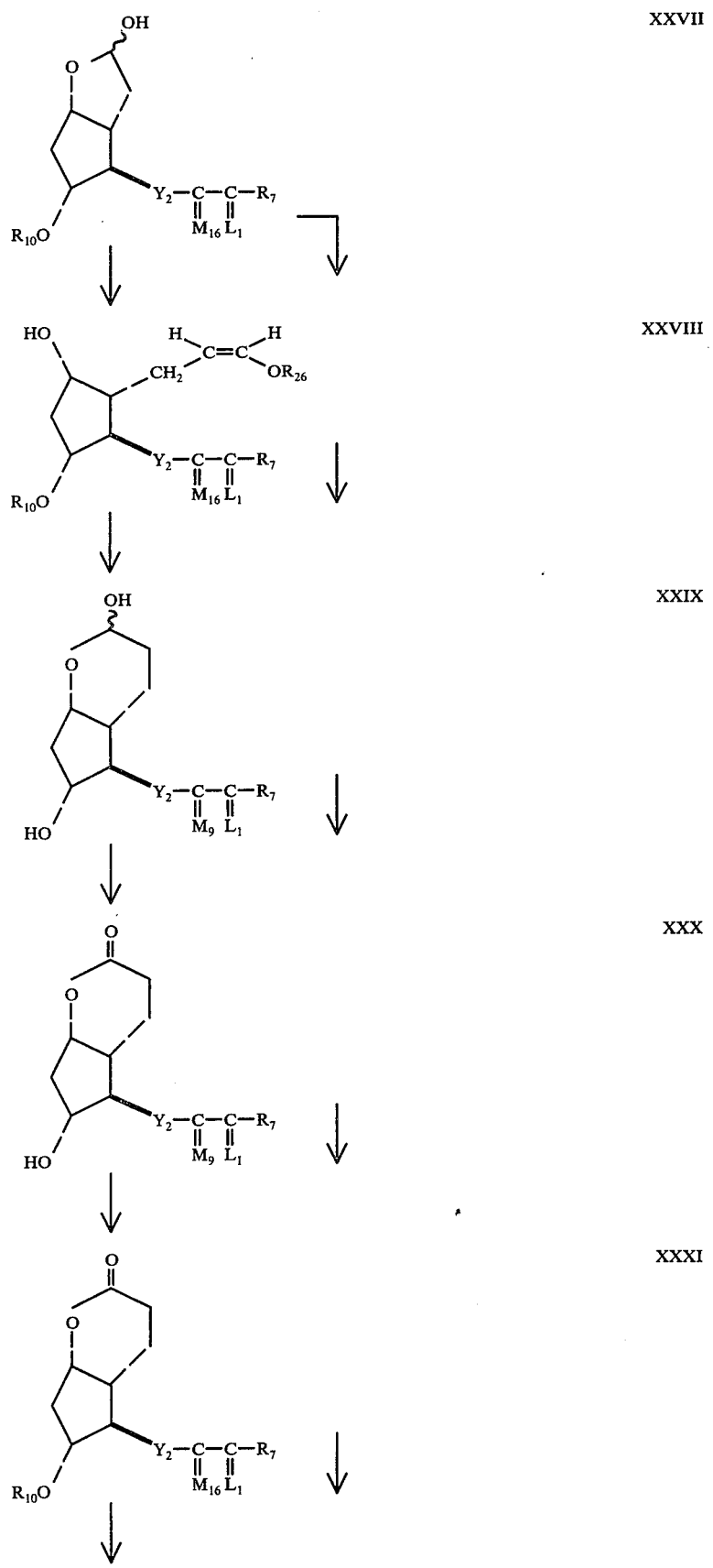
XXVII
XXVIII
XXIX
XXX
XXXI Chart A
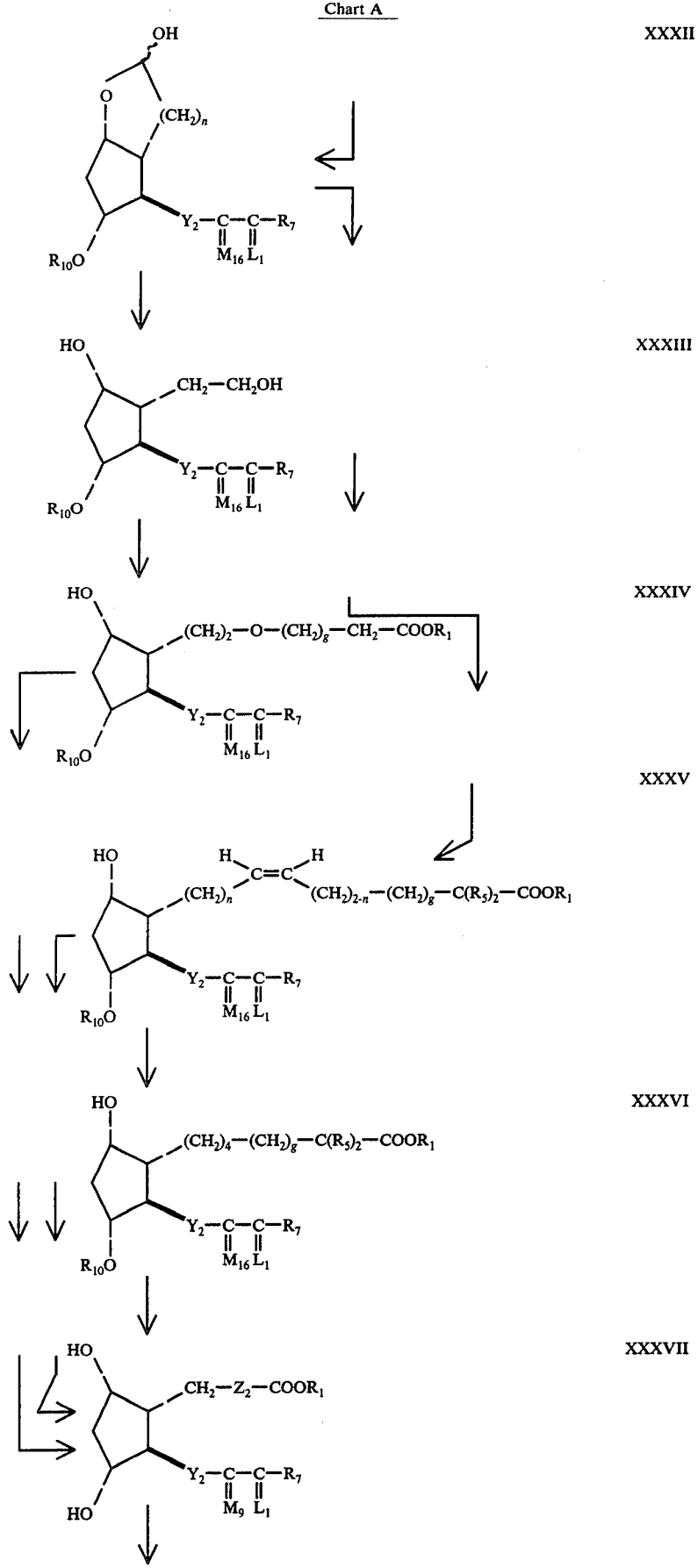

Chart A
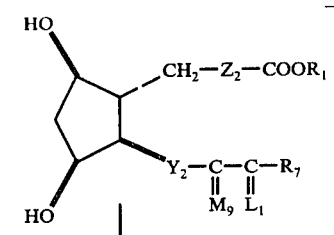
XXXVIII
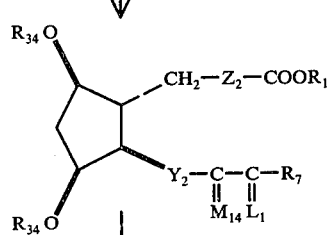
XXXIX
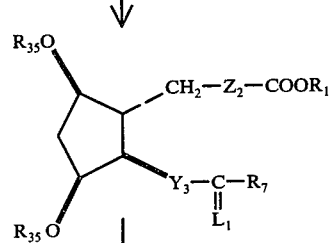
XL
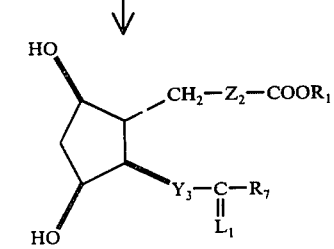
XLI
Chart B
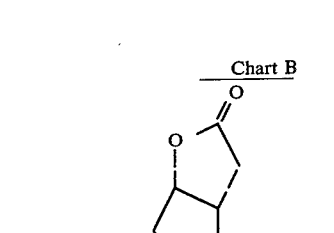
XLII
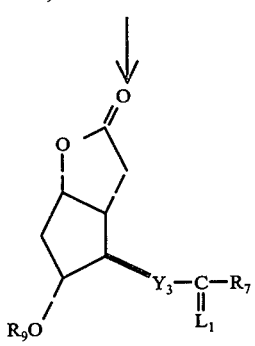
XLIII
-continued
Chart B
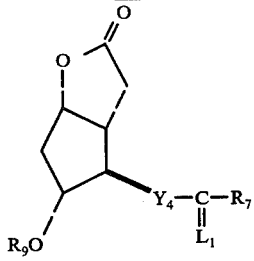
XLIV
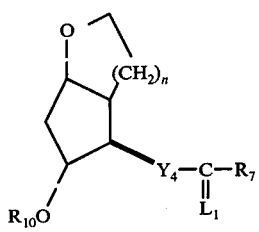
XLV -continued
Chart B
XLVI 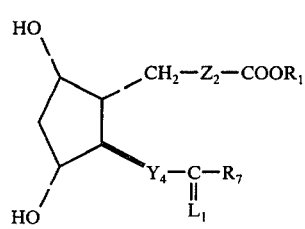
XLVII 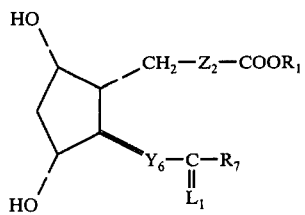
XLVIII 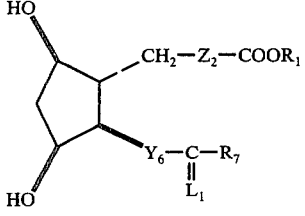
Chart C
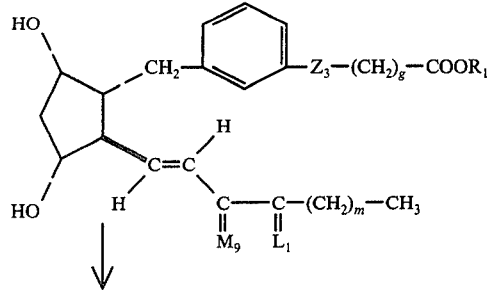
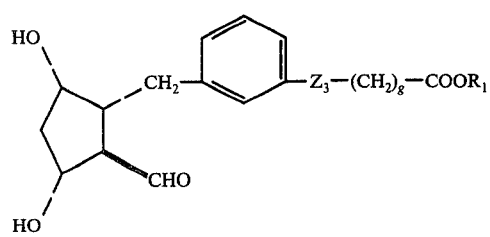
-continued
Chart C
LIII 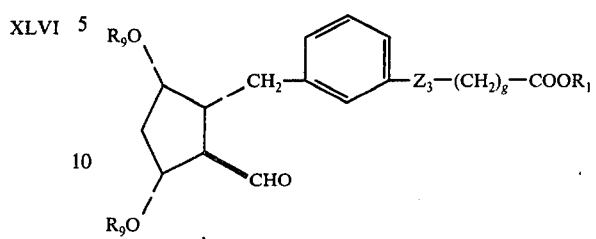
LIV 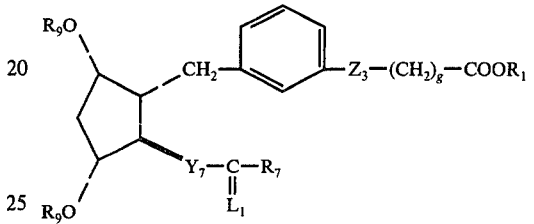
LV 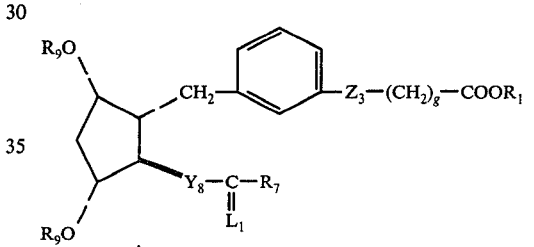
LVI 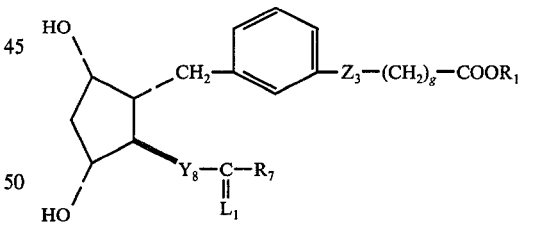
LVII 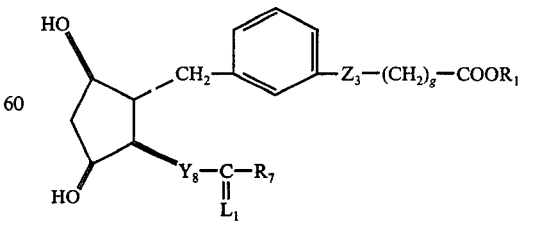

-continued
Chart C
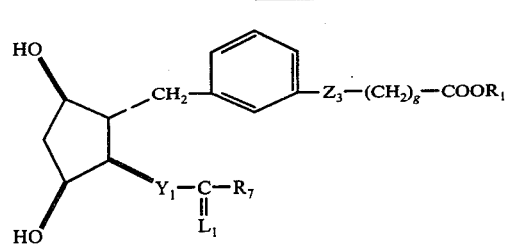
LVIII
Chart D
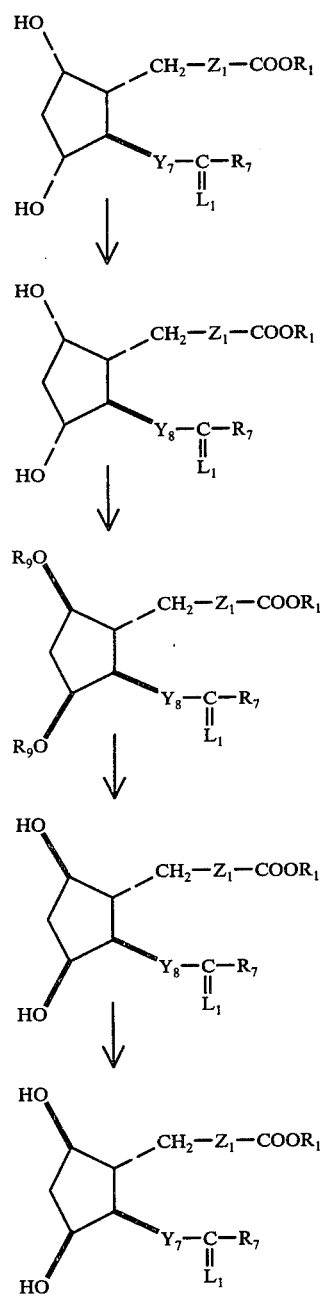
LXI
LXII
LXIII
LXIV
LXV
Chart E
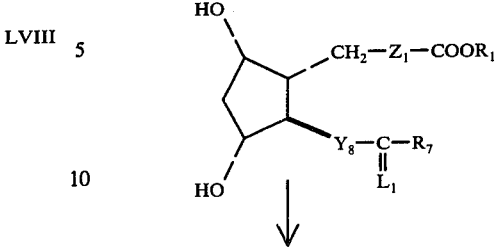
LXXI
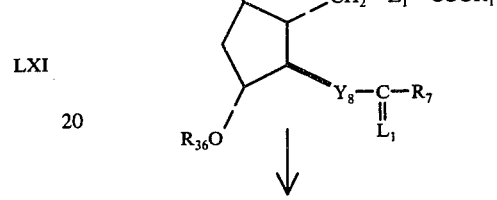
LXXII
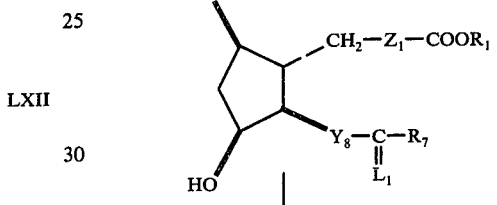
LXXIII
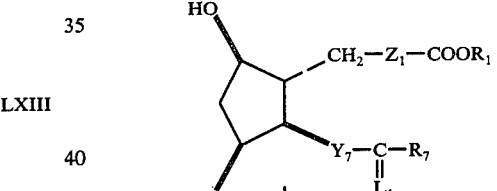
LXXIV
Chart F
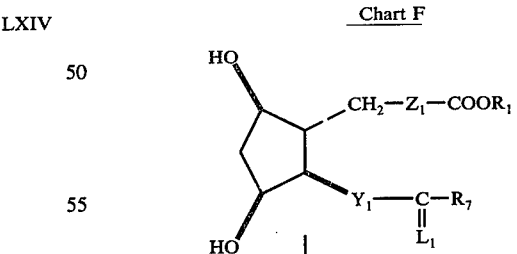
XCI
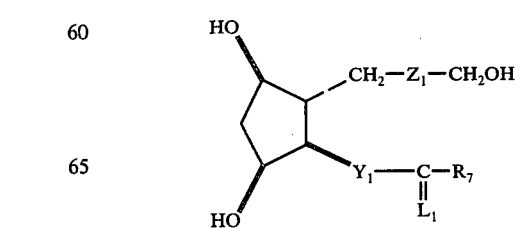
XCII

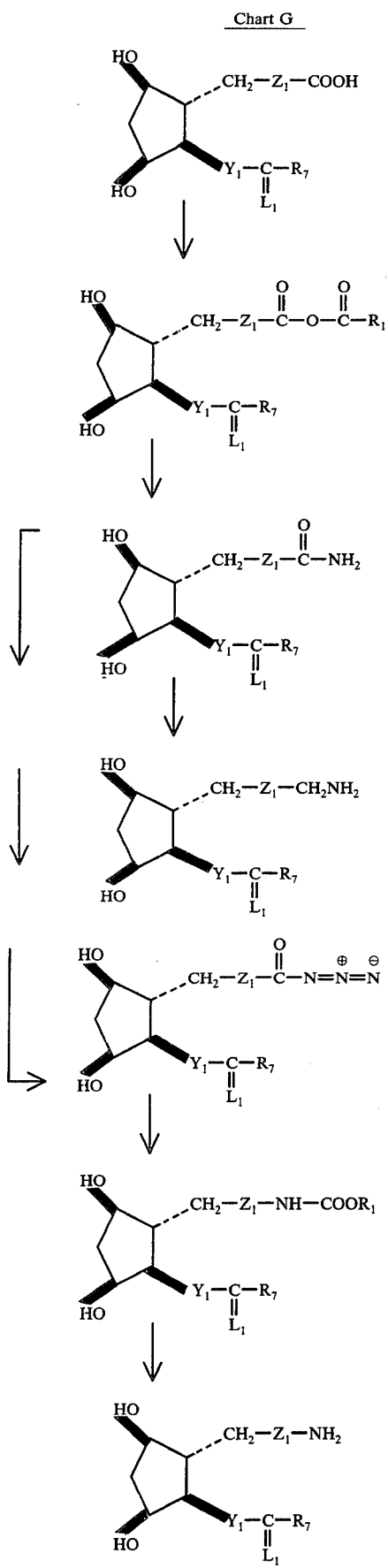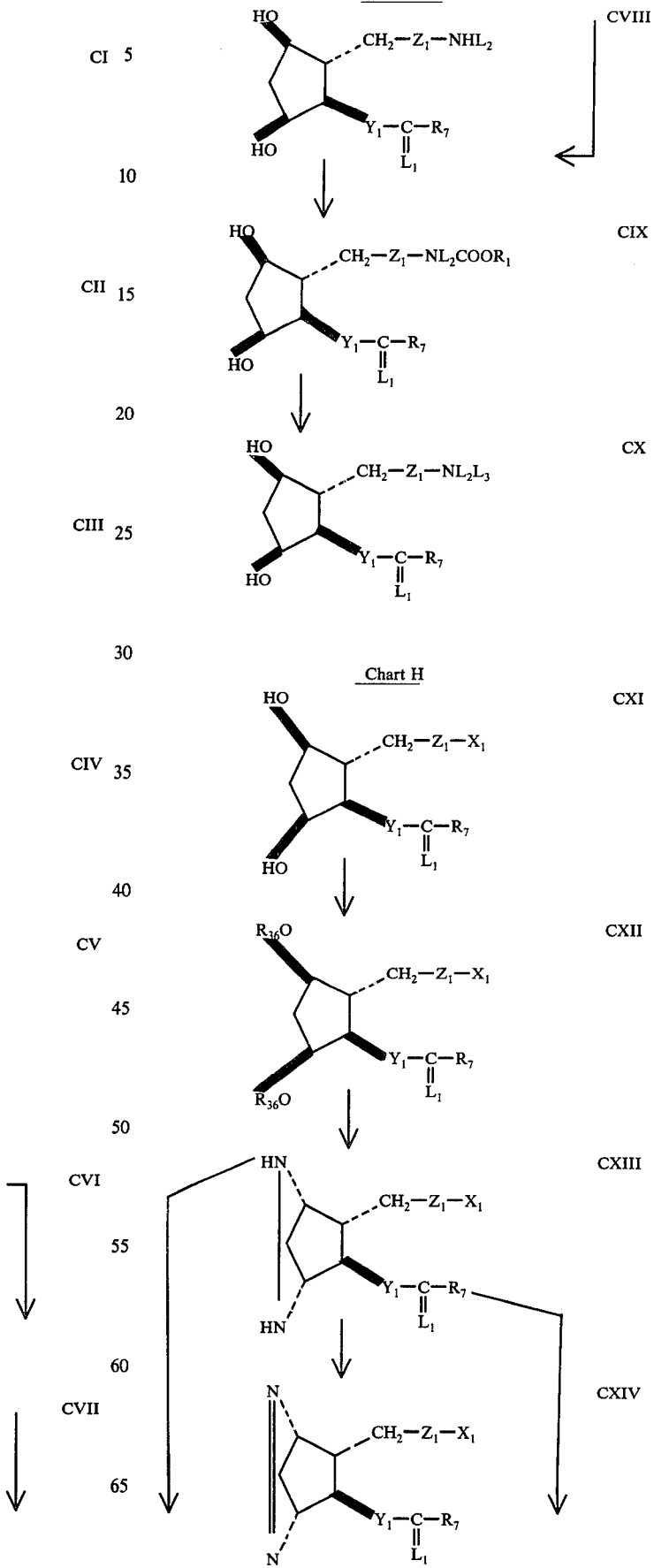

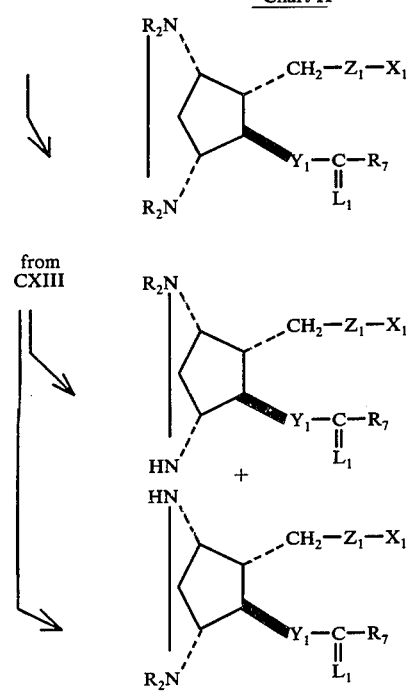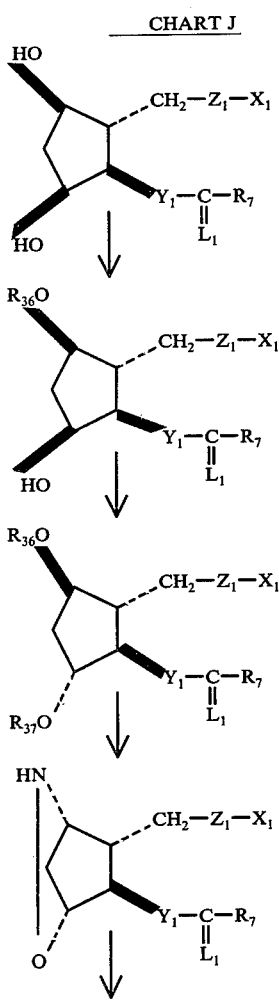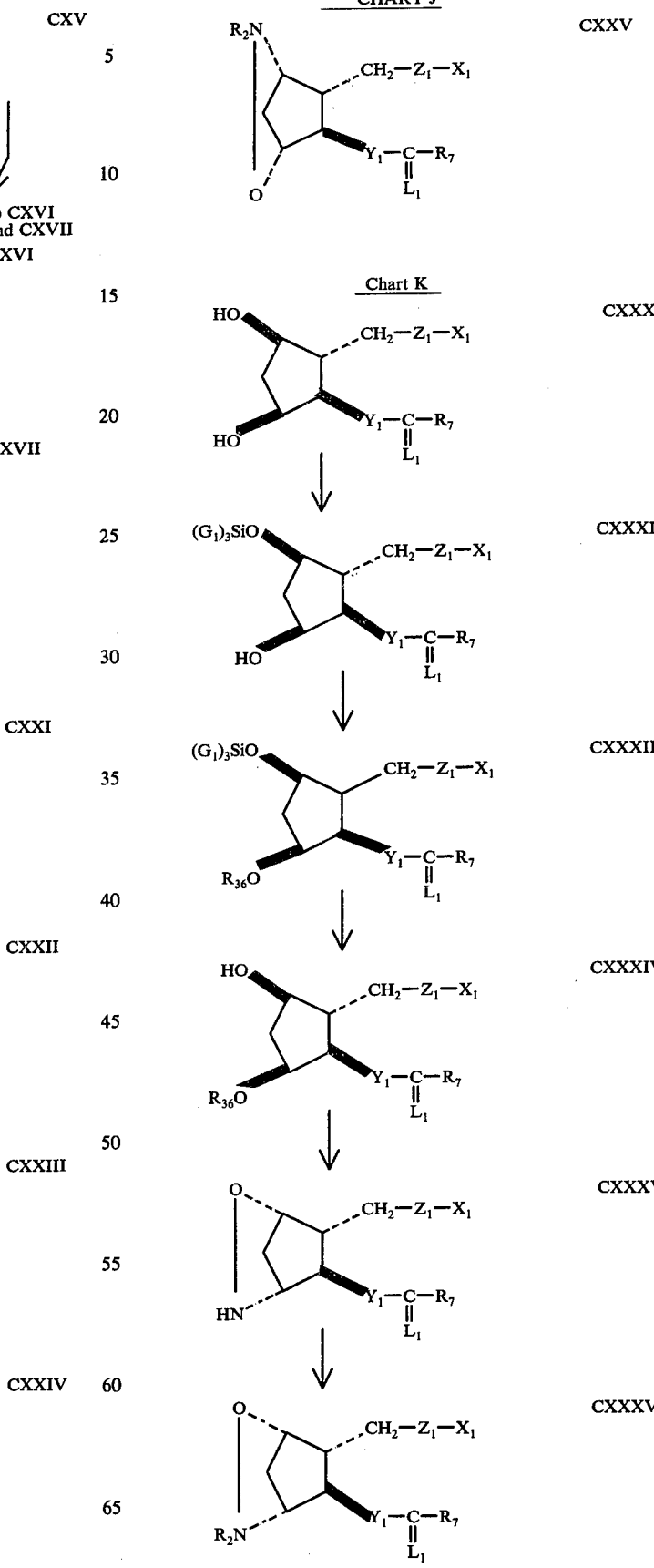

$M_{17}$ is

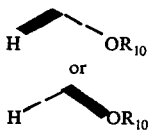

wherein $R_{10}$ is a blocking group.

$R_5$ is hydrogen or fluoro. $R_{36}$ is a non-reactive, organic radical, as hereinafter further specified, being, for example, alkyl-, aralkyl-, or arylsulfonyl. Conveniently $R_{36}$ represents the readily synthesized p-toluenesulfonyl or methylsulfonyl moiety. $R_{37}$ is N-phthalimido, e.g.,

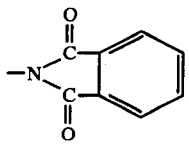

$R_{26}$ is hydrocarbyl, including alkyl, aralkyl, cycloalkyl, and the like. Examples of these hydrocarbyl groups include 2-methylbutyl, isopentyl, heptyl, octyl, nonyl, tridecyl, octadecyl, benzyl, phenethyl, p-methylphenethyl, 1-methyl-3-phenylpropyl, cycohexyl, phenyl, and p-methylphenyl.

$G_1$ is alkyl of one to 4 carbon atoms, cycloalkyl of 3 to 10 carbon atoms, inclusive, aralkyl of 7 to 12 carbon atoms, phenyl, or phenyl substituted with one or 2 fluoro, chloro, or alkyl of one to 4 carbon atoms, with the proviso that in a —Si($G_1$)$_3$ moiety the various $G_1$'s are the same or different.

$R_9$ is an acyl group. Acyl groups according to $R_9$, include:

(a) Benzoyl;

(b) Benzoyl substituted with one to 5, inclusive, alkyl of one to 4 carbon atoms, inclusive, phenylalkyl of 7 to 12 carbon atoms, inclusive, or nitro, with the proviso that not more than 2 substituents are other than alkyl and that the total number of carbon atoms in the substituents does not exceed 10 carbon atoms, with the further proviso that the substituents are the same or different;

(c) Benzoyl substituted with alkoxycarbonyl of 2 to 5 carbon atoms, inclusive;

(d) Naphthoyl;

(e) Naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fised aromatic rings does not exceed 10 carbon atoms, with the further proviso that the various substituents are the same or different;

(f) Alkanoyl of 2 to 12 carbon atoms, inclusive; or (g) formyl.

In introducing these acyl protecting groups into a hydroxy-containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxy-containing compound in the presence of a hydrogen chloride scavenger, e.g. an amine such as pyridine, triethylamine or the like. The reaction is carried out under a variety of conditions, using procedures generally known in the art. Generally mild conditions are employed: 20°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides $(R_9)_2O$), or acyl chlorides ($R_9Cl$): benzoyl; substituted benzoyl, e.g., 2-, 3-, or 4-)- methylbenzoyl, (2-, 3-, or 4-)-ethyl benzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl(2-, 3-, 4-)-toluyl, (2-, 3-, or 4-)-phenethylbenzoyl, (2-, 3-, or 4-)nitrobenzoyl, (2,4-, 2,5-, or 2,3-)dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl; 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-)ethyl-1-naphthoyl, 2-isopropyl-1-naphtholyl, 4,5-dimethyl-1-naphthoyl, (6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride isnot available, it is prepared from the corresponding acid and phosphorus pentachloride as is known in the art. It is preferred that the $R_9OH$, $(R_9)_2$), or $R_9Cl$ reactant does not have bulky hindering substituents, e.g. tert-butyl on both of the ring carbon atoms adjacent to the carbonyl attaching cite.

For the acyl groups with inversion of configuration at carbon, Chart D describes their introduction and use of such groups.

The acyl groups according to $R_9$ are removed by deacylation. Alkali metal carbonates are employed effectively at ambient temperature for this purpose. For example, potassium carbonate in methanol at about 25° C. is advantageously employed. $R_{10}$ is a blocking group. These blocking groups within the scope of $R_{10}$ are any group which replaces a hydroxy hydrogen and is neither attacked nor as reactive to the reagents used in the transformations used herein as an hydroxy is and which is subsequently replaceable with hydrogen in the preparation of the prostaglandin-type compounds. Several blocking groups are known in the art, e.g. tetrahydropyranyl. See for reference E. J. Corey, Proceedings of the Robert A. Welch Foundation Conferences on Chemical Research, 12, Organic Synthesis, pgs. 51-79 (1969). Those blocking groups which have been found useful include (a) tetrahydropyranyl;
(b) tetrahydrofuranyl; and
(c) a group of the formula

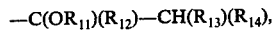

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $—(CH_2)_a—$ or $—(CH_2)_b—O—(CH_2)_c$, wherein $a$ is 3, 4, or 5, or $b$ is one, 2, or 3, and $c$ is one, 2, or 3, with the proviso that $b$ plus $c$ is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid or pyridine hydrochloride. The dihydropyran is used in large stoichometric excess, preferably 4 to 10 times the stoichiometric amount. The reaction is normally complete in several hours at 20° to 50° C.

When the blocking group is tetrahydrofuranyl, 2,3-dihydrofuran is used, as described in the preceding paragraph, in place of the 2,3-dihydropyran.

When the blocking group is

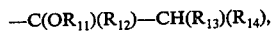

wherein $R_{11}$, $R_{12}$, $R_{13}$, and $R_{14}$ are as defined above, the appropriate reagent is a vinyl ether, e.g. isobutyl vinyl ether or any vinyl ether of the formula

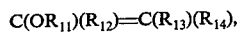

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditons for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

$R_{34}$ is a hydroxy-hydrogen replacing group which is defined herein to be acyl protecting group according to $R_9$, a blocking group according to $R_{10}$ or a silyl group within the scope of $—Si(G_1)_3$ $R_{35}$ is either an $R_{10}$ blocking group or silyl group within the scope of $—Si(G_1)_3$.

The symbol "$n$" is one or 2.

$Z_2$ is cis—$CH$=$CH$—$CH_2$—$(CH_2)_g$—$C(R_5)_2$—, cis—$CH_2$—$CH$=$CH$—$(CH_2)_g$-$CH_2$, —$(CH_2)_3$—$(CH_2)_g$—$C(R_5)_2$—, or —$CH_2$—$O$—$CH_2$—$(CH_2)_g$—$CH_2$—, wherein $R_5$ and g are as defined above. $Z_3$ is oxa or methylene.

$Y_2$ is cis—$CH$=$CH$—, or trans—$CH$=$CH$—. $Y_3$ is cis—$CH$=$CH$—$CH_2$—or trans—$CH$=$CH$—$CH_2$—. $Y_4$ is cis—$CH$=$CH$—$CH_2$—, trans—$CH$=$CH$—$CH_2$—, —$(CH_2)_3$—, or trans—$CH$=$C(Hal)$—$CH_2$—, wherein Hal is chloro, bromo, or iodo. $Y_6$ is $Y_3$ or —$(CH_2)_3$— or —$C$≡$C$—$CH_2$—. $Y_7$ is $Y_3$ or

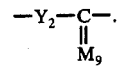

$Y_8$ is $Y_3$ or

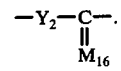

Charts A-G herein provide methods for preparing starting materials useful in the synthesis of the novel prostaglandin analogs herein. In particular, Charts A-C provide methods whereby novel 15-deoxy-11$\beta$-PGF$_\beta$ compounds are prepared. Charts D and E describe methods for diepimerization of PGF$_{2\alpha}$ compounds to the corresponding 11$\beta$ PGF$_{2\beta}$ compounds. Charts F and G provide methods whereby the C-1 carboxylic acids prepared in the preceeding Charts are transformed to corresponding C-1 alcohols and C-1 primary, secondary, or tertiary amines, respectively.

With respect to Chart A, a method is provided whereby the formula XXI bicyclic lactone aldehyde, known in the art in either optically active or racemic form, is transformed to the formula XLI 15-deoxy-11$\beta$-PGF$_{62}$ compounds.

The formula XXII compound is prepared from the formula XXI compound by a Wittig oxoalkylation. Reagents known in the art or prepared by methods known in the art are employed. The transenone lactone is obtained stereospecifically. See for reference D. H. Wadworth, et al., Journal of Organic Chemistry 30, 680 (1965).

In the preparation of the formula XXII compound, certain phosphonates are employed in the Wittig reaction. These phosphonates are of the general formula

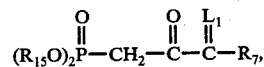

wherein $L_1$ and $R_7$ are as defined above and $R_{15}$ is alkyl of one to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methylphosphonate as produced using n-butyllithium. For this purpose, acids of the general formula

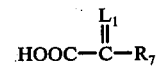

are employed in the form of their lower alkyl esters, preferably methyl or ethyl. The methyl esters for example are readily obtained by reaction of the corresponding acids with diazomethane.

For example, when $R_7$ is

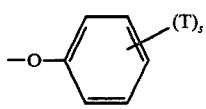

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o, m-, or p-)ethylphenoxy-, 4-ethyl-o-tolyoxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substitued phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl- 2-phenoxy- or (2-substituted)phenoxypropionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_7$ is: phenoxy-, (o-, m-, or p-)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the (T)$_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is phenyl, benzyl, phenylallyl or substituted phenyl, benzyl, or phenylallyl.

For example, when $R_3$ and $R_4$ of the $L_1$ moiety are both hydrogen and h is one there are available the following phenyl or substituted phenyl propionic acids: (o-, m-, or p-)chlorophenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl and h is one there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)-difluorophenyl-, 2,3-dimethylphenyl-, and (2,3-, 3,4-, or 4,5-)dimethoxyphenyl-.

When both $R_3$ and $R_4$ are methyl and h is one there are available, for example, the following 2,2-dimethyl-3-phenyl or substituted phenyl propionic acids: phenyl- and p-methylphenyl.

When one and only one of $R_3$ and $R_4$ is fluoro and h is one there is available, for example, 2-fluoro-3-phenyl propionic acid.

Phenyl substituted acids (as above wherein $R_7$ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted phenylallyl or benzyl chloride. Thus, the above acid is obtained by the following reaction (when h is not zero):

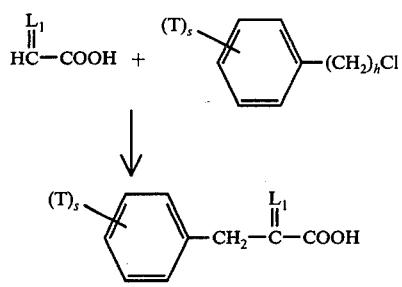

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when one of the $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxo-alkanoic acids, i.e. butyric, pentanoic, hexanoic, heptanoic, and octanoic. The transformation of these 2-oxo-alkanoic acids to the corresponding 2,2-difluoro alkanoic acids proceeds by methods known in the art, using known ketonic fluorinating reagents. For example, $MoF_6 \cdot BF_3$ is advantageously employed in the fluorination. See Mathey, et al., Tetrahedron Lett. 27, 2965 (1971).

The formula XXIII compound in prepared from the formula XXII compound by optional photoisomerization when $Y_2$ is —CH=CH—, followed by separating the resulting trans-cis mixture of isomers. The photoisomerization proceeds by use of a conventional photon generating source which is capable of producing photons whose wavelength is between about 2800 to 4000 Angstroms. It is preferred to use a conventional photon generating source which is capable of producing photons whose wave length is about 3500 Angstroms. Irradiation continues until an equilibrium mixture of cis and trans isomers is obtained. The progress of the photoisomerization is conveniently monitored by conventional methods, e.g. silica gel thin layer chromatography (TLC). The resulting equilibrium mixture is then separated using conventional methods. For example, silica gel chromatography is advantageously employed.

The formula XXIV compound is prepared from the formula XXIII 3-oxo bicyclic lactone by transformation of the 3-oxo-moiety to the $M_9$ moiety.

The above 3-oxo bicyclic lactone is transformed to the corresponding $3\alpha$ or $3\beta$-hydroxy bicyclic lactone wherein $M_9$ is

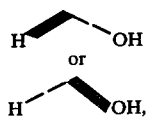

by reduction of the 3-oxo moiety, followed by separation of the $3\alpha$- and $3\beta$-hydroxy epimers. For this reduction the known ketonic carbonyl reducing agents which do not reduce ester or acid groups or carbon-carbon double bonds (when such reduction is undesirale) are employed. Examples of these agents are the metal borohydrides, especially sodium, potassium, and zinc borohydrides, lithium(tri-tert-butoxy)-aluminum hydride, metal trialkyl borohydrides, e.g. sodium trimethoxy borohydride, lithium borohydride, and the like. In those cases in which carbon-carbon double bonds are not present, the boranes, e.g. disiamylborane (bis-3-methyl-2-butyl borane) are alternatively employed.

For the production of either C-15 epimerically pure product, the 15-epi compound is separated from the mixture by methods known in the art. For example, silica gel chromatography is advantageously employed.

The formula XXV compound is prepared from the formula XXIV compound by deacylation, as described above. The formula XXVI compound is then prepared from the formula XXV compound by replacing any free hydroxy moieties with blocking groups according to $R_{10}$ by the procedure described above. The formula XXVII compound is then prepared from the formula XXVI compound by reduction of the formula XXVI lactone to a lactol. Methods known in the art are employed. For example, diisobutylaluminum hydride is employed at $-60$ to $-70°$ C.

The formula XXVII compound undergoes condensation to form the formula XXVIII enol ether. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below $-10°$ C. The formula XXVII lactol is mixed with the above reagent and the condensation proceeds smoothly within the temperature range of $-30°$ C. to $+30°$ C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxy- methylenetriphenylphosphorane. Various hydrocarbyloxymethylenetriphenylphosphoranes which are optionally substituted for the alkoxymethylenetriphenylphosphoranes and are accordingly useful for preparing the formula XXVII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecylethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346-348, John Wiley and Sons, New York, New York, (1965). The formula XXVIII enol intermediates are then hydrolyzed to the formula XXIX lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXX compound is then prepared from the formula XXIX compound by oxidation of the formula XXIX lactol to a lactone. This transformation is carried out, using for example, silver oxide as an oxidizing reagent, and is followed by treatment with pyridine hydrochloride. Preparation of the formula XXXI compound proceeds from the formula XXX compound by transformation of any free hydroxy moieties to blocking groups according to $R_{10}$, following the procedures herein described for such a transformation.

Thereafter the formula XXXII compound (wherein n is 2) is prepared from the formula XXXI compound by reduction of the formula XXXI lactone to a lactol. For example, diisobutylaluminum hydride is employed as is described above for the reduction of lactones to lactols. The formula XXXII lactol is alternately represented by the formula XXVII compound when n is one.

The formula XXXV compound is prepared from the formula XXXII compound by a Wittig carboxyalkylation, using the appropriate ($\omega$-carboxyalkyl)triphenylphosphonium bromide with sodio dimethyl sulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXV cis-4,5-didehydro-PGF$_{1\alpha}$- or PGF$_{2\alpha}$-type compound.

The formula XXXVI compound is then prepared from the formula XXXV compound by catalytic hydrogenation of the formula XXXV compound. Methods known in the art for transformation of PG$_2$-type compounds to PG$_1$-type compounds are employed. Accordingly, metal catalysts (e.g. palladium) on a suitable support (e.g. carbon) at about 0° C. are employed under a hydrogen atmosphere. See for reference B. Samuelsson, Journal of Biological Chemistry, 239, 491 (1974).

The formula XXXII lactol is transformed into the corresponding formula XXXIV 5-oxa-PGF$_{1\alpha}$-type intermediate first by reduction of the formula XXXII lactol, for example, with aqueous methanolic or ethanolic sodium borohydride to the formula XXXIII compound. Alternatively, and preferably, the formula XXXIII compound is obtained by a one step reduction of the formula XXVI lactone, for example, with lithium aluminum hydride or diisobutyl aluminum hydride at a temperature ranging from 0° to 35° C.

For preparing the formula XXXIV compound, a Williamson synthesis is employed. For example, the formula XXXIII compound is condensed with a haloalkanoate within the scope of $$Hal-(CH_2)_g-CH_2-COOR_1,$$

wherein Hal is chloro, bromo, or iodo and g is as defined above. Normally the reaction is done in the presence of a base such as n-butyllithium, phenyllithium, trimethyllithium, sodium hydride, or potassium t-butoxide.

Alternatively and preferably, an ortho-CH—CH is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at $-20°$ to $50°$ C., but is preferably performed at ambient temperature. Following the condensation, the formula XXXIV compound is obtained by methods known in the art, for example, by hydrolysis in cold dilute mineral acid.

The formula XXXVII compound is then prepared from the formula XXXIV, XXXV, or XXXVI compound by first hydrolyzing any blocking groups according to $R_{10}$ and thereafter optionally separating any mixed C-15 epimers (i.e., when such separation has not heretofore been undertaken). Acidic conditions are employed in the hydrolysis as is described above.

The formula XXXVIII compound is then prepared from the formula XXXVII compound by a 9,11-diepimerization. Accordingly, by this transformation the $9\alpha$ and $11\alpha$ hydroxyls are converted to the $9\beta$ and $11\beta$ configuration as in the formula XXXVIII compound. Methods by which this 9,11-diepimerization are achieved are known in the art, and described in Charts D and E, hereinafter.

The formula XXXVIII tri-secondary hydroxyl compounds are then transformed to the corresponding formula XXXIX triacylate or tris-ethers by replacing each of the secondary hydroxyls of the formula XXXVIII compound with the hydroxy hydrogen replacing group according to $R_{34}$. Methods for the introduction of these hydroxy hydrogen replacing groups according to $R_{34}$ are described above.

The formula XL compound is then prepared from the formula XXXIX compound by a reductive allylic deoxygenation. By this transformation the oxygen attached to the C-15 of formula XXXIX compound is replaced by hydrogen. Further, when the formula XXXIX compound is a 9,11-diacylate, the present transformation hydrolyzes these C-9 and C-11 acyl moieties, yielding a formula XLI 9,11-dihydroxy product.

The present transformation is accomplished employing the formula XXXIX free acid, or, if a C-1 alcohol corresponding to the formula XL carboxylic acid is desired, then a formula XXXIX C-1 lower alkyl ester ($R_1$ is lower alkyl) is employed. When the formula XXXIX compound is an ester, and the preparation of the corresponding acid is desired, then saponification methods hereinbelow described are employed.

The allylic deoxygenation proceeds by dissolving the $11\beta$-$PGF_\beta$ compound in ammonia or a primary (lower alkyl)amine solvent with an ether-containing organic cosolvent such as tetrahydrofuran, diethyl ether, or dioxane. To the reaction mixture is added an alkali metal or an alkaline earth metal, being lithium, sodium, potassium, calcium, or magnesium (in order of their preference for accomplishing the present purpose). Finally, a proton source is provided, being selected from the lower alkanols, preferably ethanol, t-butanol, or neopenyl alcohol, or trace amounts of water.

The reaction then proceeds to completion at low temperature, preferably between $-78°$ C. and $0°$ C.

Finally, the formula XLI compound is prepared from the formula XL compound by an optional hydrolysis of the blocking groups, employing methods described above.

Chart B provides a method whereby the formula XLII bicyclic lactone aldehyde is transformed to the corresponding formula XLVIII 15-deoxy-$11\beta$-$PGF_\beta$ compound.

The formula XLII compound is first transformed to the formula XLIII compound, employing a Wittig alkylation.

In this Wittig alkylation there are employed phosphonamides of the formula

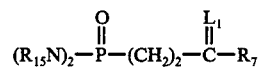

or thiophosphonates, as follows:

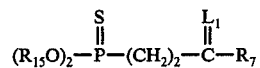

wherein $R_{15}$ is as defined above. These phosphorus-containing compounds are employed in the Wittig alkylation by methods described in Chart A for the Wittig alkylation. However, there are employed higher temperatures in order to secure ease of elimination.

Further, these phosphorus containing compounds are known in the art or prepared by methods known in the art.

For example, N,N-dialkyl-methylphosphoramide is reacted with n-butyllithium and a primary alkyl or aralkyl halide of the formula

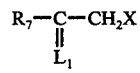

wherein Y is chloro, bromo, or iodo, yielding the above N,N-dialkylphosphoramides. Further, the preparation of the above dialkyl thiophosphonates proceeds by reaction of a dialkyl methyl thiophosphonate with n-butyl lithium and the above alkyl or aralkyl halides. For a discussion of the synthetic routes, see Corey, et al., J.A.C.S. 88:5654–5657 (three publications).

The formula XLIII compound is obtained as a mixture of cis and trans unsaturated stereoisomers. This stereoisomeric mixture is readily separated by conventional (e.g. chromatographic) techniques.

The formula XLIII compound is then transformed to the formula XLIV compound by optional saturation or monohalogenation (i.e. at the latent C-14 position of the formula XLVIII product.)

When the saturated formula XLIV compound is to be prepared, catalytic hydrogenation techniques as described in the transformation of the formula XXXV compound to the formula XXXVI compound of Chart A, are employed.

The formula XLIV compound wherein $Y_4$ is trans-CH=C(Hal)—CH$_2$— is prepared from the formula XLIII compound by dihalogenation, followed by dehydrohalogenation. The halogenation proceeds by methods known in the art. The reaction proceeds slowly to completion, ordinarily within three to ten days when the molecular form of the halide (Hal)$_2$ in a diluent (e.g., carbon tetrachloride or a mixture of acetic acid and sodium acetate) is employed in this dihalogenation. Thereafter dehydrohalogenation proceeds by addition of an organic base, preferably amine base, to the halide. For example pyridine, or a diazobicycloalkene, is an especially useful amine base, although non-amine bases such as methanolic sodium acetate are likewise employed.

In any event, the chloro rather than bromo or iodo intermediates are preferred formula XLIV products, in that they lead to formula XLVI PG intermediates which are more easily dehydrohalogenated at C-13 and C-14, according to the procedures hereinafter described.

In each of the above described methods for the preparation of the formula XLIV compound wherein $Y_4$ is trans-CH=C(Hal)—CH$_2$— the desired formula XLIII product is often contaminated with its corresponding cis isomer and corresponding 13-halo isomers. In performing the below steps it is particularly desirable to obtain pure formula XLIV product in order to avoid creation of complicated mixtures of stereoisomers. Accordingly, the formula XLIV compound is subjected to conventional separation techniques (e.g. chromatography) to obtain pure product.

The formula XLV compound is then prepared from the formula XLIV compound, following the general procedure described in Chart A in preparation of the formula XXXII compound from the formula XXIV compound. Thereafter, this formula XLV compound is transformed to the corresponding formula XLVI compound, following the procedures of Chart A for the preparation of the formula XXXVII compound from the formula XXXII compound.

This formula XLVI compound is then optionally dehydrohalogenated, preparing the formula XLVII compound. The preferred method for this dehydrohalogenation proceeds using, as a reaction diluent, a mixture of dimethylsulfoxide (or a similar aprotic solvent) and methanol (between 5:1 and 10:1 by volume). Thereafter a strong organic base, for example, potassium, t-butoxide, or sodium methoxide is added and the reaction is allowed to proceed to completion at or below ambient temperature (0°-25° C.) The reaction is ordinarily complete within 24 hr.

The formula XLVII compound is then 9,11-diepimerized, yielding the formula XLVIII 15-deoxy-11$\beta$-PGF$_\beta$ compounds. This 9,11-diepimerization, as discussed in Chart A, proceeds by the methods hereinafter described (in Charts D and E).

Chart C provides a method whereby the formula LI 3,7-inter-m-phenylene- or 3,7-inter-m-phenylene-3-oxa-PGF$_\alpha$-type compound is transformed to corresponding formula LVII 15-deoxy-9$\beta$-PGF$_\beta$ compounds. The compounds according to formula LI which are employed as starting material for Chart C are known in the art or readily available by methods known in the art. For example, see U.S. Pat. 3,933,900, particularly Chart L therein which describes the preparation of 3,7-inter-m-phenylene-3-oxa-4,5,6-trinor-PGF$_{2\alpha}$-type compounds.

With respect to Chart C, the formula LII compound is prepared from the formula LI compound by cleavage of the 13,14-trans double bond, convenient by ozonolysis. Ozonolysis proceeds by bubbling dry oxygen, containing about 3 percent ozone, through a mixture of a formula LI compound in a suitable nonreactive diluent. For example, n-hexane is advantageously employed. The ozone may be generated using methods known in the art. See, for example, Fieser, et al., "Reagents for Organic Synthesis," John Wiley and Sons, Inc. (1967), pages 773–777. Reaction conditions are maintained until the reaction is shown to be complete, for example, by silica gel thin layer chromatography or when the reaction mixture no longer rapidly decolorizes a dilute solution of bromine in acetic acid.

The formula LIII compound is prepared from the formula LII compound by acylation, employing methods described above for introducing acyl protecting groups according to R$_9$.

Thereafter the formula LIV and formula LV compounds are successively prepared from the formula LIII compound, employing the methods described above in Chart A and B. Thus, for example, the method described in Chart B for the transformation of the formula XLII compound to the formula XLIII and formula XLIV compounds, respectively are employed.

Thereafter the formula LV compound is transformed to the formula LVI compound by deacylation. Deacylation proceeds by the methods described above for the removal of acyl protecting groups according to R$_9$.

The formula LVI compound is then transformed to the formula LVII compound by a 9,11-diepimerization. Methods described in Charts D and E hereinafter are employed in this transformation.

Finally, the formula LVIII compound is prepared from the formula LVII compound by optional 15-deoxygenation and optional dehydrohalogenation, as described above in Charts A and B, respectively.

As indicated above Chart D provides a method whereby each of the various PGF$_\alpha$ or 15-deoxy-PGF$_\alpha$-type compounds herein (formula LXI) are transformed to corresponding formula LXV 11$\beta$-PGF$_\beta$- or 15-deoxy-11$\beta$-PGF$_\beta$-type compounds.

The formula LXI 15-hydroxy compound is transformed to the corresponding formula LXII compound by selective C-15 etherification with an R$_{10}$ blocking group. Selectivity of this reaction can be assured by first forming a cyclic boronate of the formula LXI 15-hydroxy compound with a slight stoichometric excess of the corresponding n-butyl-boronic acid. In a suitable organic diluent (e.g. methylene chloride) this transformation proceeds rapidly to completion. Thereupon, the 15-hydroxyl is etherified with R$_{10}$ blocking groups, following the procedures hereinabove described. Finally, the formula LXII compound is prepared by hydrolyzing the boronate, employing an alkaline metal hydroxide (e.g. sodium, lithium, or potassium hydroxide) in water and a water-miscible diluent capable of yielding a homogeneous reaction mixture (e.g. methanol THF, or ethanol) in the presence of dilute aqueous reaction peroxide.

The formula LXII compound is then 9,11-diepimerized to the formula LXIII compound. This diepimerization proceeds by the method described by J. E. Herz, et al., J. C. S. Perkin, I, 1438 (1974). Accordingly, the formula LXII compound is reacted with triphenylphosphine, a carboxylic acid ($R_9OH$), in a di(loweralkyl)azodicarboxylate, in an organic diluent (e.g. tetrahydrofuran). The reaction proceeds to completion at ambient temperature, ordinarily within 24 hr. For the above purposes, the suitable carboxylic acids are those which yield acyl residues according to $R_9$.

The formula LXIII 9,11-diacylate thusly produced is then deacylated by methods hereinabove described, yielding the formula LXIV compound. This formula LXIV compound wherein $Y_8$ represents an ether containing moiety, is then transformed to the formula LXV compound by hydrolysis of the $R_{10}$ blocking groups. Methods hereinabove described are employed.

Alternatively, the procedure of Chart D is modified by the elimination of the introduction and subsequent hydrolysis of the $R_{10}$ blocking groups. According to this modified procedure Chart D accomplishes the diepimerization by a two-step transformation (i.e. LXII to LXIII, and thereafter to LXIV).

Chart E provides a further method whereby the present 9,11-diepimerization is achieved.

By the method of this Chart the formula LXXI compound is 9,11-(alkyl or aryl)sulfonated, yielding the formula LXXII compound. This alkyl or aryl sulfonization proceeds by reaction of the corresponding alkyl or aryl sulfonyl chloride with the formula LXXI compound in amine solvents, especially pyridine.

Thus, p-toluenesulfonyl chloride and methylsulfonyl chloride yield, respectively, the formula LXXII bis-tosylates or bis-mesylates.

Thereafter the formula LXXII compound is diepimerized to the formula LXXIII compound by procedures described in R. Baker, et al., Journal of the Chemical Society (C), 1605 (1965) or E. J. Corey, et al., Chemical Communication 16:658 (1975).

By the first of these methods the formula LXII sulfonate is reacted with tetra-n-butyl ammonium acetate, followed by treatment with a deacylating agent (e.g. potassium methoxide in methanol).

Finally, the formula LXXIII compound is transformed to the formula LXXIV compound by hydrolysis of the optionally present $R_{10}$ blocking group.

Chart F provides a method whereby the formula XCI compound prepared according to Charts D and E is transformed to the formula XCII 2-decarboxy-2-hydroxymethyl compound. This transformation proceeds by methods known in the art for reducing prostaglandins to corresponding primary alcohols. Thus, for example, when the formula XCI compound is an acid or ester, the reduction proceeds with lithium aluminium hydride or diisobutyl aluminum hydride.

Useful reaction diluents include diethyl ether, tetrahydrofuran, dimethoxyethane, or like organic solvents. The reaction mixture is conveniently carried out temperatures of about $-78$ to $100°$ C., although preferably at about $0°$–$25°$ C.

When the formula XCI compound is an acid, reducing agents such as diborane are also employed, when double bond reduction is not a problem.

Chart G provides a method whereby the formula CI compound, prepared above, is transformed to the various 2-decarboxy-2-aminomethyl or 2-decarboxy-2-(substituted amino)methyl-15-deoxy-9$\beta$-PGF$_\beta$-type compounds of formulas CIV, CVI, CVII, CVIII, CIX, or CX.

By the procedure of Chart G the formula CI compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type amide or formula CV PG-type, azide.

For preparation of the 15-deoxy-11$\beta$-PGF$_\beta$-type, amide (formula CIII) the formula CII mixed acid anhydride is reacted with liquid ammonia or ammonium hydroxide.

Alternatively, the formula CIII compound is prepared from the formula CI free acid by methods known in the art for transformation of carboxy acids to corresponding carboxyamides. For example, the free acid is transformed to a corresponding methyl ester (employing methods known in the art; e.g., excess ethereal diazomethane), and a methyl ester thus prepared is transformed to the formula CIII amide employing the methods described for the transformation of the formula CII mixed acid anhydride to the formula CIII amide.

Thereafter the formula CIV 2-decarboxy-2-aminomethyl-15-deoxy-11$\beta$-PGF$_\beta$-type compound is prepared from the formula CIII compound by carbonyl reduction. Methods known in the art are employed in this transformation. For example, lithium aluminum hydride is conveniently employed.

The formula CII compound is alternatively used to prepare the formula CV azide. This reaction is conveniently carried out employing sodium azide by methods known in the art. See for example, Fieser and Fieser, Reagents for Organic Synthesis vol. 1, pgs. 1041-1043, wherein reagents and reaction conditions for the azide formation are discussed.

Finally, the formula CVI urethane is prepared from the formula CV azide by reaction with an alkanol, aralkanol, phenol, or substituted phenol. For example, when methanol is employed the formula CVI compound is prepared within $R_1$ is methyl. This formula CVI, PG-type product is then employed in the preparation of either the compound CVII or CVIII compound.

In the preparation of the formula CVII primary amine from the formula CVI urethane, methods known in the art are employed. Thus, for example, treatment of the formula CVII urethane with strong base at temperatures about $50°$ C. are employed. For example, sodium potassium or lithium hydroxide is employed.

Alternatively, the formula CVI compound is employed in the preparation of the formula CVII compound. Thus, when $L_2$ is alkyl the formula CVIII compound is prepared by reduction of the formula CVI urethane wherein $R_1$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) with an alkyl chloroformate. The reaction thus proceeds by methods known in the art for the preparation of carbamates from corresponding secondary amines. Finally, the formula CX product wherein $L_2$ and $L_3$ are both alkyl is prepared by reduction of the formula CIX carbamide. Accordingly, methods hereinabove described for the preparation of the formula CVIII compound from the formula CVI compound are used. Optionally, the various reaction steps herein are proceeded by the employment of blocking groups according to $R_{10}$, thus necessitating their subsequent hydrolysis in preparing each of the various products above. Methods described hereinabove for the introduction and hydrolysis of blocking groups according to $R_{10}$ are employed.

Finally, the processes described above for converting the formula CII compound to the formula CVI compound and the various compounds thereafter, result in shortening the 8α-side chain of the formula CI compound by one carbon atom. Accordingly, the formula CI starting material should be selected so as to compensate for the methylene group which is consumed in the steps of the above synthesis. Thus, where a 2a-homo-product is desired a corresponding formula CI 2a,2b-dihomo starting material must be employed. Starting materials containing an additional methylene group in the formula CI compound between the $Z_1$ moiety and the carboxyl are prepared by methods known in the art or procedures described above. For example, Wittig reagents containing an additional methylene are known in the art or prepared by methods described above.

Chart H provides a method whereby the formula CXI compound is transformed to the formula CXIV or formula CXV prostaglandin analogs of the present invention.

The formula CXII compound is prepared from the formula CXI compound by selective transformation of the secondary hydroxyls of the formula CXI compound to alkyl or aryl sulfonyl derivatives. Methos of sulfonation hereinabove described (i.e. Chart E) are employed. Thus, for example, the corresponding alkyl or aryl sulfonyl chlloride and a tertiary amine condensing agent are reacted with the formula CXI compound to prepare the formula CXII product.

When the formula CXI compound of Chart H represents a 2-decarboxy-2-aminomethyl or 2-decarboxy-2-hydroxymethyl-PG-type compound, the selectively of the sulfonation of secondary hydroxyls (over the primary hydroxyl or the amine) is assured by first preparing a C-1 derivative of such a formula CXI compound. For example, such a formula CXI compound is first selectively silylated at C-1. ($X_1$ is —$CH_2OH$) or t-butoxycarbonylated ($X_1$ is —$CH_2NH_2$). Thereafter the sulfonation prŏceeds. Finally the silyl or t-butoxycarbonyl group is hydrolyzed under mild acidic conditions, e.g., acetic acid or dilute hydrochloric acid in acetic acid, respectively.

Silyl groups useful in the present process and methods for accomplishing the selective silylation are known in the art. See for example U.S. Pat. No. 3,822,303.

The formula CXIII compound is then prepared from the formula CXII compound by displacement with hydrazine in a solubilizing organic solvent. Thus, for example, suitable solvents include t-butanol in ethanol dimethylsulfoxide and hexamethylphosphoramide. Finally, this formula CXIII compound is transformed to the present title product by oxidation. This oxidation proceeds spontaneously by exposing the formula CXIII compound to air, or as catalyzed by the addition of copper (II) acetate, hydrogen peroxide (see Journal of Organic Chemistry 40, 456 (1975)) or mercuric oxide (see Journal of Organic Chemistry 17:1666 (1952)).

Optionally, the formula CXIII compound is transformed to the formula CXV dialkylate or diacylate or the formula CXVI or CXVII monoalkylates and acylates. In alkylating, the alkyl iodide corresponding to the desired product is employed. In the preparation of the acylated product, the acid anhydride or acid chloride is reacted with the formula CXIII hydrazine in the presence of a tertiary amine base. In the event undesired (e.g., C-1) esters are generated, the acylation is followed by saponification, for example, in methanolic sodium bicarbonate).

When the formula CXVI and formula CXVII monoacylates or alkylates are desired, a single equivalent of the corresponding alkylating or acylating agent is employed. Thereafter, the mixture of products is separated by conventional (e.g., chromatographic) means.

When the formula CXV dialkylate or bis(acylate) is desired, two equivalents of the appropriate alkylating or acylating agent are employed.

Optionally, the monoalkylates of formula CXVI and CXVII are prepared directly from the formula CXII compound by employing an alkylhydrazine in place of hydrazine in the transformation of the formula CXII to the formula CXIII product.

Chart J provides the method whereby the formula CXIV 9,11,15-trideoxy-11α,9α-epoxyimino-PGF-type compounds are prepared as well as their corresponding formula CXV acylates and alkylates.

With respect to Chart J, the formula CXXII compound is prepared from the formula CXXI compound by selective monosulfonation, preferably preparing the monotosylate (p-toluenesulfonate) or mesylate (methylsulfonate).

For this selective monosulfonation, the formula CXXI compound is reacted with somewhat less than two equivalents of the sulfonyl chloride corresponding to the sulfonate to be prepared. Further, the reaction is run at low temperature (e.g., at or below about 0° C.) When $X_1$ is —$CH_2OH$ or —$CH_2NL_2L_3$, C-1 protection as described in Chart H is employed. However, such protected C-1 derivatives are hydrolyzed just prior to epoxyiminocyclization, described below.

The formula CXXIII compound is then prepared from the formula CXXII compound by reaction of the formula CXXII compound with N-hydroxyphthalimide in the presence of diethylazodicarboxylate and triphenylphosphine. A slight stoichiometric excess of both N-hydroxyphthalimide and diethylazodicarboxylate are employed. The reaction is run in organic solvents (e.g., tetrahydrofuran) and is ordinarily complete within several minutes. Formula CXXXIII product is then recovered by conventional (e.g., chromatographic) means.

the formula CXXIV analog is then prepared from the formula CXXIII compound by epoxyiminocyclization. Accordingly, the formula CXXIII compound is treated with an excess of hydrazine hydrate in, for example, a lower alkanol. The epoxyiminocyclization is ordinarily complete within several minutes, the reaction progress being conveniently monitored by silica gel TLC. Thereafter, the pure CXXIV product is obtained by conventional isolation and purification techniques.

Formula CXXV compound is then prepared from the formula CXXIV compound by alkylation or by acylation, for example as is described in Chart H for the preparation of a formula CXV - CXVII products.

Chart K provides a method whereby the formula CXXXI compound is transformed to the formula CXXXV 9,11,15-trideoxy-9α,11α-epoxyimino-PGF-type compounds and formula CXXXVI alkylates and acylates.

With respect to Chart K, the formula CXXXII compound is prepared from the formula CXXXI compound by a selective monosilylation (or disilylation when $X_1$ is not an ester or amide or amino) or by preparing a t- butoxycarbonyl derivative followed by selective monosilylation when $X_1$ is $-CH_2NL_2L_3$.

The formula CXXXIII compound is then prepared from the formula CXXXII compound by sulfonation, likewise employing methods described above.

Thereafter the formula CXXXIV compounds is prepared from the formula CXXXIII compound by mild acetic hydrolysis of the silyl ether and t-butoxycarbonyl moiety when $X_1$ is $-CH_2NL_2L_3$. Thereafter, the formula CXXXIV compound is transformed respectively to the formula CXXXV and CXXXVI compound by the method described in Chart J for the transformation of the formula CXXII compound to the formula CXXIV and CXXV compounds.

As discussed above, the processes herein described lead variously to carboxylic acids ($X_1$ is $-COOR_1$ and $R_2$ is hydrogen) ot to esters when preparing novel analogs wherein $X_1$ is $-COOR_1$.

When the alkyl ester has been obtained and an acid is desired, saponification procedures, as known in the art for PGF-type compounds are employed.

For alkyl esters enzymatic processes for transformation of esters to their acid forms may be used by methods known in the art when saponification procedures would cause undesired molecular changes in the prostaglandin analog. See for reference E. G. Daniels, Process For Producing An Esterase, U.S. Pat. No. 3,761,356. When an acid has been prepared and an alylk, cycloalkyl, or aralkyl ester is desired, esterification is advantageously accomplished by interaction of the acid with appropriate diazohydrocarbon. For example, when diazomethane is used, the methyl ester are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageouly in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N. Y., Vol. 8, pp. 389-394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid PG-type compounds, differing as to yield and purity of product.

With regard to the preparation of the phenyl, particularly p-substituted phenyl esters disclosed herein (i.e., $X_1$ is $-COOR_1$ and R is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

having prepared the 9,11,15-trideoxy-PGF-type carboxylic acids, the corresponding carboxyamides are prepared by one of several amidation methods known in the prior art. See, for example, U.S. Pat. No. 3,981,868, issued Sept. 21, 1976 for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the 9-deoxy-9-methylene-PGF-type acids are prepared is, first, by transformation of such free acids to corresponding mixed acid anhydrides. By this procedure, the prostaglandin-type free acid is first neutralized with an quivalent of an amine base, and thereafter reacted a slight stoichiometric excess of a chloroformate corresponding to the mixed anhydride to be prepared.

The amine base preferred for neutralization is triethylamine, although other amines (e.g. pyridine, methyldiethylamine) are likewise employed. Further, a convenient, readily available chloroformate for use in the mixed anhydride production is isobutyl chloroformate.

The mixed anhydride formation proceeds by conventional methods and accordingly the 9,11,15-trideoxy-PGF-type free acid is mixed with both the tertiary amine base and the chloroformate in a suitable solvent (e.g. aqueous tetrahydrofuran), allowing the reaction to proceed at $-10°$ to $20°$ C.

Thereafter, the mixed anhydride is converted to the corresponding amido or cycloamido derivative by reaction with the amine corresponding to the amide to be prepared. In the case where the simple amide ($-NH_2$) is to be prepared, the transformation proceeds by the addition of ammonia. Accordingly, the corresponding amine (or ammonia) is mixed with the mixed anhydride at or about $-10$ to $+10°$ C., until the reaction is shown to be complete. For highly volatile amines, acid addition salts thereof (e.g., methylamine hydrochloride) are employed in place of the corresponding free base (e.g. methylamine).

Thereafter, the novel 9,11,15-trideoxy-PGF-type amido or cycloamido derivative is recovered from the reaction mixture by conventional techniques.

The carbonylamido and sulfonylamido derivative of the presently disclosed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl of sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure PG-type sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

The compounds of this invention prepared by the processes of this invention, in free acid form, are transformed to pharamcologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Eavporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, and T-60 spectrophotometer on deuterochloroform solutions with tetramethylsilane as an internal standard.

Mass spectra are recorded on an CEC model 21-110B Double Focusing High Resolution Mass Spectrometer or an LKB Model 9000 Gas-Chromatograph-Mass Spectrometer. Trimethylsilyl derivatives are used, except where otherwise indicated.

The Collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-cyclohexane-water (90:20:50:100) as in M. Hamberg and B. Samuelsson, J. Biol, Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

Preparation 1 cis-4,5-Didehydro-cis-13-$PGF_{1\alpha}$, methyl ester (Formula XXXVII: $R_1$ is methyl, $Z_2$ is cis—$CH_2$—CH=CH—$(CH_2)_2$—, $Y_2$ is cis—CH=CH—, $R_3$ and $R_4$ of the $L_1$ moiety are hydrogen, and $R_7$ is n-butyl).

Refer to Chart A.

A. A solution of 34.3 g. of thallous ethoxide in 125 ml. of dry benzene is cooled inan ice bath, and thereafter a solution of 25 g. of dimethyl 2-oxo-heptyl-phosphonate in 75 ml. of benzene is added and thereafter rinsed with 50 ml. of benzene. The solution is stirred for 30 min. at 5° C. and thereafter 22.1 g. of crystalline 3α-benzoyloxy-5α-hydroxy-2β-carboxaldehyde-1α-cyclopentaneacetic acid, γ lactone is aded rapidly. This reaction mixture is then stirred for 13 hr. at ambient temperature yielding a brown solution of pH 9–10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding 33.6 g. of an oil, which is then chromatographed on 600 g. of silica gel packed in 20 percent ethyl acetate in cyclohexane. Elution of 3α-benzoyloxy- 5α-hydroxy-2β-(3-oxo-trans-1-octenyl)-1α-cyclopentaneacetic acid, γ lactone.

alternatively this product is prepared by adding 3α-benzoyloxy-2β-carboxaldehyde-5α-hydroxy-1α-cyclopentaneacetic acid γ lactone (3 g.) in 30 ml. of dichloromethane to a solution of dimethyl 2-oxo-heptylphosphonate (6.6 g.) and sodium hydride (1.35 g.) in 15 ml. of tetrahydrofuran. The resulting reaction mixture is then stirred for 2 hr. at about 25° C., acidified with acetic acid, and concentrated under reduced pressure. The residue is partitioned between dichloromethane and water, and the organic phase is concentrated. The residue is chromatographed on silica gel, eluting with ethyl acetate in Skellysolve B (1:1).

B. A solution of 16.3 g. of the reaction product of part A in one l. of acetone (agitated by bubbling nitrogen through the solution) is irradiated for 3 hr. in a Rayonet Photochemical Reactor (RPR-208, using 8 lamps) wherein the photo emission spectrum shows substantial intenstiy at a wave length at or around 3500 Angstroms. The solvent is then evaporated and the residue chromatographed on 1.5 kg. of silica gel packed in 10 percent ethyl acetate in cyclohexane. Elution yields crude 3α-benzoyloxy-5α-hydroxy-2β-(3-oxo-cis-1-octenyl)-1α-cyclopentaneacetic acid γ-lactone. Further chromatographic purification yields the pure cis isomer.

C. Sodium borohydride (2.86 g.) is slowly added to a stirred suspension of 12.6 g. of anhydrous zinc chloride in 78 ml. of dimethyl ether in ethylene glycol dimethyl ether (glyme) with ice bath cooling. The mixture is stirred for 20 hr. at ambient temperature and thereafter cooled to $-20°$ C. A solution of 8.0 g. of 3α-benzoyloxy-5α-hydroxy-2β-(3-oxo-cis-1-octenyl)-1α-cyclopentaneacetic acid γ lactone (part b) in 80 ml. of glyme is added over a period of 15 min. Stirring is continued for 24 hr. at $-20°$ C. and thereafter 60 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield an oil, which when chromatographed on 900 g. of silica gel packed in one percent acetone and methylene chloride, eluting with one to 15 percent acetone in methylene chloride yields the epimerically pure title product (2.17 g. of the 3S epimer and 5.1 g. of the 3R epimer).

The 3S epimer exhibits ultraviolet absorptions at $\lambda_{max.}$ equals 230 nm. ($\epsilon$1300, 580). Infrared absorptions (cm.$^{-1}$) are observed at 3530, 3460, 1755, 1715, 1705, 1600, 1585, 1495, 1315, 1280, 1235, 1170, 1125, 1075, 1035, 975, 910, and 710. NMR absorptions in CDCl$_3$ are observed at 4.2, 4.7, 4186–5.82, 7.18–7.63, and 7.8–8.15 δ.

The 3R epimer exhibits ultraviolet absorption at $\lambda_{max.}$ of 230nm. ($\epsilon$12,560). NMR absorptions in CDCl$_3$ are observed 4.2–4.7, 4.86–5.82, 7.18–7.63, and 7.8–8.15.

D. A solution of 5 g. of the reaction product of part C in 150 ml. of methanol is purged with nitrogen. Thereafter, potassium carbonate (2.02 g.) is added and the resulting mixture is stirred at ambient temperature until thin layer chromatographic analysis shows the solvolysis to be complete (about 1.5 hr.). The methanol is then evaporated under reduced pressure. The residue is then shaken with ethyl acetate (250 ml.), brine (250 ml.), and 8 g. of potassium bisulfate. The aqueous layer is then extracted twice with 125 ml. of ethyl acetate and the organic extracts are dried over magnesium sulfate, and evaporated to yield an oil. This oil is then dissolved in chloroform and a few crystals of p-toluenesulfonic acid are added. When thin layer chromatography indicates the relactinization is complete (about 2 hr.), the reaction mixture is then ashed with aqeuous potassium bicarbonate, dried, and evaporated to yield an oil which is then chromatrographed using silica gel packed in one percent ethanol in methylene chloride for purification. Accordingly, 3 g. of the deacylated lactone are prepared.

E. A solution of 1.57 g. of the reaction product of part D above, in 35 ml. of methylene chloride (containing 2.5 ml. of dihydropyran and 100 mg. of pyridine hydrochloride) is allowed to stand for 23 hr. at ambient temperature. The reaction mixture is then washed with water, aqueous potassium bicarbonate, dried over magnesium sulfate, and evaporated, yielding an oil which is thereafter chromatographed on 200 g. of silica gel packed in one percent acetone in methylene chloride. Elution with from one to ten percent acetone in methylene chloride yields 1.7 g. of the bis-tetrahydropyranyl lactone corresponding to the lactone reaction product of part D above.

F. A solution of the reaction product of part E above in 20 ml. of toluene is cooled to $-70°$ C. and thereafter 10 ml. of 10 percent diisobutylaluminum hydride in toluene is slowly added. The reaction mixture is then stirred at $-70°$ C. until thin layer chromatographic analysis indicates that the reduction is complete (about 30 min.). Thereafter the cooling bath is removed and 9 ml. of a mixture of tetrahydrofuran and water (2:1) is added slowly. The reaction mixture is then stirred and allowed to warm to room temperature, and is then filtered through Celite. The filter cake is rinsed with benzene, combined organic extracts are then dried over magnesium sulfate and evaporated to yield 1.57 g. of 3α,5α-dihydroxy-2β-[(3S)-3-hydroxy-cis-1-octenyl]-1α-cyclopentaneacetaldehyde, γ-lactol, bis-tetrahydropyranyl ether.

G. A suspension of methoxymethyl-triphenylphosphonium chloride (32.4 g.) in 150 ml. of tetrahydrofuran is cooled to $-15°$ C. To the suspension is added 69.4 ml. of n-butyllithium in hexane (1.6 molar) in 45 ml. of tetrahydrofuran. After 30 min. there is added a solution of 3α,5α-dihydroxy2β-[(3R)-3-hydroxy-cis-1-octenyl]-1α-cyclopentaneacetaldehyde γ-lactol bis-(tetrahydropyranylether), part F (10 g.), in 90 ml. of tetrahydroufuran. The mixture is stirred for 1.5 hr. while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXVIII compound are combined.

H. The reaction product of part G above in 20 ml. of tetrahydrofuran is hydrolyzed with 50 ml. of 66 percent aqueous acetic acid at about 57° C. for 2.5 hr. The resulting mixture is then concentrated under reduced pressure. Toluene is added to the residue and the solution is again concentrated. Finally the residue is subjected to chromatography on silica gel, eluting with chloroform and methanol (6:1). The formula XXIX compound is thereby obtained by combining and concentrating fractions as shown by thin layer chromatography to contain pure γ-lactol.

I 3-Carboxypropyltriphenylphosphonium bromide (prepared by heating 4-bromobutyric acid and triphenylphosphine in benzene at reflux for 18 hr., and thereafter purifying), 1.06 g., is added to sodiomethylsulfinylcarbanide prepared from sodium hydride (2.08 g., 57 percent) and 30 ml. of dimethylsulfoxide. The resulting Wittig reagent is combined with the formula XXIX lactol of part H above and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate and isomeric hexanes (3:1). Those fractions as shown to contain the desired compound by thin layer chromatography are combined to yield the free acid of pure title product.

J. The Reaction product of part I above is reacted with ethereal diazomethane preparing pure title methyl ester.

Preparation 2 cis-4,5-Didehydro-cis-13,11$\beta$-PGF$_1\beta$, methyl ester (Formula XXXVIII: R$_1$, Z$_2$, Y$_2$M$_9$, L$_1$, and R$_7$ are as defined in Preparation 1):

Refer to Charts A and D.

A. A solution of 8g. of the reaction product of Preparation 1 and 2.7 g. of n-butylboronic acid in 300 ml. of methylene chloride are heated to reflux. As 30 ml. aliquots of methylene chloride are evaporated, a like quantity is replaced until 150 ml. of methylene chloride are replaced. After to cooling to ambient temperature 0.6 g. of pyridine hydrochloride in 70 ml. of dihydropyran are added and the resulting mixture stirred at ambient temperature under nitrogen for 18 hr. Thereafter the mixture is concentrated to about 50 ml. and 100 ml. of methanol is added. After cooling is an ice-bath, a mixture of 30 ml. of 30 percent hydrogen peroxide and 150 ml. of aqueous sodium bicarbonate is added and the resulting solution stirred for one hr. Thereafter the mixture is poured into 300 ml. of ethyl acetate; the aqueous layer saturated with sodium chloride; and the resulting layer separated. The aqueous portion is extracted with ethyl acetate and the combined organic extracts are washed with brine, dried over sodium sulfate, and concentrated to an oil. This crude oil is then chromatographed on silica gel packed with 50 percent ethyl acetate in hexane and eluted with ethyl acetate and hexane, yielding the mono-tetrahydropyranyl ether as in formula LXII of Chart D.

B. A solution of 6.7 g. of the reaction product of part A, 15.5 g. of triphenylphosphine and 7.2 g. of benzoic acid in 200 ml. of dry tetrahydrofuran is cooled to 0° C. under a nitrogen atmosphere. Thereupon, 10.2 g. of diethyl azodicarboxylate in 10 ml. of tetrahydrofuran is added over one min. to the above solution (rapidly stirred). After about 10 min. the reaction is substantially complete, however, after an additional 45 min., the reaction being complete, the mixture is poured into 400 ml. of ethyl acetate and hexane (1:1). The mixture is then washed with 150 ml. of saturated sodium bicarbonate and brine, washed with brine, dried over sodium sulfate, and concentrated to a solid mass. This solid mass is then suspended in 15 percent ethyl acetate and hexane and 18 g. of triphenylphosphine oxide is precipitated and removed by filtration. The remaining oil is then chromatographed on 2 kg. of silica gel, packed with ethyl acetate and Skellysolve B, and eluted with various mixtures of ethyl acetate and Skellysolve B, yielding a dibenzoate, tetrahydropyranyl ether as in formula LXIII of Chart D.

C. A solution of 5.6 g. of the reaction product of part B in 15 ml. of dry methanol is stirred at ambient temperature under a nitrogen atmosphere, while 10 ml. of 25 percent sodium methoxide in methanol is added. After about 3 hr. the solution is poured into 300 ml. of ice-cold saturated ammonium chloride and 15 ml. of 2N sodium bisulfate. The resulting mixture is then extracted thoroughly with ethyl acetate and the combined organic extracts are washed with brine, dried over sodium sulfate, and concentrated to yield crude product. This crude product is then chromatographed on 300 g. of silica gel, packed with mixtures of ethyl acetate and hexane, then eluted with various mixtures of ethyl acetate and hexane, yielding a dihydroxy tetrahydropyranyl ether as in formula LXIV of Chart D.

D. A solution of 4.3 g. of the reaction product of part C in 100 ml. of a mixture of acetic acid, water, and tetrahydrofuran (3:1:1) is warmed to 40° C. for 2 hr. Thereupon the mixture is partitioned between 400 ml. of ethyl acetate in hexane (1:1) and 200 ml. of brine. The organic phase is then washed twice with brine, washed with saturated sodium bicarbonate (until basic), washed with brine, dried over sodium sulfate, and concentrated to an oil which is then chromatographically purified on silica gel, yielding the title product.

Preparation 3 15-Deoxy-cis-4,5-didehydro-13-cis-11$\beta$-PGF$_1\beta$, methyl ester and 15-Deoxy-cis-4,5-didehydro-13,14-dihydrotrans-14,15-didehydro-11$\beta$-PGF$_1\beta$, methyl ester (Formula XLI: R$_1$, Z$_2$, L$_1$, and R$_7$ are as defined in Preparation 1 and Y$_3$ is cis—CH'CH—CH$_2$— or trans—CH$_2$—CH=CH—, respectively).

Refer to Chart A.

A solution of 0.5 g. of cis-4,5-didehydro-cis-13-11$\beta$-PGF$_{1\beta}$ methyl ester, 0.83 g. of imidazole, and 0.92 g. of t-butyldimethylchlorosilane in 2 ml. of dry dimethylformamide is stirred at ambient temperature under a nitrogen atmosphere for 20 hr. The resulting solution is then cooled in an ice bath and 6.0 ml. of water is added. After 30 min. the mixture is poured into cold brine and extracted with hexane. The hexane extract is then washed with ice-cold 2N sodium bisulfate, ice-cold 2N sodium bisulfate, ice-cold saturated sodium bicarbonate, brine, and thereafter dried over sodium sulfate and concentrated to the formula XXXIX trimethylsilyl derivative of the starting material.

B. A solution of 1.0 g. of the reaction product of Part A in 22.0 ml. of methanol is treated with 15 ml. of 10 percent aqueous potassium hydroxide. After 48 hr. most of the methanol is evaporated under reduced pressure and the residue partitioned between hexane and an ice-cold 2N sodium bisulfate and brine. The aqueous portion is then extracted twice with hexane and the combined organic extracts are then washed twice with brine, dried over sodium sulfate, and concentrated to yield the free-acid of the reaction product of part A.

C. Methylamine (15 ml.) is condensed and maintained at −30 to −40° C. while 0.94 g. of the reaction product of part B in 2 ml. of a mixture of t-butanol and tetrahydrofuran (1:10) is added). Thereupon three small pieces of lithium metal (approximately one-third of a cm. long) are added at a rate of one per minute. After 10 min. a deep blue color persists. After 30 min. from the lithium addition, 10.0 g. of solid ammonium chloride are added and the solution becomes colorless. The methylamine is then allowed to evaporate at ambient temperature under a stream of nitrogen. Thereafter, ice-cold 2N aqueous sodium bisulfate is added and the resulting mixture extracted with 10 percent ethyl acetate in hexane. The combined organic extracts are then washed twice with brine, dried over sodium sulfate, and concentrated, yielding a mixture of the formula XL 15-deoxy compounds where Y is cis—CH=CH—CH$_2$— or trans—CH$_2$—CH=CH—.

D. A solution of 0.77 g. of the reaction product of part C in 20 ml. of a mixture of 2N aqueous hydrochloric acid and tetrahydrofuran (1:4) is stirred at 25° C. for 18 hr. under a nitrogen atmosphere. The resulting mixture is then poured into brine and extracted three times with ethyl acetate. The combined organic extract is then washed twice with brine, dried over sodium sulfate, and concentrated to yield a mixture of the free acids of the title product.

E. The crude product of part D is then dissolved in 25 ml. of acetonitrile and treated with 2 ml. of diisopropylethylamine and 4 ml. of methyl iodide at ambient temperature under a nitrogen atmosphere. After 3 hr. the mixture is poured into brine and extracted 3 times with ethyl acetate. The combined organic extracts are then washed twice with brine, dried over sodium sulfate, and concentrated to an oil. The resulting product is then chromatographed on 75 g. of silica gel packed with 30 percent ethyl acetate in hexane. Elution with 40 to 50 percent ethyl acetate in hexane yields the respective title methyl esters.

Preparation 4  13,14-Didehydro-5-oxa-16-phenoxy-17,18,19,20-tetranor-15-deoxy-11$\beta$-PGF$_1\beta$, methyl ester (formula XLVIII: R$_1$ is methyl, Z$_2$ is —CH$_2$—O—(CH$_2$)$_3$—, Y$_6$ is —C=CH$_2$—, R$_3$ and R$_4$ of the L$_1$ moiety are both hydrogen, and R$_7$ is

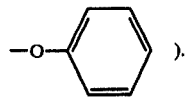

Refer to Chart B.

A. Following the procedure of Preparation 1, but employing N,N-dimethyl-3-phenoxypropylphosphoamide in place of dimethyl-2-oxohexylphosphonate, there is prepared 3$\alpha$-benzoyloxy-5$\alpha$-hydroxy-2$\beta$-(4-phenoxy-trans-1-butenyl)-1$\alpha$-cyclopentaneacetic acid $\gamma$-lactone and its corresponding cis-epimer.

B. A solution of the reaction product of part A (1.15 g.) in CC-4 (35 ml.) is treated with molecular chlorine (5.0 g.) and stirred. The resulting solution is then diluted with methylene chloride, washed with saline, and a sodium sulfate solution. This washed mixture is then dried and concentrated under reduced pressure. The residue thusly obtained is diluted with benzene and chromatographed on silica gel eluting with mixtures of hexane and ethyl acetate, yielding isomeric mixtures of 3$\alpha$-benzoyloxy-5$\alpha$-hydroxy-2$\beta$-(1,2-dichloro-4-phenoxybutyl)-1$\alpha$-cyclopentaneacetic acid $\gamma$-lactone. These dichlorides are then diluted with pyridine (20 ml.) and heated at 100° C. for 4.5 hr. The resulting solution is then diluted with diethyl ether and washed with ice-cold dilute hydrochloric acid and brine. The resulting mixture is then dried and subject to silica gel chromatography eluting with mixtures of hexane and ethyl acetate, yielding 3$\alpha$-benzoyloxy-5$\alpha$-hydroxy-2$\beta$-(2-chloro-4-phenoxy-trans-1-butenyl)-1$\alpha$-cyclopentaneacetic acid $\gamma$-lactone.

C. Following the procedure described in U.S. Pat. No. 3,931,279, at Preparation 12, parts E-G and Example 36, the reaction product of part B is transformed to 5-oxa-14-chloro-15-deoxy-16-phenoxy-17,18,19,20-tetranorPGF$_{1\alpha}$, methyl ester.

D. Following the procedure of Preparation 2, the reaction product of part C is transformed to 5-oxa-14-chloro-15-deoxy-16-phenoxy-17,18,19,20-tetranor-11$\beta$-PGF$_1\beta$, methyl ester.

E. A solution of potassium t-butoxide and t-butanol is treated with the reaction product of part D above. After several hours, the reaction mixture is diluted with diethyl ether and one percent aqueous potassium bisulfate is added. The aqueous phase is then extracted with diethyl ether and benzene and the combined organic extracts are washed with brine, dried and concentrated to yield crude title product. This crude product is then chromatographed on silica gel yielding 5-oxa-13,14-didehydro-15-deoxy-16-phenoxy-17,18,19,20-tetranor-11$\beta$-PGF$_1\beta$, methyl ester.

Preparation 5  3,7-Inter-m-phenylene-3-oxa-13,14-dihydro-15-deoxy-17-phenyl-4,5,6,18,19,20-hexanor-11$\beta$-PGF$_1\beta$, methyl ester (Formula LVII: R$_1$ is methyl, Z$_3$ is oxa, Y$_1$ is —(CH$_2$)$_3$—, R$_3$ and R$_4$ of the L$_1$ moiety are both hydrogen, and R$_7$ is benzyl).

Refer to Chart C.

A. 3,7-Inter-m-phenylene-3-oxa-4,5,6-trinor-PGF$_{1\alpha}$, methyl ester (10 g.) in 200 ml. of methanol is cooled to 0° C. in an ice bath. A stream of ozone, is generated from a conventional ozone producing apparatus, is passed through the mixture until the starting material is completely consumed. Thereupon the resulting mixture is washed, concentrated under reduced pressure, and the residue chromatographed, yielding the corresponding formula LII compound.

B. Following the procedure of Preparation 4, part A, but employing N,N-dimethyl-4-phenylbutylphosphoramide in place of N,N-dimethyl-3-phenoxypropylphosphoramide, there is prepared 3,7-inter-m-phenylene-3-oxa-15-deoxy-17-phenyl-4,5,6,18,19,20-hexanor-PGF$_{1\alpha}$, methyl ester, from the reaction product of part A.

C. A solution of the reaction product of part B in acetone and benzene, containing a catalytic amount of tris-(triphenylphoshine)rhodium (I) chloride is shaken under a hydrogen atmosphere at ambient temperature under one to 3 atmospheres of pressure for 3.5 hr. The solvent is then concentrated under reduced pressure and the residue chromatographed, yielding 3,7-inter-m-phenylene-3-oxa-13,14-dihydro-15-deoxy-17-phenyl-4,5,6,18,19,20-hexanor-PGF$_{1\alpha}$, methyl ester.

D. Following the procedure of Preparation 2 (Parts B and C) the reaction product of part C above is transformed to  3,7-inter-m-phenylene-13,14-dihydro-15-deoxy-17-phenyl-4,5,6,18,19,20-hexanor-11$\beta$-PGF$_1\beta$, methyl ester, the title product.

Preparation 6

2-Decarboxy-2-hydroxymethyl-15-deoxy-cis-13-cis-4,5-didehydro-11$\beta$-PGF$_1\beta$.

Refer to Chart F.

750 mg. of the reaction product of Preparation 3 dissolved in 50 ml. of diethyl ether are reacted with 500 mg. of lithium aluminum hydride at room temperature, with stirring. When the starting material is completely consumed (as indicated by thin layer chromatographic analysis) one ml. of water is cautiously added. Thereafter 0.8 ml. of 10 percent aqueous sodium hydroxide is added and the resulting mixture allowed to stir for 12 hr. Thereupon magnesium sulfate is added with stirring and the stirred mixture then filtered through magnesium sulfate and evaporated to a residue. Chromatographic purification yields pure title product.

Following the procedure of Preparation 6, but employing each of the various formula XCI 15-deoxy-11β-PGF β-type compounds there are prepared each of the various corresponding 2-decarboxy-2-hydroxymethyl-15-deoxy-11β-PGF$_{62}$-type products of formula XCII.

Preparation 7

2-Decarboxy-2-aminomethyl-15-deoxy-cis-13-cis-4,5-didehydro-11β-PGF$_1$β.

Refer to Chart G.

A. The reaction product of Preparation 3 is dissolved in one ml. of 95 percent ethanol. The resulting mixture is then transferred to a steel Parr bomb rinsed with 2 one-half ml. aliquots of 95 percent ethanol and 200 mg. of ammonium chloride are added. Then the mixture is cooled in a dry ice acetone bath and ammonia is added until about 5 to 10 ml. has condensed. The bomb is then sealed and allowed to warm to room temperature. Thereafter the bomb is placed in an oven at 50° C. for 2 days cooled in a dry-ice acetone bath, and opened. Thereafter residual ammonia is evaporated with nitrogen and the product extracted with ethyl acetate, washed with water and saturated brine, dried over sodium sulfate, and evaporated to yield 15-deoxy-cis-13-cis-4,5-didehydro-11β-PGF$_1$β, amide, formula CIII.

B. Lithium aluminum hydride (100 mg.) in 5 ml. of dry tetrahydrofuran under nitrogen is prepared. A solution of the reaction product of part A is then slowly added (being dissolved in a small amount of dry tetrahydrofuran). The resulting mixture is then stirred at room temperature for 48 hr. and thereafter one-tenth ml. of water is added while cooling the mixture in an ice bath. Thereafter 0.1 ml. of 15 percent sodium hydroxide and 0.3 ml. of water is added. The suspension is then filtered; dried over magnesium sulfate; washed with ethyl acetate; and evaporated to yield a residue of the title product.

Following the procedure of Preparation 7, but employing each of the various formula XCI 15-deoxy-11β-PGF$_2$β-type compounds of formula CI there are prepared each of the various 2-decarboxy-2-aminomethyl-15-deoxy-11β-PGFβ-type compounds of Chart G.

Following the procedure of the above preparations, there are prepared each of the various formula CXI compounds of Chart H which are employed in the preparation of the novel formula CXIV compounds herein.

EXAMPLE 1

9,11,15-Trideoxy-9α,11α-azo-PGF$_2$ (Formula CIV: X$_1$ is —COOH, Z$_1$ is cis—CH=CH—(CH$_2$)$_3$—, Y$_1$ is trans—CH=CH—CG$_2$—, R$_3$ and R$_4$ of the L$_1$— moiety are hydrogen, and W$_1$ is

and R$_7$ is n-butyl).

A. Following the procedure of Preparation 3, 11β-PGF$_2$β, methyl ester is transformed to a mixture of 15-deoxy-11β-PGF$_2$β, methyl ester and 15-deoxy-13,14-dihydro-trans-14, 15-didehydro-11β-PGF$_2$β, methyl ester.

A solution of 0.59 g. of 15-deoxy-11β-PGF$_2$β, methyl ester (as prepared in part A) in 20 ml. of methylene chloride is cooled to −20° C. under a nitrogen atmosphere. Thereupon 0.57 g. of triethylamine is added, followed by addition of 0.30 ml. of methanesulfonyl chloride. After 10 min. the mixture is poured into a mixture of ice cold brine and 2N aqueous sodium bisulfate. The combined mixture is then extracted with ethyl acetate and the organic extracts washed with sodium bicarbonate and brine, dried over sodium sulfate, and concentrated to yield 0.80 g. of 15-deoxy-11β-PGF$_2$β, methyl ester, 9,11-bis-(methanesulfonate). Silica gel TLC R$_f$ is 0.35 in ethyl acetate and hexane (1:1). Infrared absorptions are observed at 2980, 2890, 1750, 1460, 1440, 1350, 1240, 1180, 970, and 910 cm.$^{-1}$.

C. An oil suspension of 0.66 g. of the reaction product of part B in 75 ml. of methanol and water (2:1) is stirred in the presence of 0.28 g. of lithium hydroxide. After 5 hr. at ambient temperature the solution is poured into ice-cold 2N aqueous sodium bisulfate and brine and extracted with ethyl acetate. The combined organic extracts are then washed twice with brine, dried over sodium sulfate, and concentrated to yield 0.66 g. of an oil. This crude product is then chromatographed on 75 g. of silica gel (CC-4) packed with 30 percent ethyl acetate and hexane and eluted with 30 to 45 percent ethyl acetate in hexane, yielding 15-deoxy-11β-PGF$_2$β, 9,11-bis-(methanesulfonate). Silica gel TLC R$_f$ is 0.28 in ethyl acetate, hexane, and acetic acid (50:50:1). Infrared absorptions are observed at 3300, 2970, 2890, 2700, 1715, 1460, 1410, 1350, 1175, 970, 910 cm.$^{-1}$. Characteristic NMR absorptions are observed at 5.50, 4.90, and 3.0 δ.

D. A solution of 0.24 g. of the reaction product of part C and 1.0 ml. of 95 percent hydrazine in 15 ml. of a mixture of t-butanol and ethanol (3:1) is warmed to reflux (in an oil bath, 95° C.) for 18 hr. After cooling, the mixture is concentrated to 0.59 g. of a crude product, 9,11,15-trideoxy-9α,11α-hydrazino-PGF$_{2α}$. Silica gel TLC R$_f$ is 0.15 in a mixture of methanol, ethyl acetate, and ammonium hydroxide (50:50:2).

E. A solution of 0.50 g. of the reaction product of part D in 20 ml. of a mixture of methanol and diethyl ether (3:1) is treated with 5 mg. of cupric acetate. After 90 min., the mixture is then concentrated to an oil which is taken up with ethyl acetate and filtered from resulting insoluble material, yielding 0.37 g. of crude title product. This crude product is then chromatographed on silica gel, packed with ethyl acetate and cyclohexane (1:4). Eluting with 30 percent ethyl acetate and hexane yields 80 mg. of pure title product. Silica gel TLC R$_f$ is 0.18 in a mixture of ethyl acetate, cyclohexane, and acetic acid (30:70:1).

EXAMPLE 2

9α,11α-azo-9,11,15-trideoxy-PGF$_2$, amide

A solution with 300 mg. of 9α,11α-azo-9,11,15-trideoxy PGF$_2$ in 8.0 ml. of dry acetonitrile is cooled to −10° C. under a nitrogen atmosphere. Thereafter 0.127 ml. of triethylamine is added followed by addition of 0.118 ml. of isobutylchloroformate. After 10 min. at −5° C., an ammonia saturated solution of 3 ml. of acetonitrile is added in one portion. After 5 min. at −5° C., and 10 min. at room temperature, the reaction mixture is diluted with ethyl acetate, and partitioned with a mixture of brine and $KH_2PO_4$(added to adjust pH to 4.5). The resulting layers are separated and the aqueous phase is extracted with ethyl acetate. The organic extract is then washed with brine, dried over sodium sulfate, and concentrated to yield 0.30 gms. of an oil. This oil is chromatographed on 50 gm. of silica gel packed and eluted with ethyl acetate, yielding 270 mg. of pure title product. TLC $R_f$ is 0.24 in a mixture of ethyl acetate and acetic acid (99:1). Infrared absorptions are observed at 3300, 3100, 2900, 2800, 1670, 1620, 1490, 1460, and 965 cm.$^{-1}$. NMR absorptions are observed at 6.0, 5.4, 5.10, 4.90, and 0.90δ. The high resolution mass spectrum for the monotrimethylsilyl derivative exhibits a molecular ion peak at 403.3036.

Example

9α,11α-azo-9,11,15-trideoxy-PGF$_2$, p-carboxanilide (Formula IV: $X_1$ is $COL_4$, $L_4$ is

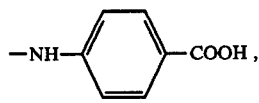

and $W_1$, $Z_1$, $Y_1$, $L_1$, and $R_7$ are as defined in Example 1).

To a solution of 393 mg. of 9α,11α-azo-9,11,15-trideoxy-PGF$_2$ at −10° C. in 5 ml. of acetone is added 0.14 ml. of triethylamine, followed by addition of 0.13 ml. of isobutylchloroformate. The resulting mixture is then stirred at −10° C. for 10 min. and thereafter treated with a mixture of 250 mg. of p-aminobenzoic acid, 0.2 ml. of triethylamine, and 5 ml. of acetone. The resulting mixture is then warmed to 25° C. and stirred for 20 min. Thereafter the stirred mixture is poured into cold dilute aqueous sodium bisulfate and extracted with ethyl acetate. The organic extracts are then washed with brine, dried over magnesium sulfate and evaporated to yield crude product. This crude product is then chromatographed 75 g. of silica gel packed with 40% ethyl acetate in hexane. Eluting with 40 to 70% ethyl acetate in hexane yields pure title product.

EXAMPLE 4

9α,11α-azo-9,11,15-trideoxy-PGF$_2$, methylsulphonylamide (Formula IV: $X_1$ is—$COL_4$, $L_4$ is —$NHSO_2CH_3$, an Z1, $W_1$, $Y_1$, $L_1$, and $R_7$ are as defined in Example 1).

To a stirred solution of 480 mg. of 9α,11α-azo-9,11,15-trideoxy-PGF$_2$ in 6.0 ml. of dimethylformamide 0.142 g. of triethylamine is added with stirring followed by addition of 0.19 g. of isobutyl chloroformate. This mixture is then stirred at 0° C. for 25 min. at which time 0.685 g. of methylsulfonamide sodium salt (prepared by adding 1.33 ml. of 4.4 N methanolic sodium methoxide to a solution of 0.604 g. of methanesulfonamide in 2.0 ml. of methanol, concentrating the mixture under reduced pressure, adding benzene to the residue, and again concentrating the mixture under reduced pressure). Thereafter 1.25 ml. of hexamethylphosphoramide is added and the mixture stirred at ambient temperature for 16 hrs. Acidification with cold dilute hydrochloric acid is followed by extraction with ethyl acetate. The organic extract is then washed with water, brine and dried over magnesium sulfate. Concentration at reduced pressure yields a residue which is chromatographed a 100 g. column of silica gel packed with 10% methanol in methylene chloride. Eluting with 7.5% methanol in methylene chloride yields pure title product.

EXAMPLE 5

9α,11α-azo-9,11,15-trideoxy-PGF$_2$, p-hydroxybenzaldehyde semicarbazone ester (Formula IV: $X_1$ is —$COOR_1$, and $R_1$ is

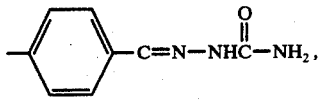

$Z_1$, $W_1$, $Y_1$, $L_1$, and $R_7$ are as defined in Example 1).

A solution of 1.0 g. of 9α,11α-azo-9,11,15-trideoxy-PGF$_2$ in 45 ml. of dry acetone is cooled to 0° C. and treated dropwise with 0.51 ml. of triethylamine. Thereafter 0.48 ml. of isobutylchloroformate is added. This mixture is stirred for 10 min. after which a triethylamine hydrochloride precipitate forms. A solution of 1.32 g. of p-hydroxybenzaldehyde semicarbazone in 13 ml. of pyridine is then added and the mixture allowed to warm to 25° C. This mixture is then stirred for 60 min. and thereafter concentrated under reduced pressure. The residue is then dissolved in ethyl acetate and filtered. The filter cake is then washed with ethyl acetate and the combined filtrate is evaporated and chromatographed on 200 g. of silica gel packed with 5% isopropanol and hexane. Eluting with isopropanol and hexane yields pure product which is then rechromatographed with tetrahydrofuran. Thereupon pure title produce is obtained.

Following the procedure of Example 1, but employing respectively in title products of Preparations 3–7 in place of the starting material therein, there ar prepared:
9,11,15-Trideoxy-9α,11α-azo-cis-13-cis-4,5-didehydro-PGF$_1$;
9,11,15-Trideoxy-9α,11α-azo-3,7-inter-m-phenylene-3-oxa-13,14-dihydro-17-phenyl-4,5,6,18,19,20-hexanor-PGF$_1$;
9,11,15-Trideoxy-9α,11α-azo-cis-13-cis-4,5-didehydro-2-decarboxy-2-hydroxymethyl-PGF$_1$; and
9,11,15-Trideoxy-9α,11α-azo-cis-13-cis-4,5-didehydro-2-decarboxy-2-aminomethyl-PGF$_1$.

Further, following the procedure of the above Examples, there are prepared methyl esters of the above 9,11,15-trideoxy-9α,11α-azo-PGF-type free acids by esterification with ethereal diazomethane. Further following the procedure of Example 1 15-deoxy-11β-PGF$_1$β is transformed to 9,11,15-trideoxy-9α,11α-azo-PGF$_1$.

Following the procedure of Example 1, but employing corresponding starting material as described above, there are prepared 9,11,15-trideoxy-9α,11α-azo-PGF$_2$- or PGF$_1$-type compounds, in free acid, ester, or amide form, or as corresponding 2-decarboxy-2-aminomethyl or 2-hydroxy- methyl derivatives, which exhibit the following side chain variations:

16-Methyl-;
16,16-Dimethyl-;
16-Fluoro-;
16,16-Difluoro-;
17-Phenyl-18,19,20-trinor-;
17-(m-trifluoromethylphenyl)-18,19,20-trinor-;
17-(m-chlorophenyl)-18,19,20-trinor-;

17-(p-fluorophenyl)-18,19,20-trinor-;
16-Methyl-b 17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
16-Methyl-16-phenoxy-18,19,20-trinor-;
13,14-Didehydro-; 16-Methyl-13,14-didehydro-;
16,16-Dimethyl-13,14-didehydro-;
16-Fluoro-13,14-didehydro-
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor:13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydeo-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17 -(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
2,2-Difluoro-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-dihydro-;
2,2,16,16-Tetrafluoro-17-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;

2,2-Difluoro-16-(m-chlorophenoxy)-17,18,19,20-tetranor-13,14-dihydro-;
2,2-Difluoro-16-(p-fluorophenoxy)-17,18,19,20-tetrnor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
16-Methyl-cis-13;
16,16-Dimethyl-cis-13-;
16-Fluoro-cis-13-;
16,16-Difluoro-cis-13-;
17-Phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-fluorophenyl)-18,19,20-trinor-cis-13-;
16-Methyl-17-phenyl-18,19,20-trinor-cis-13-;
16,16-Dimethyl-17-phenyl-18,19,20-trinor-cis-13-;
16-Fluoro-17-phenyl-18,19,20-trinor-cis-13-;
16,16-Difluoro-17-phenyl-18,19,20-trinor-cis-13-;
16-Phenoxy-17,18,19,20-tetranor-cis-13-;
16-(m-trifluoromethylphenoxy)-17,18,19,20-tetranor-cis-13-;
16-(m-chlorophenoxy)-17,18,19,20-tetranor-cis-13-;
16-(p-fluorophenoxy)-17,18,19,20-tetranor-cis-13-;
16-Phenoxy-18,19,20-trinor-cis-13-;
16-Methyl-16-phenoxy-18,19,20-trinor-cis-13-;
13,14-Dihydro-trans-14,15-didehydro-;
16-Methyl-13,14-dihydro-trans-14,15-didehydro-;
16,16-Dimethyl-13,14-dihydro-trans-14,15-didehydro-;
16-Fluoro-13,14-dihydro-trans-14,15-didehydro-;
16,16-Difluoro-13,14-dihydro-trans-14,15-didehydro-;
17-Phenyl-18,19,20-trinor-13,14-dihydro-trans-14,15-didehydro-;
17-(m-trifluoromethylphenyl)-18,19,20-trinor-13,14-dihydro-trans-14,15-didehydro-;
17-(m-chlorophenyl)-18,19,20-trinor-13,14-dihydro-trans-14,15-didehydro-;
17-(p-fluorophenyl)-18,19,20trinor-13,14-dihydro-trans-14,15-didehydro-;
16-Methyl-17-phenyl-18,19,20-trinor-13,14-dihydro-trans-14,15-didehydro-;
16,16-Dimethyl-17-phenyl-18,19,20-trinor-13,14-dihydro-trans-14,15-didehydro-;
16-Fluoro-17-phenyl-18,19,20-trinor-13,14-dihydro-trans-14,15-didehydro-;
16,16-Difluoro-17-phenyl-18,19,20-trinor-13,14-dihydro-trans-14,15-didehydro-;
16-Phenoxy-17,18,19,20-tetranor-13,14-dihydro-trans-14,15-didehydro-;
16-(m-trifluoromethylphenoxy)-17,18,19,20-tetranor-13,14-dihydro-trans-14,15-didehydro-;
16-(m-chlorophenoxy)-17,18,19,20-tetranor-13,14-dihydro-trans-14,15-didehydro-;
16-(p-fluorophenoxy)-17,18,19,20-tetranor-13,14-dihydro-trans-14,15-didehydro-;
16-Phenoxy-18,19,20-trinor-13,14-dihydro-trans-14,15-didehydro-;
16-Methyl-16-phenoxy-18,19,20-trinor-13,14-dihydro-trans-14,15-didehydro-;
2,2-Difluoro-cis-13-;
2,2-Difluoro-16-methyl-cis-13-;
2,2-Difluoro-16,16-dimethyl-cis-13-;
2,2-Difluoro-16-fluoro-cis-13-;
2,2-Difluoro-16,16-difluoro-cis-13-;
2,2-Difluoro-17-phenyl-18,19,20-trinor-cis-13-;
2,2-Difluoro-17-(m-trifluoromethylphenyl)-18,19,20-trinor-cis-13-;
2,2-Difluoro-17-(m-chlorophenyl)-18,19,20-trinor-cis-13-;
2,2-Difluoro-17-(p-fluorophenyl)-18,19,20-trinor-cis-13-;
2,2-Difluoro-16-methyl-17-phenyl-18,19,20-trinor-cis-13-;
2,2-Difluoro-16,16-dimethyl-17-phenyl-18,19,20-trinor-cis-13-;
2,2-Difluoro-16-fluoro-17-phenyl-18,19,20-trinor-cis-13-;
2,2-Difluoro-16,16-difluoro-17-phenyl-18,19,20-trinor-cis-13-;
2,2-Difluoro-16-phenoxy-17,18,19,20-tetranor-cis-13-;
2,2-Difluoro-16-(m-trifluoromethylphenoxy)-17,18,19,20-tetranor-cis-13-;
2,2-Difluoro-16-(m-chlorophenoxy)-17,18,19,20-tetranor-cis-13-;
2,2-Difluoro-16-(p-fluorophenoxy)-17,18,19,20-tetranor-cis-13-;
2,2-Difluoro-16-phenoxy-18,19,20-trinor-cis-13-;
2,2-Difluoro-16-methyl-16-phenoxy-18,19,20-trinor-cis-13-;
2,2-Difluoro-16-methyl-16-phenoxy-18,19,20-trinor-cis-13-;
2,2-Difluoro-13,14-dihydro-trans-14,15-didehydro-;
2,2-Difluoro-16-methyl-13,14-dihydro-trans-14,15-didehydro-;
2,2-Difluoro-16,16-dimethyl-13,14-dihydro-trans-14,15-didehydro-;
2,2,16-Trifluoro-13,14-dihydro-trans-14,15-didehydro-;
2,2,16,16-Tetrafluoro-13,14-dihydro-trans-14,15-didehydro-;
2,2-Difluoro-17-phenyl-18,19,20-trinor-13,14-dihydro-trans-14,15-didehydro-;
2,2-Difluoro-17-(m-trifluoromethylphenyl)-18,19,20-trinor-13,14-dihydro-trans-14,15-didehydro-;
2,2-difluoro-17-(m-chlorophenyl)-18,19,20-trinor-13,14-dihydro-trans-14,15-didehydro-;
2,2-Difluoro-17-(p-fluorophenyl)-18,19,20-trinor-13,14-dihydro-trans-14,15-didehydro-;
2,2-Difluoro-16-methyl-17-phenyl-18,19,20-trinor-13,14-dihydro-trans-14,15-didehydro-;
2,2-Difluoro-16,16-dimethyl-17-phenyl-18,19,20-trinor-13,14-dihydro-trans-14,15-didehydro-;
2,2,16-Trifluoro-17-phenyl-18,19,20-trinor-13,14-dihydro-trans-14,15-didehydro-;
2,2,16,16-Tetrafluoro-17-phenyl-18,19,20-trinor-13,14-dihydro-trans-14,15-didehydro-;
2,2-Difluoro-16-phenoxy-17,18,19,20-tetranor-13,14-dihydro-trans-14,15-didehydro-;
2,2-Difluoro-16-(m-trifluoromethylphenoxy)-17,18,19,20-tetranor-13,14-dihydro-trans-14,15-didehydro-;
2,2-Difluoro-16-(m-chlorophenoxy)-17,18,19,20-tetranor-13,14-dihydro-trans-14,15-didehydro-;
2,2-Difluoro-16-(p-fluorophenoxy)-17,18,19,20-tetranor-13,14-dihydro-trans-14,15-didehydro-;
2,2-Difluoro-16-phenoxy-18,19,20-trinor-13,14-dihydro-trans-14,15-didehydro-;
2,2-Difluoro-16-methyl-16- phenoxy-18,19,20-trinor-13,14-dihydro-trans-14,15-didehydro-;

Following the procedure of Example 1, but employing corresponding starting material as described above there are prepared 9,11,15-trideoxy-9α,11α-epoxymethano- or 11α,9α-epoxymethano-PGF$_1$-type compounds, in free acid or methyl ester form or as 2-decarboxy-2-aminomethyl or 2-hydroxymethyl derivatives, which exhibit the following functional characteristics:

3,7-Inter-m-phenylene-3-oxa-4,5,6-trinor-;
3,7-Inter-m-phenylene-3-oxa-4,5,6-trinor-16-methyl-;
3,7-Inter-m-phenylene-3-oxa-4,5,6-trinor-16,16-dimethyl-;
3,7-Inter-m-phenylene-3-oxa-4,5,6-trinor-16-fluoro-;
3,7-Inter-m-phenylene-3-oxa-4,5,6-trinor-16,16-difluoro-;
3,7-Inter-m-phenylene-3-oxa- 17-phenyl-4,5,6,18,19,20-hexanor-;
3,7-Inter-m-phenylene-3-oxa-17-(m-trifluoromethylphenyl)-4,5,18,19,20-hexanor;
3,7-Inter-m-phenylene-3-oxa-17-(m-chlorophenyl)-4,5,6,18,19,20-hexanor;
3,7-Inter-m-phenylene-3-oxa-17-(p-fluorophenyl)-4,5,6,18,19,20-hexanor-;
3,7-Inter-m-phenylene-3-oxa-16-methyl-17-phenyl-4,5,6,18,19,20-hexanor-;
3,7-Inter-m-phenylene-3-oxa-16,16-dimethyl-17-phenyl-4,5,6,18,19,20-hexanor;
3,7-Inter-m-phenylene-3-oxa-16-fluoro-17-phenyl4,5,6,18,19,20-hexanor;
3,7-Inter-m-phenylene-3-oxa-16,16-difluoro-17-phenyl-4,5,6,18,19,20-hexanor-;
3,7-Inter-m-phenylene-3-oxa-16-phenoxy-4,5,6,17,18,19,20-heptanor-;
3,7-Inter-m-phenylene-3-oxa-16-(m-trifluoromethylphenoxy)-4,5,6,17,18,19,20-heptanor-;
3,7-Inter-m-phenylene-3-oxa-16-(m-chlorophenoxy)-4,5,6,17,18,19,20-heptanor-;
3,7-Inter-m-phenylene-3-oxa-4,5,6-trinor-16-(p-fluorophenoxy)-4,5,6,17,18,19,20-heptanor-;
3,7-Inter-m-phenylene-3-oxa-16-phenoxy-4,5,6,18,19,20-hexanor-;
3,7-Inter-m-phenylene-3-oxa-4,5,6-trinor-16-methyl-16-phenoxy-4,5,6,18,19,20-hexanor-;
3,7-Inter-m-phenylene-3-oxa-4,5,6-trinor-13,14-didehydro-;
3,7-Inter-m-phenylene-3-oxa-4,5,6-trinor-16-methyl-13,14-didehydro-;
3,7-Inter-m-phenylene-3-oxa-4,5,6-trinor-16,16-dimethyl-13,14-didehydro-;
3,7-Inter-m-phenylene-3-oxa-4,5,6-trinor-16-fluoro-13,14-didehydro-;
3,7-Inter-m-phenylene-3-oxa-4,5,6-trinor-16,16-difluoro-13,14-didehydro-;
3,7-Inter-m-phenylene-3-oxa-17-phenyl-4,5,6,18,19,20-hexanor-13,14-didehydro-;
3,7-Inter-m-phenylene-3-oxa-17-(m-trifluoromethylphenyl)-4,5,6,18,19,20-hexanor-13,14-didehydro-;
3,7-Inter-m-phenylene-3-oxa-17-(m-chlorophenyl)-4,5,6,18,19,20-hexanor-13,14-didehydro-;
3,7-Inter-m-phenylene-3-oxa-17-(p-fluorophenyl)4,5,6,18,19,20-hexanor-13,14-didehydro-;
3,7-Inter-m-phenylene-3-oxa-16-methyl-17-phenyl-4,5,6,18,19,20-hexanor-13,14-didehydro-;
3,7-Inter-m-phenylene-3-oxa-16,16-dimethyl-17-phenyl-4,5,6,18,19,20-hexanor-13,14-didehydro-;
3,7-Inter-m-phenylene-3-oxa-16-fluoro-17-phenyl-4,5,6,18,19,20-hexanor-13,14-didehydro-;
3,7-Inter-m-phenylene-3-oxa-16,16-difluoro-17-phenyl-4,5,6,18,19,20-hexanor-13,14-didehydro-;
3,7-Inter-m-phenylene-3-oxa-16-phenoxy-4,5,6,17,18,19,20-heptanor-13,14-didehydro-;
3,7-Inter-m-phenylene-3-oxa-16-(m-trifluoromethylphenoxy)-4,5,6,17,18,19,20-heptanor-13,14-didehydro-;
3,7-Inter-m-phenylene-3-oxa-16-(m-chlorophenoxy)-4,5,6,17,18,19,20-heptanor-13,14-didehydro-;
3,7-Inter-m-phenylene-3-oxa-16-phenoxy-4,5,6,18,19,20-hexanor-13,14-didehydro-;
3,7-Inter-m-phenylene-3-oxa-16-methyl-16-phenoxy-4,5,6,18,19,20-hexanor-13,14-didehydro-;
3,7-Inter-m-phenylene-3-oxa-4,5,6-trinor-13,14-dihydro-;
3,7-Inter-m-phenylene-3-oxa-4,5,6-trinor-16-16-methyl-13,14-dihydro-;
3,7-Inter-m-phenylene-3-oxa-4,5,6-trinor-16,16-dimethyl-13,14-dihydro-;
3,7-Inter-m-phenylene-3-oxa-4,5,6-trinor-16-fluoro-13,14-dihydro-;
3,7-Inter-m-phenylene-3-oxa-4,5,6-trinor-16,16 -difluoro-13, 14-dihydro-;
3,7-Inter-m-phenylene-3-oxa-17-phenyl-4,5,6,18,19,20-trinor-13,14-dihydro-;
3,7-Inter-m-phenylene-3-oxa-17-(m-trifluoromethylphenyl)-4,5,6,18,19,20hexanor-13,14-dihydro-;
3,7-Inter-m-phenylene-3-oxa-17-(m-chlorophenyl)-4,5,6,18,19,20-hexanor-13,14-dihydro-;
3,7-Inter-m-phenylene-3-oxa-17-(p-fluorophenyl)-4,5,6,18,19,20-hexanor-13,14-dihydro-;
3,7-Inter-m-phenylene-3-oxa-16-methyl-17-phenyl-4,5,6,18,19,20-hexanor-13,14-dihydro-;
3,7-Inter-m-phenylene-3-oxa-16,16-dimethyl-17-phenyl-4,5,6,18,19,20-hexanor-13,14-dihydro-;
3,7-Inter-m-phenylene-3-oxa-16-fluoro-17-phenyl-4,5,6,18,19,20-hexanor-13,14-dihydro-;
3,7-Inter-m-phenylene-3-oxa-16,16-difluoro-17-phenyl-4,5,6,18,19,20-hexanor-13,14-dihydro-;
3,7-Inter-m-phenylene-3-oxo-16-phenoxy-4,5,6,17,18,19,20-heptanor-13,14-dihydro-;
3,7-Inter-m-phenylene-3-oxa-16-(m-trifluoromethylphenoxy)-4,5,6,17,18,19,20-heptanor-13,14-dihydro-;
3,7-Inter-m-phenylene-3-oxa-16-(m-chlorophenoxy)-4,5,6,17,18.19.20-heptanor-13,14-dihydro-;
3,7-Inter-m-phenylene-3-oxa-16-(p-fluorophenoxy)-4,5,6,17,18,19,20-heptanor-13,14-dihydro-;
3,7-Inter-m-phenylene-3-oxa-16-16-phenoxy-4,5,6,18,19,20-hexanor-13,14-dihydro-;
3,7-Inter-m-phenylene-3-oxa-16-methyl-16-phenoxy-4,5,6,18,19,20-hexanor-13,14-dihydro-;
3,7-Inter-m-phenylene-4,5,6-trinor-;
3,7-Inter-m-phenylene-4,5,6-trinor-16-methyl-;
3,7-Inter-m-phenylene-4,5,6-trinor-16,16-dimethyl-;
3,7-Inter-m-phenylene-4,5,6-trinor-16-fluoro-;
3,7-Inter-m-phenylene-4,5,6-trinor-16,16-difluoro-;
3,7-Inter-m-phenylene-17-phenyl-4,5,6,18,19,20-hexanor-;
3,7-Inter-m-phenylene-17-(m-trifluoromethylphenyl)-4,5,6,18,19,20-hexanor-;
3,7-Inter-m-phenylene-17-(m-chlorophenyl)-4,5,6,18,19,20-hexanor:;
3,7-Inter-m-phenylene-17-(p-fluorophenyl)-4,5,6,18,19,20-hexanor-;
3,7-Inter-m-phenylene-16-methyl-17-phenyl-4,5,6,18,19,20-hexanor-;
3,7-Inter-m-phenylene-16,16-dimethyl-17-phenyl-4,5,6,18,19,20-hexanor-;
3,7-Inter-m-phenylene-16-fluoro-17-phenyl-4,5,6,18,19,20-hexanor-;
3,7-Inter-m-phenylene-16,16-difluoro-17-phenyl-4,5,6,18,19,20-hexanor-;

3,7-Inter-m-phenylene-16-phenoxy-17-phenyl-4,5,6,17,18,19,20-heptanor-;
3,7-Inter-m-phenylene-16-(m-trifluoromethylphenoxy)-4,5,6,17,18,19,20-heptanor-;
3,7-Inter-m-phenylene-16-(m-chlorophenoxy)-4,5,6,17,18,19,20-heptanor-;
3,7-Inter-m-phenylene-16-(p-fluorophenoxy)-4,5,6,17,18,19,20-heptanor-;
3,7-Inter-m-phenylene-16-phenoxy-4,5,6,18,19,20-hexanor-;
3,7-Inter-m-phenylene-16-methyl-16-phenoxy-4,5,6,18,19,20-hexanor-;
3,7-Inter-m-phenylene-4,5,6-trinor-13,14-didehydro-;
3,7-Inter-m-phenylene-4,5,6-trinor-16-methyl-13,14-didehydro-;
3,7-Inter-m-phenylene-4,5,6-trinor-16,16-dimethyl-13,14-didehydro-;
3,7-Inter-m-phenylene-4,5,6-trinor-16-fluoro-13,14-didehydro-;
3,7-Inter-m-phenylene-4,5,6-trinor-16,16-difluoro-13,14-didehydro-;
3,7-Inter-m-phenylene-17-phenyl-4,5,6,18,19,20-hexanor-14didehydro-;
3,7-Inter-m-phenylene-17-(m-trifluoromethylphenyl)-4,5,6,18,19,20-hexanor-13,14-didehydro-;
3,7-Inter-m-phenylene-17-(m-chlorophenyl)-4,5,6,18,19,20-hexanor-13,14-didehydro-;
3,7-Inter-m-phenylene-17-(p-fluorophenyl)-4,5,6,18,19,20-hexanor-13,14-didehydro-;
3,7-Inter-m-phenylene-16-methyl-17-phenyl-4,5,6,18,19,20-hexanor-13,14-didehydro-;
3,7-Inter-m-phenylene-16,16-dimethyl-17-phenyl-4,5,6,18,19,20-hexanor-13,14-didehydro-;
3,7-Inter-m-phenylene-16-fluoro-17-phenyl-4,5,6,18,19,20-hexanor-13,14-didehydro-;
3,7-Inter-m-phenylene-16,16-difluoro-17-phenyl-4,5,6,18,19,20-hexanor-13,14-didehydro-;
3,7-Inter-m-phenylene-16-phenoxy-4,5,6,17,18,19,20-heptanor-13,14-didehydro-;
3,7-Inter-m-phenylene-16-(m-trifluoromethylphenoxy)-4,5,6,17,18,19,20-heptanor-13,14-didehydro-;
3,7-Inter-m-phenylene-16-(m-chlorophenoxy)-4,5,6,17,18,19,20-heptanor-13,14-didehydro-;
3,7-Inter-m-phenylene-16-phenoxy-4,5,6,18,19,20-hexanor-13,14-didehydro-;
3,7-Inter-m-phenylene-16-methyl-16-phenoxy-4,5,6,18,19,20-hexanor-13,14-didehydro-;
3,7-Inter-m-phenylene-4,5,6-trinor-13,14-dihydro-;
3,7-Inter-m-phenylene-4,5,6-trinor-16-methyl-13,14-dihydro-;
3,7-Inter-m-phenylene-4,5,6-trinor-16,16-dimethyl-13,14-dihydro-;
3,7-Inter-m-phenylene-4,5,6-trinor-16-fluoro-13,14-dihydro-;
3,7-Inter-m-phenylene-4,5,6-trinor-16,16-difluoro-13,14-dihydro-;
3,7-Inter-m-phenylene-17-phenyl-4,5,6,18,19,20-hexanor-13,14-dihydro-;
3,7-Inter-m-pheneylene-17-(m-trifluoromethylphenyl)-4,5,6,18,19,20-hexanor-13,14-dihydro-;
3,7-Inter-m-phenylene-17-(m-chlorophenyl)-4,5,6,18,19,20-hexanor-13,14-dihydro-;
3,7-Inter-m-phenylene-17-(p-fluorophenyl)-4,5,6,18,19,20-hexanor-13,14-dihydro-;
3,7-Inter-m-phenylene-16-methyl-17-phenyl-4,5,6,18,19,20-hexanor-13,14-dihydro-;
3,7-Inter-m-phenylene-16,16-dimethyl-17-phenyl-4,5,6,18,19,20-hexanor-13,14-dihydro-;
3,7-Inter-m-phenylene-16-fluoro-17-phenyl-4,5,6,18,19,20-hexanor-13,14-dihydro-;
3,7-Inter-m-phenylene-16,16-difluoro-17-phenyl-4,5,6,18,19,20-hexanor-13,14-dihydro-;
3,7-Inter-m-phenylene-16-phenoxy-4,5,6,17,18,19,20-heptanor-13,14-dihydro-;
3,7-Inter-m-phenylene-16-(m-trifluoromethylphenoxy)-4,5,6,17,18,19,20-heptanor-13,14-dihydro-;
3,7-Inter-m-phenylene-16-(m-chlorophenoxy)-4,5,6,17,18,19,20-heptanor-13,14-dihydro-;
3,7-Inter-m-phenylene-16-(p-fluorophenoxy)-4,5,6,17,18,19,20-heptanor-13,14-dihydro-;
3,7-Inter-m-phenylene-16-phenoxy-4,5,6,18,19,20-hexanor-13,14-dihydro-;
3,7-Inter-m-phenylene-16-methyl-16-phenoxy-4,5,6,18,19,20-hexanor-13,14-dihydro-;
5-Oxa-;
5-Oxa-16-methyl-;
5-Oxa-16,16-dimethyl-;
5-Oxa-16-fluoro-;
5-Oxa-16,16-difluoro-;
5-Oxa-17-phenyl-18,19,20-trinor-;
5-Oxa-17-(m-trifluoromethylphenyl)-18,19,20-trinor-;
5-Oxa-17-(m-chlorophenyl)-18,19,20-trinor-;
5-Oxa-17-(p-fluorophenyl)-18,19,20-trinor-;
5-Oxa-16-methyl-17-phenyl-18,19,20-trinor-;
5-Oxa-16,16-dimethyl-17-phenyl-18,19,20-trinor-;
5-Oxa-16-fluoro-17-phenyl-18,19,20-trinor-;
5-Oxa-16,16-difluoro-17-phenyl-18,19,20-trinor-;
5-Oxa-16-phenoxy-17,18,19,20-tetranor-;
5-Oxa-(m-trifluoromethylphenoxy)-17,18,19,20-tetranor-;
5-Oxa-16-(m-chlorophenoxy)-17,18,19,20-tetranor-;
5-Oxa-16-(p-fluorophenoxy)-17,18,19,20-tetranor-;
5-Oxa-16-phenoxy-18,19,20-trinor-;
5-Oxa-16-methyl-16-phenoxy-18,19,20-trinor-;
5-Oxa-13,14-didehydro-;
5-Oxa-16-methyl-13,14-didehydro-;
5-Oxa-16,16-dimethyl-13,14-didehydro-;
5-Oxa-16-fluoro-13,14-didehydro-;
5-Oxa-16,16-difluoro-13,14-didehydro-;
5-Oxa-17-phenyl-18,19,20-trinor-13,14-didehydro-;
5-Oxa-17-(m-trifluoromethylphenyl)-18,19,20-trinor-13,14-didehydro-;
5-Oxa-17-(m-chlorophenyl)-18,19,20-trinor-13,14-didehydro-;
5-Oxa-17-(p-fluorophenyl)-18,19,20-trinor-13,14-didehydro-;
5-Oxa-16-methyl-17-phenyl-18,19,20-trinor-13,14-didehydro-;
5-Oxa-16,16-dimethyl-17-phenyl-18,19,20-trinor-13,14-didehydro-;
5-Oxa-16-fluoro-17-phenyl-18,19,20-trinor-13,14-didehydro-;
5-Oxa-16,16-difluoro-17-phenyl-18,19,20-trinor-13,14-didehydro-;
5-Oxa-16-phenoxy-17,18,19,20-tetranor-13,14-didehydro-;
5-Oxa-16-(m-trifluoromethylphenoxy)-17,18,19,20-tetranor-13,14-didehydro-;
5-Oxa-16-(m-chlorophenoxy)-17,18,19,20-tetranor-13,14-didehydro-;
5-Oxa-16-phenoxy-18,19,20-trinor-13,14-didehydro-;
5-Oxa-16-methyl-16-phenoxy-18,19,20-trinor-13,14-didehydro-;
5-Oxa-13,14-dihydro-;
5-Oxa-16-methyl-13,14-dihydro-;
5-Oxa-16,16-dimethyl-13,14-dihydro-;

5-Oxa-16-fluoro-13,14-dihydro-;
5-Oxa-16,16-difluoro-13,14-dihydro-;
5-Oxa-17-phenyl-18,19,20-trinor-13,14-dihydro-;
5-Oxa-17-(m-trifluoromethylphenyl)-18,19,20-trinor-13,14-dihydro-;
5-Oxa-17-(m-chlorophenyl)-18,19,20-trinor-13,14-dihydro-;
5-Oxa-17-(p-fluorophenyl)-18,19,20-trinor-13,14-dihydro-;
5-Oxa-16-methyl-17-phenyl-18,19,20-trinor-13,14-dihydro-;
5-Oxa-16,16-Dimethyl-17-phenyl-18,19,20-trinor-13,14-dihydro-;
5-Oxa-16-fluoro-17-phenyl-18,19,20-trinor-13,14-dihydro-;
5-Oxa-16,16-difluoro-17-phenyl-18,19,20-trinor-13,14-dihydro-;
5-Oxa-16-phenoxy-17,18,19,20-tetranor-13,14-dihydro-;
5-Oxa-16-(m-trifluoromethylphenoxy)-17,18,19,20-tetranor-13,14-dihydro-;
5-Oxa-16-(m-chlorophenoxy)-17,18,19,20-tetranor-13,14-dihydro-;
5-Oxa-16-(p-fluorophenoxy)-17,18,19,20-tetranor-13,14-dihydro-;
5-Oxa-16-phenoxy-18,19,20-trinor-13,14-dihydro-;
5-Oxa-16-methyl-16-phenoxy-18,19,20-trinor-13,14-dihydro-;
3,7-Inter-m-phenylene-3-oxa-4,5,6-trinor-cis-13-;
3,7-Inter-m-phenylene-3-oxa-4,5,6-trinor-16-methyl-cis-13-;
3,7-Inter-m-phenylene-3-oxa-4,5,6-trinor-16,16-dimethyl-cis-13-;
3,7-Inter-m-phenylene-3-oxa-4,5,6-trinor-16-fluoro-cis-13-;
3,7-Inter-m-phenylene-3-oxa-4,5,6-trinor-16,16-difluoro-cis-13-;
3,7-Inter-m-phenylene-3-oxa-17-phenyl-4,5,6,18,19,20-hexanor-cis-13-;
3,7-Inter-m-phenylene-3-oxa-17-(m-trifluoromethylphenyl)-4,5,6,18,19,20-hexanor-cis-13-;
3,7-Inter-m-phenylene-3-oxa-17-(m-chlorophenyl)-4,5,6,18,19,20-hexanor-cis-13-;
3,7-Inter-m-phenylene-3-oxa-17-(p-fluorophenyl)-4,5,6,18,19,20-hexanor-cis-13-;
3,7-Inter-m-phenylene-3-oxa-16-methyl-17-phenyl-4,5,6,18,19,20-hexanor-cis-13-;
3,7-Inter-m-phenylene-3-oxa-16,16-dimethyl-17-phenyl-4,5,6,18,19,20-hexanor-cis-13-;
3,7-Inter-m-phenylene-3-oxa-16-fluoro-17-phenyl-4,5,6,18,19,20-hexanor-cis-13-;
3,7-Inter-m-phenylene-3-oxa-16,16-difluoro-17-phenyl-4,5,6,18,19,20-hexanor-cis-13-;
3,7-Inter-m-phenylene-3-oxa-16-phenoxy-4,5,6,17,18,19,20-heptanor-cis-13-;
3,7-Inter-m-phenylene-3-oxa-16-(m-trifluromethylphenoxy)-4,5,6,17,18,19,20-heptanor-cis-13-;
3,7-Inter-m-phenylene-3-oxa-16-(m-chlorophenoxy)-4,5,6,17,18,19,20-heptanor-cis-13-;
3,7-Inter-m-phenylene-3-oxa-4,5,6-trinor-16-(p-fluorophenoxy)-4,5,6,17,18,19,20-heptanor-cis-13-;
3,7-Inter-m-phenylene-3-oxa-16-phenoxy-4,5,6,18,19,20-hexanor-cis-13-;
3,7-Inter-m-phenylene-3-oxa-4,5,6-trinor-16-methyl-16-phenoxy-4,5,6,18,19,20-hexanor-cis-13-;
3,7-Inter-m-phenylene-3-oxa-4,5,6-trinor-13,14-dihydro-trans-14,15-didehydro-;
3,7-Inter-m-phenylene-3-oxa-4,5,6-trinor-16-methyl-13,14-dihydro-trans-14,15-didehydro-;
3,7-Inter-m-phenylene-3-oxa-4,5,6-trinor-16,16-dimethyl-13,14-dihydro-trans-14,15-didehydro-;
3,7-Inter-m-phenylene-3-oxa-4,5,6-trinor-16-fluoro-13,14-dihydro-trans-14,15-didehydro-;
3,7-Inter-m-phenylene-3-oxa-4,5,6-trinor-16,16-difluoro-13,14-dihydro-trans-14,15-didehydro-;
3,7-Inter-m-phenylene-3-oxa-17-phenyl-4,5,6,18,19,20-trinor-13,14-dihydro-trans-14,15-didehydro-;
3,7-Inter-m-phenylene-3-oxa-17-(m-trifluoromethylphenyl)-4,5,6,18,19,20-hexanor-13,14-dihydro-trans-14,15-didehydro-;
3,7-Inter-m-phenylene-3-oxa-17-(m-chlorophenyl)-4,5,6,18,19,20-hexanor-13,14-dihydro-trans-14,15-didehydro-;
3,7-Inter-m-phenylene-3-oxa-17-(p-fluorophenyl)-4,5,6,18,19,20-hexanor-13,14-dihydro-trans-14,15-didehydro-;
3,7-Inter-m-phenylene-3-oxa-16-methyl-17-phenyl-4,5,6,18,19,20-hexanor-13,14-dihydro-trans-14,15-didehydro-;
3,7-Inter-m-phenylene-3-oxa-16,16-dimethyl-17-phenyl-4,5,6,18,19,20-hexanor-13,14-dihydro-trans-14,15-didehydro-;
3,7-Inter-m-phenylene-3-oxa-16-fluoro-17-phenyl-4,5,6,18,19,20-hexanor-13,14-dihydro-trans-14,15-didehydro-;
3,7-Inter-m-phenylene-3-oxa-16,16-difluoro-17-phenyl-4,5,6,18,19,20-hexanor-13,14-dihydro-trans-14,15-didehydro-;
3,7-Inter-m-phenylene-3-oxa-16-phenoxy-4,5,6,17,18,19,20-heptanor-13,14-dihydro-trans-14,15-didehydro-;
3,7-Inter-m-phenylene-3-oxa-16-(m-trifluoromethylphenoxy)-4,5,6,17,18,19,20-heptanor-13,14-dihydro-trans-14,15-didehydro-;
3,7-Inter-m-phenylene-3-oxa-16-(m-chlorophenoxy)-4,5,6,17,18,19,20-heptanor-13,14-dihydro-trans-14,15-didehydro-;
3,7-Inter-m-phenylene-3-oxa-16-(p-fluorophenoxy)-4,5,6,17,18,19,20-heptanor-13,14-dihydro-trans-14,15-didehydro-;
3,7-Inter-m-phenylene-3-oxa-16-phenoxy-4,5,6,18,19,20-hexanor-13,14-dihydro-trans-14,15-didehydro-;
3,7-Inter-m-phenylene-3-oxa-16-methyl-16-phenoxy-4,5,6,18,19,20-hexanor-13,14-dihydro-trans-14,15-didehydro-;
3,7-Inter-m-phenylene-4,5,6-trinor-cis-13-;
3,7-Inter-m-phenylene-4,5,6-trinor-16-methyl-cis-13-;
3,7-Inter-m-phenylene-4,5,6-trinor-16,16-dimethyl-cis-13-;
3,7-Inter-m-phenylene-4,5,6-trinor-16-fluoro-cis-13-;
3,7-Inter-m-phenylene-4,5,6-trinor-16,16-difluoro-cis-13-;
3,7-Inter-m-phenylene-17-phenyl-4,5,6,18,19,20-hexanor-cis-13-;
3,7-Inter-m-phenylene-17-(m-trifluoromethylphenyl)-4,5,6,18,19,20-hexanor-cis-13-;
3,7-Inter-m-phenylene-17-(m-chlorophenyl)-4,5,6,18,19,20-hexanor-cis-13-;
3,7-Inter-m-phenylene-17-(p-fluorophenyl)-4,5,6,18,19,20-hexanor-cis-13-;
3,7-Inter-m-phenylene-16-methyl-17-phenyl-4,5,6,18,19,20-hexanor-cis-13-;
3,7-Inter-m-phenylene-16,16-dimethyl-17-phenyl-4,5,6,18,19,20-hexanor-cis-13-;
3,7-Inter-m-phenylene-16-fluoro-17-phenyl-4,5,6,18,19,20-hexanor-cis-13-;

3,7-Inter-m-phenylene-16,16-difluoro-17-phenyl-4,5,6,18,19,20-hexanor-cis-13-;
3,7-Inter-m-phenylene-16-phenoxy-17-phenyl-4,5,6,18,19,20-heptanor-cis-13-;
3,7-Inter-m-phenylene-16-(m-trifluoromethylphenoxy)-4,5,6,17,18,19,20-heptanor-cis-13-;
3,7-Inter-m-phenylene-16-(m-chlorophenoxy)-4,5,6,17,18,19,20-heptanor-cis-13-;
3,7-Inter-m-phenylene-16-(p-fluorophenoxy)-4,5,6,17,18,19,20-heptanor-cis-13-;
3,7-Inter-m-phenylene-16-phenoxy-4,5,6,18,19,20-hexanor-cis-13-;
3,7-Inter-m-phenylene-16-methyl-16-phenoxy-4,5,6,18,19,20-hexanor-cis-13-;
3,7-Inter-m-phenylene-4,5,6-trinor-16-methyl-13,14-dihydro-trans-14,15-didehydro-;
3,7-Inter-m-phenylene-4,5,6-trinor-16,16-dimethyl-13,14-dihydro-trans-14,15-didehydro-;
3,7-Inter-m-phenylene-4,5,6-trinor-16-fluoro-13,14-dihydro-trans-14,15-didehydro-;
3,7-Inter-m-phenylene-4,5,6-trinor-16,16-difluoro-13,14-dihydro-trans-14,15-didehydro-;
3,7-Inter-m-phenylene-17-phenyl-4,5,6,18,19,20-hexanor-13,14-dihydro-trans-14,15-didehydro-;
3,7-Inter-m-phenylene-17-(m-trifluoromethylphenyl)-4,5,6,18,19,20-hexanor-13,14-dihydro-trans-14,15-didehydro-;
3,7-Inter-m-phenylene-17-(m-chlorophenyl)-4,5,6,18,19,20-hexanor-13,14-dihydro-trans-14,15-didehydro-;
3,7-Inter-m-phenylene-17-(p-fluorophenyl)-4,5,6,18,19,20-hexanor-13,14-dihydro-trans-14,15-didehydro-;
3,7-Inter-m-phenylene-16-methyl-17-phenyl-4,5,6,18,19,20-hexanor-13,14-didehydro-trans-14,15-didehydro-;
3,7-Inter-m-phenylene-16,16-dimethyl-17-phenyl-4,5,6,18,19,20-hexanor-13,14-dihydro-trans-14,15-didehydro-;
3,7-Inter-m-phenylene-16-fluoro-17-phenyl-4,5,6,18,19,20-hexanor-13,14-dihydro-trans-14,15-didehydro-;
3,7-Inter-m-phenylene-16,16-difluoro-17-phenyl-4,5,6,18,19,20-hexanor-13,14-dihydro-trans-14,15-didehydro-;
3,7-Inter-m-phenylene-16-phenoxy-4,5,6,17,18,19,20-heptanor-13,14-dihydro-trans-14,15-didehydro-;
3,7-Inter-m-phenylene-16-(m-trifluoromethylphenoxy)-4,5,6,17,18,19,20-heptanor-13,14-dihydro-trans-14,15-didehydro-;
3,7-Inter-m-phenylene-16-(m-chlorophenoxy)-4,5,6,17,18,19,20-heptanor-13,14-dihydro-trans-14,15-didehydro-;
3,7-Inter-m-phenylene-16-(p-fluorophenoxy)-4,5,6,17,18,19,20-heptanor-13,14-dihydro-trans-14,15-didehydro-;
3,7-Inter-m-phenylene-16-phenoxy-4,5,6,18,19,20-hexanor-13,14-dihydro-trans-14,15-didehydro-;
3,7-Inter-m-phenylene-16-methyl-16-phenoxy-4,5,6,18,19,20-hexanor-13,14-dihydro-trans-14,15-didehydro;
5-Oxa-cis-13-;
5-Oxa-16-methyl-cis-13-;
5-Oxa-16,16-dimethyl-cis-13-;
5-Oxa-16-fluoro-cis-13-;
5-Oxa-16,16-difluoro-cis-13-;
5-Oxa-17-phenyl-18,19,20-trinor-cis-13-;
5-Oxa-17-(m-trifluoromethylphenyl)-18,19,20-trinor-cis-13-;
5-Oxa-17-(m-chlorophenyl)-18,19,20-trinor-cis-13-;
5-Oxa-17-(p-fluorophenyl)-18,19,20-trinor-cis-13-;
5-Oxa-16-methyl-17-phenyl-18,19,20-trinor-cis-13-;
5-Oxa-16,16-dimethyl-17-phenyl-18,19,20-trinor-cis-13-;
5-Oxa-16-fluoro-17-phenyl-18,19,20-trinor-cis-13-;
5-Oxa-16,16-difluoro-17-phenyl-18,19,20-trinor-cis-13-;
5-Oxa-16-phenoxy-17,18,19,20-tetranor-cis-13-;
5-Oxa-16-(m-trifluoromethylphenoxy)-17,18,19,20-tetranor-cis-13-;
5-Oxa-16-(m-chlorophenoxy)-17,18,19,20-tetranor-cis-13-;
5-Oxa-(p-fluorophenoxy)-17,18,19,20-tetranor-cis-13-;
5-Oxa-16-phenoxy-18,19,20-trinor-cis-13-;
5-Oxa-16-methyl-16-phenoxy-18,19,20-trinor-cis-13-;
5-Oxa-13,14-dihydro-trans-14,15-didehydro-;
5-Oxa-16-methyl-13,14-dihydro-trans-14,15-didehydro-;
5-Oxa-16,16-dimethyl-13,14-dihydro-trans-14,15-didehydro-;
5-Oxa-16-fluoro-13,14-dihydro-trans-14,15-didehydro;
5-Oxa-16,16-difluoro-13,14-dihydro-trans-14,15-didehydro-;
5-Oxa-17-phenyl-18,19,20-trinor-13,14-dihydro-trans-14,15-didehydro-;
5-Oxa-17-(m-trifluoromethylphenyl)-18,19,20-trinor-13,14-dihydro-trans-14,15-didehydro-;
5-Oxa-17-(m-chlorophenyl)-18,19,20-trinor-13,14-dihydro-trans-14,15-didehydro-;
5-Oxa-17-(p-fluorophenyl)-18,19,20-trinor-13,14-dihydro-trans-14,15-didehydro-;
5-Oxa-16-methyl-17-phenyl-18,19,20-trinor-13,14-dihydro-trans-14,15-didehydro-;
5-Oxa-16,16-Dimethyl-17-phenyl-18,19,20-trinor-13,14-dihydro-trans-14,15-didehydro;
5-Oxa-16-fluoro-17-phenyl-18,19,20-trinor-13,14-dihydro-trans-14,15-didehydro-;
5-Oxa-16,16-difluoro-17-phenyl-18,19,20-trinor-13,14-dihydro-trans-14,15-didehydro-;
5-Oxa-16-phenoxy-17,18,19,20-tetranor-13,14-dihydro-trans-14,15-didehydro-;
5-Oxa-16-(m-trifluoromethylphenoxy)-17,18,19,20-tetranor-13,14-dihydro-trans-14,15-didehydro-;
5-Oxa-16-(m-chlorophenoxy)-17,18,19,20-tetranor-13,14-dihydro-trans-14,15-didehydro-;
5-Oxa-16-(p-fluorophenoxy)-17,18,19,20-tetranor-13,14-dihydro-trans-14,15-didehydro-;
5-Oxa-16-phenoxy-18,19,20-trinor-13,14-dihydro-trans-14,15-didehydro-;
5-Oxa-16-methyl-16-phenoxy-18,19,20-trinor-13,14-dihydro-trans-14,15-didehydro-.

EXAMPLE 6

9α,11α-Methylhydrazine-9,11,15-trideoxy-PGE$_2$, methyl ester (Formula IV: W$_1$ is

$X_1$ is —COOCH$_3$, and $Z_1$, $Y_1'$ and $R_7$ are as defined above) and its 11α,9α-methylhydrazino isomer.

Refer to Chart H.

Following the procedure of Example 1, parts A, B, C, and D, but employing methylhydrazine in place of hydrazine in part D, there are obtained the mixture of title products. Chromatographing on silica gel yields isomerically pure title products.

Alternatively, the reaction product of part D of Example 1 is diluted in methanol and thereafter treated with a single stoichiometric equivalent of methyl iodide. The reaction mixture is then heated to reflux for about 6 hr. and when reaction is shown to be complete by silica gel TLC, diluted with ammonium hydroxide to pH 12. Title product is then obtained from the resulting reaction mixture by extraction with ethyl acetate, washing the extracts, and concentrating to yield pure isomerically mixed title products. Chromatographing on silica gel yields each pure isomeric title product.

Following the procedure described above but employing greater than 2 equivalents of methyl iodide, there is obtained N,N'-dimethyl-9α,11α-hydrazino-9,11,15-trideoxy-PGF$_2$, methyl ester.

EXAMPLE 7

9α,11α-(Acetyl)hydrazino-9,11,15-trideoxy-PGF$_2$, methyl ester (Formula IV: W$_1$ is

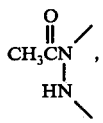

$X_1$ is —COOCH$_3$, and $Y_1$, $L_1$, $Z_1$, and $R_7$ are as defined in Example 1) and its 11α,9α-isomer.

Refer to Chart H.

9α,11α-hydrazine-9,11,15-trideoxy-PGF$_2$, methyl ester (the methyl ester of Example 1, part D) in pyridine is treated with one equivalent of acetic anhydride at 10° C. for several days. When thin layer chromatographic analysis indicates monoacetylation to be complete, pure title product is covered by conventional separation and purification techniques as an epimeric mixture. Silica gel chromatography yields pure 9α,11α-(acetyl)hydrazino- and 11α,9α-(acetyl)hydrazino-isomers.

Further following the procedure of Example 7 but employing a substantial excess of acetic anhydride, there is prepared N,N'-bis(acetyl)-9α,11α-hydrazino-9,11,15-trideoxy-PGF$_2$, methyl ester.

EXAMPLE 8

11α,9α-epoxyimino-9,11,15-trideoxy-PGF$_2$, methyl ester (Formula IV: W$_1$ is

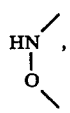

$X_1$ is —COOCH$_3$, and $Z_1$, $Y_1$, $L_1$, and $R_7$ are as defined in Example 1) and the corresponding free acid.

Refer to Chart J.

A. A solution of 1.0 g. of 15-deoxy-11β-PGF$_2$β, methyl ester is 30 ml. of dry pyridine is cooled in an ice bath under a nitrogen atmosphere. Thereafter 0.8 g. of p-toluenesulfonyl chloride is added in one portion. After the solution become homogeneous, the resulting mixture is then allowed at 0° C. for several days. Thereafter the resulting solution is poured into 200 ml. of ice cold brine and 125 ml. of 2 N aqueous sodium bisulfate. The resulting mixture is then extracted twice with ethyl acetate in hexane (1:1) the combined organic extracts are then washed successively with brine, 2 N aqueous sodium bisulfate, and brine; dried over sodium sulfate; and concentrated to an oil. The resulting crude 15-deoxy-11β-PGF$_2$β, 9-(p-toluenesulfonate), methyl ester, a CXXII compound, is chromatographed on silica gel, packed with ethyl acetate and hexane (1:4) and eluted with 20 to 30% ethyl acetate in hexane to yield 1.3 g. of pure title product. Silica gel TLC Rf is 0.38 in ethyl acetate and hexane (3:7). Infrared absorptions are observed at 3550, 2920, 2860, 1730, 1600, 1495, 1430, 1350, 1180, 1170, 1090, 1020, 970, 925, 860, 815, and 760 c$^{-1}$.

B. A solution of 0.70 g. of the reaction product of part A in 70 ml. of tetrahydrofuran under a nitrogen atmosphere at ambient temperature is treated with 0.43 g. of triphenylphosphine, 0.27 g. of N-hydroxyphthalimide, and 0.29 g. of diethylazodicarboxylate. After 15min. the resulting mixture is then concentrated to an oil and chromatographed on 300 g. of silica gel packed and eluted with diethyl ether in benzene (1:19), yielding 0.42 g. of pure 15-deoxy-PGF$_2$β, methyl ester, 9-(p-toluenesulfonate), 11-phthalimide. Silica gel TLC Rf is 0.37 in diethyl ether and benzene (1:9). Infrared absorptions are observed at 2950, 2870, 1790, 1730, 1600, 1495, 1460, 1430, 1350, 1185, 1170, 1090, 1080, 970, 875, 815, 785, 755, 700 cm$^{-1}$. NMR absorptions are observed at 7.8, 7.35, 5.30, 4.70, 3.65, and 2.45 δ.

C. A solution of 0.40 g. of the reaction product of part B in 40 ml. of methanol is treated with a solution of 180 mg. of hydrazine hydrate and 2 ml. of methanol. After 1 hr. the resulting solution is then poured into ice cold brine and ethyl acetate and the aqueous and organic layer separated. The aqueous layer is then extracted again with ethyl acetate and the organic layers combined, washed with brine, dried over sodium sulfate, and concentrated to an oil. The crude oil is then chromatographed on 50 g. of silica gel packed with ethyl acetate and hexane (1:4) and eluted with ethyl acetate and hexane (1:3) yielding 161 mg. of pure 9α,11α-epoxyimino-9,11,15-trideoxy-PGF$_2$, methyl ester. Silica gel TLC Rf is 0.24 in ethyl acetate and hexane (3:7). Infrared absorptions are observed at 3250, 2930, 2870, 1730, 1450, 1430, 1340, 1170, 1150, 1050, 965, and 915 cm$^{-1}$. NMR absorptions are observed at 5.35, 4.15, 3.65, and 3.40 δ. Mass spectrum exhibits a high resolution peak at 349.2585 and other peaks at 320, 318, 306, and 278.

D. The reaction product of part C in 25 ml. of methanol is cooled in an ice bath and 8 ml. of one N aqueous potassium hydroxide is added. The resulting solution is then stirred at ambient temperature for 4 hr., poured into 200 ml. of an ice cold buffer (pH 5), saturated with sodium chloride, and extracted twice with ethyl acetate. The combined ethyl acetate extracts are then washed with brine, dried over sodium sulfate, and concentrated to yield crude free acid. Title product is an oil. The crude free acid is then chromatographed on 20 g. of acid washed silica gel packed with ethyl acetate and hexane (3:7) and eluted with ethyl acetate and hexane (2:3), yielding 122 mg. of pure free acid. Crystallization from diethyl ether and hexane yielded a white crystalline solid melting point 53°-54° C. Silica gel TLC Rf is 0.22in ethyl acetate, hexane and acetic acid (50:50:1). Infrared absorptions are observed at 3250, 2940, 2870, 2550, 1710, 1440, 1340, 965, 910, and 730 cm$^{-1}$. NMR absorptions are observed at 10.2, 5.35, 4.20, 3.65, and 0.90 δ. The mass spectrum exhibits a high resolution peak at 407.2832 and other peaks at 392, 389, 378, 375, 364, and 336.

EXAMPLE 9

11α,9α-Epoxyimino-9,11,15-trideoxyPGF$_2$, methyl ester (formula IV: W$_1$ is

X$_1$ is —COOCH$_3$, and Y$_1$, Z$_1$, L$_1$, and R$_7$ are as defined in Example 1).

Refer to Chart K.

A solution of 2.15 g. of 15-deoxy-11β-PGF$_2$β, methyl ester is 6 ml. of dimethylformamide is cooled in an ice bath while a previously mixed solution of ice cold t-butyldimethylchlorosilane (0.97 g.) and imidazole (0.87 g.) in 6 ml. of dimethylformamide is added. After about 150 min., the resulting mixture is poured into 300 ml. of ice cold brine and extracted twice with ethyl acetate and hexane (1:1). The combined organic extracts are then washed with successively with cold 2 N aqueous sodium bisulfate, cold saturated aqueous sodium bicarbonate, in brine; dried over sodium sulfate; and concentrated to yield crude 15-deoxy-11β-PGF$_2$β-9-(t-butyldimethylsilyl ether) methyl ester, as an oil. This crude product is then chromatographed on silica gel packed with ethyl acetate and hexane (1:19) and eluted with ethyl acetate and hexane (1:9), to yield 0.79 g. of pure title product. Silica gel TLC Rf is 0.31 in ethyl acetate and hexane (1:1). Infrared absorptions are observed at 3550, 2930, 2860, 1730, 1450, 1425, 1250, 1100, 970, 870, 835, and 775 cm$^{-1}$. NMR absorptions are observed at 5.40, 3.90, and 3.60 δ.

B. The reaction product of part A (0.72 g.) in 30 ml. of dichloromethane is cooled to −20° C. under a nitrogen atmosphere. Thereafter triethylamine (0.43 g.) is added followed by addition of methanesulfonyl chloride (0.24 ml.) After 15 min. the resulting mixture is then poured into ice cold brine and ethyl acetate, the layers separated, the aqueous phase extracted again with ethyl acetate. The combined organic extracts are then washed with brine, dried over sodium sulfate, and concentrted to yield 0.89 g. of pure formula CXXXIII 15-deoxy-11β-PGF$_2$β, 9-(t-butyldimethylsilyl ether), 11-methanesulfonate, methyl ester. Silica gel TLC Rf is 0.17 in ethyl acetate and hexane (1:9). Infrared absorptions are observed at 2930, 2860, 1730, 1450, 1430 1170, 1105, 965, 910, 835, and 775 cm$^{-1}$.

C. A solution of 0.80 g. of the reaction product of part B in 15 ml. of a mixture of tetrahydrofuran and water in acetic acid (1:1:3) is stirred at ambient temperature under a nitrogen atmosphere for 30 hrs. The resulting mixture is then poured into 200 ml. of cold brine and 200 ml. of cold ethyl acetate and hexane (2:3). The layers are then separated and the aqueous phase extracted with 200 ml. of ethyl acetate and hexane (2:3). The combined organic extracts are then washed successively with brine, saturated aqueous sodium bicarbonate, in brine; dried over sodium sulfate; and concentrated to crude 15-deoxy-11β-PGF$_2$β, 11-methyl sulfonate, methyl ester as an oil. This crude oil is then chromatographed on silica gel, packed with ethyl acetate and hexane (3:7) and eluted with ethyl acetate and hexane (1:1), yielding 0.54 g. of pure formula CXXXIV product. Silica gel TLC Rf is 0.18 in ethyl acetate and hexane (1:1). Infrared absorptions are observed at 3600, 2920, 2860, 1735, 1420, 1340, 1170, 1080, 970, 905, and 775 cm$^{-1}$. NMR absorptions are observed at 5.50, 4.90, 3.90, 3.65, and 2.95 δ.

D. A solution of the reaction product of part C (0.51 g.) in 10 ml. of dry tetrahydrofuran is treated at ambient temperature under nitrogen atmosphere with 0.47 g. of triphenylphosphine and 0.29 g. of N-hydroxyphthalimide and diethylazocarboxylate (0.31g.) in tetrahydrofuran (0.50 ml.). After 30 min. an additional quantity of the N-hydroxyphthalimide and diethylazocarboxylate (one-third of the original quantities of each) is added and the mixture thereafter concentrated to an oil, triturated with ethyl acetate and hexane (3:17), and filtered to remove the triphenylphosphine oxide. The crude 15-deoxy-11β-PGF$_2$α, 9-phthalimide, methyl ester is then chromatographed on silica gel, packed with ethyl acetate and hexane (3:17) and eluted with 30–40% ethyl acetate in hexane, yielding 0.49 g. of pure product, which readily crystallize after removal of solvent. Silica gel TLC Rf is 0.27 in ethyl acetate and hexane (3:7). Infrared absorptions are observed at 2940, 2860, 1790, 1730, 1630, 1460, 1430, 1350, 1190, 1170, 1120, 1080, 970, 905, 880, 755, and 700 cm$^{-1}$. Infrared absorptions are observed at 7.8, 5.50, 4.20, 4.90, 3.65, and 2.95 δ.

E. A solution of 0.47 g. of the reaction product of part D and 40 ml. of methanol under a nitrogen atmosphere is treated at 0° C. with 0.19 g. of hydrazine hydrate and 10 ml. of methanol. After 3 hr. at ambient temperature the resulting mixture is then poured into 100 ml. of ice cold brine and 150 ml. of ethyl acetate and hexane (1:1). The layers are then separated and the aqueous phase extracted again with ethyl acetate and hexane (1:1). The combined organic extracts are then washed with brine, dried over sodium sulfate, and concentrated to an oil, crude 9α,11α-epoxyimino-9,11,15-trideoxy-PGF$_2$, methyl ester. This crude formula CXXXV product is then chromatographed on 75 g. of silica gel, packed with ethyl acetate and hexane (1:4), and eluted with 25–30% ethyl acetate and hexane, yielding 210 mg. of pure title product. Silica gel TLC Rf is 0.403 in ethyl acetate and hexane, (1:1). Infrared absorptions are observed at 3250, 2950, 2870, 1740, 1450, 1430, 1360, 1240, 1170, 1150, 1050, 965, and 810 cm$^{-1}$. NMR absorptions are observed at 5.4, 5.25, 5.65, 3.45 δ. The mass spectrum exhibits a high resolution peak at 349.592.

F. A solution of 190 mg. of the reaction product of part E and 35 ml. of methanol is cooled in an ice bath while 11 ml. of 1 N aqueous potassium hydroxide is added. The resulting mixture is then allowed to warm to ambient temperature for 3 hr. Thereupon the mixture is poured into 150 ml. of buffer (pH 5), ice cold brine, and ethyl acetate. The layers are then separated and the aqueous layer extracted again with ethyl acetate. The comined organic extracts are then washed with brine, dried over sodium sulfate and concentrated to yield title free acid. This crude title free acid is then chromatographed on acid washed silica gel packed with ethyl acetate and hexane (3:7) and eluted with 30-40% ethyl acetate and hexane, yielding 82 mg. of pure title free acid. Silica gel TLC Rf is 0.23 in ethyl acetate hexane and acetic acid (50:50:1). Infrared absorptions are observed at 3300, 3150, 2900, 2840, 2500, 1740, 1440, 1240, 965, 910 cm$^{-1}$. NMR absorptions are observed at 8.25, 5.35, 4.30, and 3.335 δ.

EXAMPLE 10

N-Methyl-9α,11α-epoxyimino-9,11,15-trideoxy-PGF$_2$, methyl ester (Formula IV: W$_1$ is

X$_1$ is —COCH$_3$, Z$_1$, Y$_1$, L$_1$, and R$_7$ are as defined in Example 1).

Following the procedure of Example 6 (alternate route), the methyl ester of Example 9 is transformed to the title product herein.

EXAMPLE 11

N-Acetyl-9α, 11α-epoxyimino-9,11,15-trideoxy-PGF$_2$, methyl ester (Formula IV: W$_1$ is

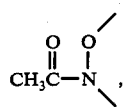

X$_1$ is —COCH$_3$, and Z$_1$, Y$_1$, and L$_1$ and R$_7$ are as defined in Example 1).

Following the procedure of Example 7, the title methyl ester of Example 9 is transformed to the title product herein.

Further following the procedure of Examples 10 and 11, but employing the title product of Example 8, there are prepared respectively N-methyl-11α,9α-epoxyimino-9,11,15-trideoxy-PGF$_2$, methyl ester and N-acetyl-11α,9α-epoxyimino9,11,15-trideoxy-PGF$_2$, methyl ester.

Further following the procedure of Examples 6-11, there are prepared prostaglandin analogs as free acids, esters, amides, primary amines (2-decarboxy-2-aminomethylPG compounds) or primary alcohols (2-decaroboxy-2-hydroxymethyl-PG), corresponding to each of the various 9α,11α-azo-9,11,15-trideoxy-PGF-type compounds described previously but in the form of:

11α,9α-epoxyimino-9,11,15-trideoxy-PGF-type compounds;
9α,11α-epoxyimino-9,11,15-trideoxy-PGF-type compounds;
N,N'-dimethyl-9α,11α-hydrazino-9,11,15-trideoxy-PGF-type compounds;
N,N'-bis(acetyl)-9α,11α-hydrazino-9,11,15-trideoxy-PGF-type compounds;
N-methyl-11α,9α-epoxyimino-9,11,15-trideoxy-PGF-type compounds;
N-acetyl-11α, 9α-epoxyimino-9,11,15-trideoxy-PGF-type compounds;
N-methyl-9α, 11α-epoxyimino-9,11,15-trideoxy-PGF-type compounds;
N-acetyl-]α,11α-epoxyimino-9,11,15-trideoxy-PGF-type compounds;
9α,11α-methylhydrazino-9,11,15-trideoxy-PGF-type compounds;
9α, 11α(acety)hydrazino-9,11,15-trideoxy-PGF-type compounds;
11α,9α-methylhydrazino-9,11,15-trideoxy-PGF-type compounds; and
11α,9α(acetyl)hydrazino-9,11,15-trideoxy-PGF-type compounds.

I claim:

1. A prostaglandin analog of the formula

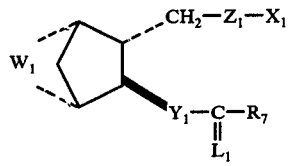

wherein W$_1$ is

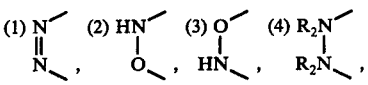

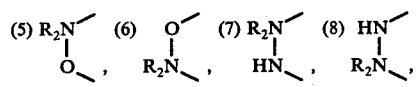

wherein R$_2$ is alkyl of one to 4 carbon atoms, inclusive or alkylcarbonyl of one to 4 carbon atoms, inclusive;
wherein Y$_1$ is
(1) trans—CH=CH—CH$_2$—,
(2) —(CH$_2$)$_3$-,
(3) —C|C—CH$_2$—,
(4) trans—CH$_2$—CH=CH—,or
(5) cis—CH=CH—CH$_2$—
wherein L$_1$ is

or a mixture of

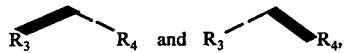

wherein R$_3$ and R$_4$ are hydrogen, methyl, or fluoro, being the same or different, with the proviso that one of R$_3$ and R$_4$ is fluoro only when the other is hydrogen or fluoro; wherein Z$_1$ is
(1) cis—CH=CH—CH$_2$—(CH$_2$)$_g$—CH$_2$—,
(2) cis—CH=CH—CH$_2$—(CH$_2$)$_g$—CF$_2$,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—, (7) 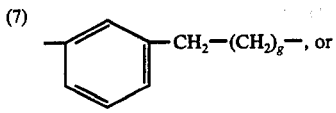

(8) 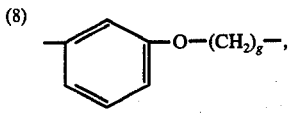

wherein g is one, 2, or 3; wherein $R_7$ is (1) —$(CH_2)_m$—$CH_3$, (2) 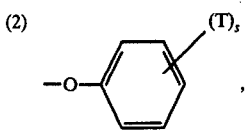

(3) 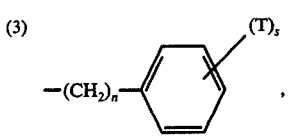

wherein h is zero to 3, inclusive, wherein m is one to 5, inclusive, T is chloro, fluoro, trifluoromethyl, alkyl of one to 3 carbon atoms, inclusive, or alkoxy of one to 3 carbon atoms, inclusive and s is zero, one, 2, or 3, the various T's being the same or different, with the proviso that not more than two T's are other than alkyl, with the further proviso that $R_7$ is

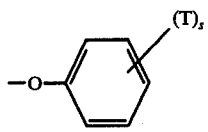

wherein T and s are as defined above, only when $R_3$ and $R_4$ are hydrogen or methyl, being the same or different; wherein $X_1$ is (1) —$COOR_1$ wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by (a) 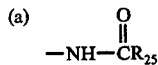

(b) 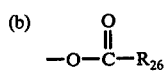

(c) 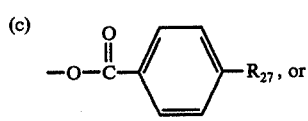

(d) 

wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is hydrogen or acetamido; inclusive, or a pharmacologically acceptable cation;

(2) —$CH_2OH$;

(3) —$COL_4$, wherein $L_4$ is (a) amido of the formula —$NR_{21}R_{22}$, wherein $R_{21}$ and $R_{22}$ are hydrogen; alkyl of one to 12 carbon atoms, inclusive; cycloalkyl of 3 to 10 carbon atoms, inclusive, aralkyl of 7 to 12 carbon atoms, inclusive, phenyl; phenyl substituted with one, 2, or 3 chloro, alkyl of one to 3 carbon atoms, inclusive; hydroxy, carboxy, alkoxycarbonyl of one to 4 carbon atoms, inclusive, or nitro; carboxyalkyl of one to four carbon atoms, inclusive; carbamoylalkyl of one to four carbon atoms, inclusive; cyanoalkyl of one to four carbon atoms, inclusive, acetylalkyl of one to four carbon atoms, inclusive; benzoylalkyl of one to four carbon atoms, inclusive; benzoylalkyl substituted by one, 2, or 3 chloro, alkyl of one to 3 carbon atoms, inclusive; hydroxy, alkoxy of one to 3 carbon atoms, inclusive; carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl of one to 4 carbon atoms, inclusive; pyridylalkyl substituted by one, 2, or 3 chloro, alkyl of one to 3 carbon atoms, inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of $R_{21}$ and $R_{22}$ is other than hydrogen or alkyl;

(b) cycloamido selected from the group consistng of

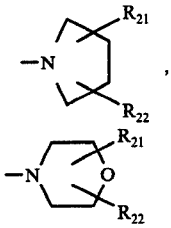

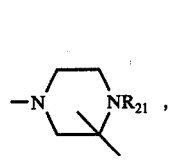

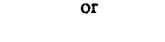

or

wherein $R_{21}$ and $R_{22}$ are as defined above;

(c) carbonylamido of the formula —$NR_{23}COR_{21}$, wherein $R_{23}$ is hydrogen or alkyl of one to 4 carbon atoms and $R_{21}$ is as defined above;

(d) sulphonylamido of the formula —$NR_{23}SO_2R_{21}$, wherein $R_{21}$ and $R_{23}$ are as defined above; or (e) hydrazino of the formula —$NR_{23}R_{24}$, wherein $R_{24}$ is amido of the formula —$NR_{21}R_{22}$, as defined above, or cycloamido, as defined above; or (4) —CH$_2$NL$_2$L$_3$, wherein L$_2$ and L$_3$ are hydrogen or alkyl of one to 4 carbon atoms, inclusive, being the same or different; or the pharmacologically acceptable acid addition salts thereof when
X$_1$ is not —COOR$_1$ and
R$_1$ a pharmacologically acceptable cation.

2. A prostaglandin analog according to claim 1, wherein W$_1$ is

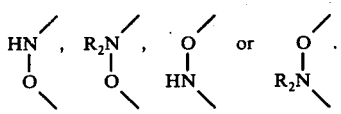

3. 9,11,15-Trideoxy-9α,11α-epoxyimino-prostaglandin F$_2$, a prostaglandin analog according to claim 2.

4. Cis-4,5-Didehydro-9,11,15-trideoxy-9α,11α- or 11α,9α-epoxyimino-prostaglandin F$_1$, methyl ester, a prostaglandin analog according to claim 2.

5. 9,11,15-Trideoxy-11α,9α-epoxyimino-prostaglandin F$_2$, a prostaglandin analog according to claim 2.

6. A prostaglandin analog according to claim 1, wherein W$_1$ is

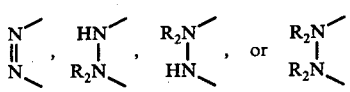

7. A prostaglandin analog according to claim 2, wherein X$_1$ is —COOR$_1$.

8. A prostaglandin analog according to claim 7, wherein Y$_1$ is trans-CH$_2$—CH=CH—.

9. 9,11,15-Trideoxy-9α,11α-azo-13,14-dihydro-trans-14,15-didehydro-prostaglandin F$_2$, a prostaglandin analog according to claim 8.

10. A prostaglandin analog according to claim 7, wherein T$_1$ is cis—CH=CH—CH$_2$—.

11. 9,11,15-Trideoxy-9α,11α-azo-cis-13-prostaglandin F$_2$, a prostaglandin analog according to claim 10.

12. A prostaglandin analog according to claim 7, wherein Y$_1$ is —C≡C—CH$_2$—.

13. 9,11,15-Trideoxy-9α,11α-azo-13,14-didehydro-prostaglandin F$_2$, a prostaglandin analog according to claim 12.

14. 9,11,15-Trideoxy-9α,11α-azo-13,14-didehydro-prostaglandin F$_1$, a prostaglandin analog according to claim 12.

15. A prostaglandin analog according to claim 7, wherein Y$_1$ is —(CH$_2$)$_3$—.

16. 9,11,15-Trideoxy-9α, 11α-azo-13,14-dihydro-prostaglandin F$_2$, a prostaglandin analog according to claim 15.

17. 9,11,15-Trideoxy-9α,11α-azo-13,14-dihydro-prostaglandin F$_2$, methyl ester, a prostaglandin analog according to claim 15.

18. A prostaglandin analog according to claim 7, wherein Y$_1$ is trans—CH=CH—CH$_2$—.

19. A prostaglandin analog according to claim 18, wherein Z$_1$ is cis—CH=CH—CH$_2$—(CH$_2$)$_g$—CF$_2$—.

20. 9,11,15-Trideoxy-9α,11α-azo-2,2-difluoro-prostaglandin F$_2$, a prostaglandin analog according to claim 19.

21. A prostaglandin analog according to claim 18, wherein Z$_1$ is cis—CH$_2$—CH=CH—(CH$_2$)$_g$—CH$_2$—.

22. 9,11,15-Trideoxy-9α,11α-azo-cis-4,5-didehydro-prostaglandin F$_2$, a prostaglandin analog according to claim 21.

23. A prostaglandin analog according to claim 18, wherein Z$_1$ is —(CH$_2$)$_3$—(CH$_2$)$_g$—CH$_2$—.

24. 9,11,15-Trideoxy-9α,11α-azo-prostaglandin F$_1$, a prostaglandin analog according to claim 23.

25. A prostaglandin analog according to claim 18, wherein Z$_1$ is —(CH$_2$)$_3$—(CH$_2$)$_g$—CF$_2$—.

26. 9,11,15-Trideoxy-9α,11α-2,2-difluoro-prostaglandin F$_1$, a prostaglandin analog according to claim 25.

27. A prostaglandin analog according to claim 18, wherein Z$_1$ is —CH$_2$—O—CH$_2$—(CH$_2$)$_g$—CH$_2$—.

28. 9,11,15-Trideoxy-9α,11α-azo-5-oxa-prostaglandin F$_1$, a prostaglandin analog according to claim 27.

29. A prostaglandin analog according to claim 18, wherein Z$_1$ is

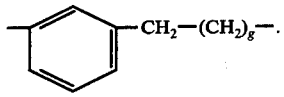

30. 9,11,15-Trideoxy-9α,11α-azo-3,7-inter-m-phenylene-4,5,6-trinor-prostaglandin F$_1$, a prostaglandin analog according to claim 29.

31. A prostaglandin analog according to claim 18, wherein Z$_1$ is

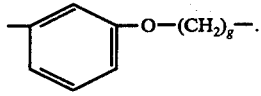

32. 9,11,15-Trideoxy-9α,11α-azo-3,7-inter-m-phenylene-3-oxa-4,5,6-trinor-prostaglandin F$_1$, a prostaglandin in analog according to claim 31.

33. A prostaglandin analog according to claim 18, wherein Z$_1$ is cis—CH=CH—CH$_2$—(CH$_2$)$_g$—CH$_2$—.

34. A prostaglandin analog according to claim 33, wherein R$_7$ is

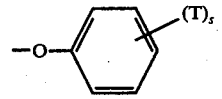

35. 9,11,15-Trideoxy-9α,11α-axo-16-phenoxy-17,18,19,20-tetranor-prostaglandin F$_2$, a prostaglandin analog according to claim 34.

36. A prostaglandin analog according to claim 33, wherein R$_7$ is

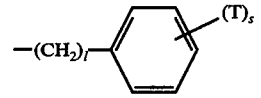

37. 9,11,15-Trideoxy-9α,11α-azo-17-phenyl-18,19,20-trinor-prostaglandin F$_2$, a prostaglandin analog according to claim 36.

38. A prostaglandin analog according to claim 33, wherein R$_7$ is —(CH$_2$)$_m$—CH$_3$.

39. A prostaglandin analog according to claim 38, wherein g is 3.

40. 9,11,15-Trideoxy-9α,11α-azo-2a,2b-dihomo-prostaglandin F$_2$, a prostaglandin analog according to claim 39.

41. A prostaglandin analog according to claim 38, wherein g is one.

42. A prostaglandin analog according to claim 41, wherein at least one of R$_3$ and R$_4$ is methyl.

43. A prostaglandin analog according to claim 42, wherein R$_3$ and R$_4$ are both methyl.

44. 9,11,15-Trideoxy-9α,11α-azo-16,16-dimethyl-prostaglandin F$_2$, methyl ester, a prostaglandin analog according to claim 43.

45. 9,11,15-Trideoxy-9α,11α-azo-16,16-dimethyl-prostaglandin F$_2$, a prostaglandin analog according to claim 43.

46. A prostaglandin analog according to claim 41, wherein at least one of R$_3$ and R$_4$ is fluoro.

47. A prostaglandin analog according to claim 46, wherein R$_3$ and R$_4$ are both fluoro.

48. 9,11,15-Trideoxy-9α,11α-azo-16,16-difluoro-prostaglandin F$_2$, methyl ester, a prostaglandin analog according to claim 47.

49. 9,11,15-Trideoxy-9α,11α-azo-16,16-difluoro-prostaglandin F$_2$, a prostaglandin analog according to claim 47.

50. A prostaglandin analog according to claim 41, wherein R$_3$ and R$_4$ are both hydrogen.

51. 9,11,15-Trideoxy-9α,11α-azo-prostaglandin F$_2$, methyl ester, a prostaglandin analog according to claim 50.

52. 9,11,15-Trideoxy-9α,11α-azo-prostaglandin F$_2$, a prostaglandin analog according to claim 50.

* * * * *

UNITED STATES PATENT OFFICE
CERTIFICATE OF CORRECTION

Patent No. 4,112,224                Dated   5 September 1978

Inventor(s)  Gordon L. Bundy

It is certified that error appears in the above-identified patent and that said Letters Patent are hereby corrected as shown below:

The Title should read -- BIHETEROCYCLIC-9,11,15-TRIDEOXY-PGF COMPOUNDS --;
In the Abstract (after formulas), "9,11-trideoxy-" should read -- 9,11,15-trideoxy- --;
Column 1, lines 22-28, the formula should appear as follows:

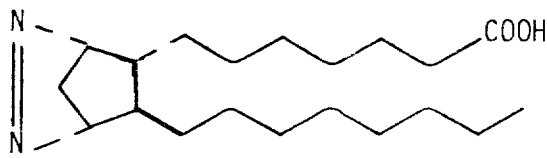

Column 3, line 4, "9,11-dideoxy-9α--azo-PGF$_1$" should read -- 9,11-dideoxy-9α,11α-azo-PGF$_1$ --;
Column 4, line 61,
"-CH=N-N-NHC(=O)-NH$_2$"  should read -- -CH=N-NHC(=O)-NH$_2$ --;
Column 5, line 1, "amido" should read -- amino -- line 28, "cycloamido" should read -- cycloamino --; line 52, "carbonylamido" should read -- carbonylamino --; line 55, "sulphonylamido" should read -- sulfonylamino --;

Column 5, line 58, "amido" should read -- amino --; line 59, "cycloamido" should read -- cycloamino --; Column 9, line 65, "alkylamido" should read -- alkylamino --;
Column 10, lines 6-7, "cycloalkylamido" should read -- cycloalkylamino --; line 18, "aralkylamido" should read -- aralkylamino --; line 21, "phenylamido" should read -- phenylamino --; lines 29-30, "carboxyalkylamido" should read -- carboxyalkylamino --; line 33, "carbamoylalkylamido" should read -- carbamoylalkylamino --; line 38, "acetylalkylamido" should read -- acetylalkylamino --; lines 40-41, "benzoylalkylamido" should read -- benzoylalkylamino --; lines 43-44, "benzoylalkylamido" should read -- benzoylalkylamino --;

UNITED STATES PATENT OFFICE
CERTIFICATE OF CORRECTION

Patent No. 4,112,224           Dated  5 September 1978

Inventor(s)  Gordon L. Bundy

It is certified that error appears in the above-identified patent and that said Letters Patent are hereby corrected as shown below:

Column 11, lines 22 and 24, "pyridylamido" should read -- pyridylamino --; lines 27 and 33, "pyridylalkylamido" should read -- pyridylalkylamino --; line 44, "hydroxyalkyl" should read -- hydroxyalkylamino --; lines 50-51 "dihydroxyalkylamido" should read -- dihydroxyalkylamino --; line 67, "cycloamido" should read -- cycloamino --;

Column 12, line 4, "carbonylamido" should read -- carbonylamino --; line 7, "sulfonylamido" should read -- sulfonylamino --; line 12, "hdyrazine," should read -- hydrazine, --;

Column 15, line 8, "thereo," should read -- thereof, --;

Column 24, lines 55-65, that portion of Formula XLV reading

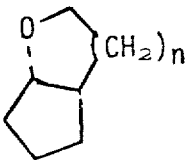     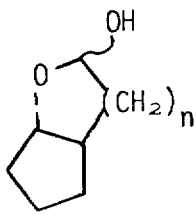

Column 34, line 48, "$(R_9)_2$)," should read -- $(R_9)_2O$, --;
Column 36, line 35, "$PGF_{62}$ compounds" should read -- $PGF_\beta$ compounds --;
Column 37, line 21, "substitued" should read -- substituted --;
Column 41, line 12, "an ortho-CH-CH is" should read -- an ortho-4-bromo-alkanoate is --;
Column 46, line 49, "formula CVII" should read -- formula CVIII --;
Column 49, line 17, "ot to esters" should read -- or to esters --; line 28, "alylk," should read -- alkyl, --;
Column 50, lines 13, 26, 31-32, "amido and cycloamido" should read -- amino and cycloamino --; line 28, "carbonylamido" should read -- carbonylamino --; line 29, "sulphonylamido" should read -- sulfonylamino --; line 36, "an quivalent" should read -- an equivalent --; line 53 and line 65, "amido or cycloamido" should read -- amino or cycloamino --; line 67, "carbonylamido and sulfonylamido" should read -- carbonylamino and sulfonylamino --;
Column 51, line 5, "carbonylamido or sulfonylamido" should read

UNITED STATES PATENT OFFICE
CERTIFICATE OF CORRECTION

Patent No. 4,112,224  Dated 5 September 1978

Inventor(s) Gordon L. Bundy

It is certified that error appears in the above-identified patent and that said Letters Patent are hereby corrected as shown below:

-- carbonylamion or sulfonylamino --; lines 8-9, 15, and 19, "sulfonylamido" should read -- sulfonylamino --; line 11, "amido and cycloamido" should read -- amino and cycloamino --; line 46, "Eavporation" should read -- Evaporation --;

Column 53, line 53, "4.2, 4.7, 4186-5.82," should read -- 4.2, 4.7, 4.86-5.82, --;

Column 54, line 68, "pure γ-lactol" should read -- pure δ-lactol --;

Column 55, line 24, "$Y_2M_9$, $L_1$, and" should read -- $Y_2$, $M_9$, $L_1$, and --

Column 56, line 31, "13,14-dihydrotrans-" should read -- 13,14-dihydrotrans- --; line 33, "$Y_3$ is cis-CH'CH-$CH_2$-" should read -- $Y_3$ is cis-CH=CH-$CH_2$- --;

Column 57, line 34, "$Y_6$ is -C=$CH_2$-," should read -- $Y_6$ is -C≡C-$CH_2$- --;

Column 58, line 45, "tris-(triphenylphoshine)" should read -- tris-(triphenylphosphine) --;

Column 59, line 10, "$PGF_{62}$-type" should read -- PGFβ-type --; line 56, "trans-CH=CH-$CG_2$-," should read -- trans-CH=CH-$CH_2$-, --; line 56, "$R_3$ and $R_4$ of the $L_1$—moiety" should read -- $R_3$ and $R_4$ of the $L_1$ moiety --

Column 61, line 15, "Example" should read -- EXAMPLE 3 --; line 47, "an Z1, $W_1$," should read -- and $Z_1$, $W_1$, --;

Column 63, line 2, "16-Methyl-b 17-phenyl-" should read -- 16-Methyl-17-phenyl- --;

Column 68, line 12, "4,5,6-trinor-16-16-methyl-" should read -- 4,5,6-trinor-16-methyl- --; lines 20-21, "4,5,6,18,19,20-trinor-" should read -- 4,5,6,18,19,20-hexanor- --; line 44, "3-oxa-16-16-phenoxy-" should read -- 3-oxa-16-phenoxy- --;

Column 73, line 36, "13,14-didehydro-" should read -- 13,14-dihydro- --;

Column 76, line 22, "$c^{-1}$" should read -- $cm^{-1}$ --;

Column 80, line 5, "N-acetyl-]α-11α-" should read -- N-acetyl-9α,11α- --; line 10, "9α,11α (acety)hydrazino-" should read -- 9α,11α-(acetyl)hydrazino- --; line 44, "-C|C-$CH_2$-" should read -- -C≡C-$CH_2$- --;

UNITED STATES PATENT OFFICE
CERTIFICATE OF CORRECTION

Patent No. 4,112,224  Dated 5 September 1978

Inventor(s) Gordon L. Bundy

It is certified that error appears in the above-identified patent and that said Letters Patent are hereby corrected as shown below:

Column 82, lines 50-53,

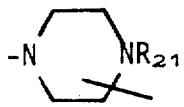  should read  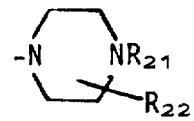

Column 83, line 40, "wherein $T_1$ is" should read -- wherein $Y_1$ is --.

Signed and Sealed this

Twenty-fifth Day of August 1981

[SEAL]

Attest:

GERALD J. MOSSINGHOFF

Attesting Officer  Commissioner of Patents and Trademarks